US007524879B2

(12) United States Patent
Beatch et al.

(10) Patent No.: US 7,524,879 B2
(45) Date of Patent: *Apr. 28, 2009

(54) ION CHANNEL MODULATING COMPOUNDS AND USES THEREOF

(75) Inventors: Gregory N. Beatch, Vancouver (CA); Bertrand M. C. Plouvier, Vancouver (CA); Tao Sheng, Westwood, MA (US); Michael J. A. Walker, Vancouver (CA); Richard A. Wall, Vancouver (CA); Sandro L. Yong, Cleveland, OH (US); Jeff Jiqun Zhu, High Point, NC (US); Alexander R. Zolotoy, Richmond (CA)

(73) Assignee: Cardiome Pharma Corp., Vancouver, BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/757,880

(22) Filed: Jun. 4, 2007

(65) Prior Publication Data

US 2008/0004333 A1    Jan. 3, 2008

Related U.S. Application Data

(63) Continuation-in-part of application No. 11/619,136, filed on Jan. 2, 2007, which is a continuation of application No. 11/342,270, filed on Jan. 27, 2006, now Pat. No. 7,259,184, which is a continuation of application No. 11/018,428, filed on Dec. 21, 2004, now Pat. No. 7,057,053, which is a continuation of application No. 10/674,684, filed on Sep. 29, 2003, now Pat. No. 7,101,877, which is a continuation of application No. 09/680,988, filed on Oct. 6, 2000, now abandoned.

(51) Int. Cl.
*A61K 31/40* (2006.01)
(52) U.S. Cl. ...................................... 514/424
(58) Field of Classification Search .................. 514/424
See application file for complete search history.

(56) References Cited

U.S. PATENT DOCUMENTS

| 2,954,380 | A | 9/1960 | Shapiro et al. ............. 260/268 |
|---|---|---|---|
| 3,218,328 | A | 11/1965 | Shapiro et al. ............. 260/294 |
| 4,145,435 | A | 3/1979 | Szmuszkovicz ............. 424/274 |
| 4,179,501 | A | 12/1979 | Szmuszkovicz ............. 424/226 |
| 4,598,087 | A | 7/1986 | Horwell ..................... 514/429 |
| 4,656,182 | A | 4/1987 | Horwell ..................... 514/324 |
| 4,663,343 | A | 5/1987 | Horwell et al. ............. 514/429 |
| 4,855,316 | A | 8/1989 | Horwell et al. ............. 514/422 |
| 4,880,800 | A | 11/1989 | Wallis et al. ............... 514/211 |
| 4,906,655 | A | 3/1990 | Horwell et al. ............. 514/422 |
| 5,019,588 | A | 5/1991 | Horwell et al. ............. 514/409 |
| 5,051,428 | A | 9/1991 | Horwell et al. ............. 514/320 |
| 5,059,620 | A | 10/1991 | Stout et al. ................. 514/422 |
| 5,492,825 | A | 2/1996 | Jan et al. ................. 435/240.2 |
| 5,506,257 | A | 4/1996 | MacLeod et al. ............. 514/422 |
| 5,637,583 | A | 6/1997 | MacLeod et al. ............. 514/212 |
| 5,670,335 | A | 9/1997 | Jan et al. ....................... 435/29 |
| 5,728,535 | A | 3/1998 | Lester et al. ................... 435/7.2 |
| 5,734,021 | A | 3/1998 | Lester et al. ................. 530/350 |
| 5,750,537 | A | 5/1998 | Nomura et al. ............. 514/304 |
| 5,817,698 | A | 10/1998 | Brown et al. ................. 514/646 |
| 5,885,984 | A | 3/1999 | MacLeod et al. ............. 514/211 |
| 6,174,879 | B1 | 1/2001 | MacLeod et al. ....... 514/212.01 |
| 6,180,632 | B1 | 1/2001 | Myers et al. .............. 514/252.1 |
| 6,210,809 | B1 | 4/2001 | Okutomi et al. ............. 428/546 |
| 6,214,810 | B1 | 4/2001 | Fermini et al. ................. 514/75 |
| 6,451,819 | B2 | 9/2002 | Alanine et al. ............. 514/326 |
| 6,521,619 | B2 | 2/2003 | Link et al. ................. 514/237.2 |
| 6,649,603 | B2 | 11/2003 | Sum ..................... 514/210.01 |
| 6,979,685 | B1 | 12/2005 | Beatch et al. ............. 514/231.2 |
| 7,053,087 | B1 | 5/2006 | Beatch et al. ............. 514/237.8 |
| 7,259,184 | B2 * | 8/2007 | Beatch et al. ............... 514/424 |
| 2005/0026993 | A1 | 2/2005 | Beatch et al. ............... 514/424 |
| 2005/0038256 | A1 | 2/2005 | Barrett et al. ............... 546/236 |
| 2005/0070552 | A1 | 3/2005 | Fedida et al. ........... 514/255.06 |
| 2005/0119315 | A1 | 6/2005 | Fedida et al. ............... 514/355 |
| 2005/0209307 | A1 | 9/2005 | Bain et al. ..................... 514/1 |
| 2006/0247300 | A1 | 11/2006 | Beatch et al. ............... 548/557 |
| 2006/0252753 | A1 | 11/2006 | Beatch et al. ............. 514/237.8 |

(Continued)

FOREIGN PATENT DOCUMENTS

CA    1234808    4/1988

(Continued)

OTHER PUBLICATIONS

Stevenson et al., Atrial Fibrillation and Heart Failure, Dec. 2, 2004, N Engl J Med, 351: 23, p. 2438.*
Adcock et al., "RSD931, a novel anti-tussive agent acting on airway sensory nerves", Br J Pharm 138(3):407-416, 2003.
Altria et al., "Capillary Electrophoresis as a Routine Analytical Tool in Pharmaceutical Analysis", LCGC 19(9): 972-985, Sep. 2001.
Amin et al., "RPR 101821, a New Potent Cholesterol-lowering Agent: Inhibition of Squalene Synthase and 7-Dehydrocholesterol Reductase", Naunyn-Schmiedeberg's Arch Pharmacol 353:233-240, 1996.
Alzheimer's Disease Information Page [online], [retrieved on Oct. 3, 2006]. Retrieved from the Internet, URL: <http://www.ninds.nih.gov/disorders/alzheimersdisease/alzheimersdisease.htm>.
Bain et al., "Better Antiarrhythmics? Development of Antiarrhythmic Drugs Selective for Ischaemia-Dependent Arrhythmias", Drug Development Research 42:198-210, 1997.
Barrett and Walker, "Glibenclamide Possesses Transient, Ischaemia Selective Class III Antiarrhythmic Actions But Does Not Prevent Ischaemic Arrhythmias", BPS Proceedings 116P, 1996.

(Continued)

*Primary Examiner*—Kamal A Saeed
*Assistant Examiner*—Kristin Bianchi
(74) *Attorney, Agent, or Firm*—Seed IP Law Group PLLC

(57) ABSTRACT

Ion channel modulating compounds are disclosed. The compounds of the present invention may be incorporated in compositions and kits. The present invention also discloses a variety of in vitro and in vivo uses for the compounds and compositions, including the treatment of arrhythmia and the production of analgesia and local anesthesia.

18 Claims, 5 Drawing Sheets

U.S. PATENT DOCUMENTS

| | | | |
|---|---|---|---|
| 2007/0099983 A1 | 5/2007 | Beatch et al. | 514/408 |
| 2007/0190156 A1* | 8/2007 | Beatch et al. | 424/489 |
| 2007/0197632 A1 | 8/2007 | Beatch et al. | 514/327 |

FOREIGN PATENT DOCUMENTS

| | | |
|---|---|---|
| CA | 1235122 | 4/1988 |
| CA | 2004575 | 6/1990 |
| CA | 2058502 | 6/1993 |
| CA | 2172513 | 3/1995 |
| CA | 2244209 A1 | 7/1997 |
| CA | 2008391 | 12/1997 |
| CA | 2289055 | 1/1999 |
| CA | 2268590 | 10/2000 |
| CA | 2132841 | 3/2001 |
| DE | 2 259 260 | 6/1974 |
| DE | 2 658 401 | 7/1978 |
| DE | 3 517 901 | 12/1985 |
| EP | 222533 A1 | 5/1987 |
| EP | 147085 A2 | 3/1990 |
| EP | 147085 B1 | 3/1990 |
| EP | 372466 A2 | 6/1990 |
| EP | 372466 A3 | 6/1990 |
| EP | 380063 A1 | 8/1990 |
| EP | 380063 BI | 8/1990 |
| EP | 552386 A1 | 7/1993 |
| EP | 720605 BI | 7/1996 |
| HU | 215963 B | 2/1995 |
| JP | 02-270864 | 11/1990 |
| WO | WO 93/19056 | 9/1993 |
| WO | WO 94/07843 | 4/1994 |
| WO | WO 94/14435 | 7/1994 |
| WO | WO 95/08544 | 3/1995 |
| WO | WO 95/28155 | 10/1995 |
| WO | WO 96/18615 | 6/1996 |
| WO | WO 96/23894 | 8/1996 |
| WO | WO 97/32857 | 9/1997 |
| WO | WO 97/49680 | 12/1997 |
| WO | WO 99/02159 | 1/1999 |
| WO | WO 99/03468 | 1/1999 |
| WO | WO 99/11252 | 3/1999 |
| WO | WO 99/16431 | 4/1999 |
| WO | WO 99/50205 | 10/1999 |
| WO | WO 99/50225 * | 10/1999 |
| WO | WO 00/47547 | 8/2000 |
| WO | WO 00/51981 | 9/2000 |
| WO | WO 01/96335 | 12/2001 |
| WO | WO 03/105756 | 12/2003 |
| WO | WO 2004/008103 | 1/2004 |
| WO | WO 2004/098525 | 11/2004 |
| WO | WO 2004/099137 | 11/2004 |

OTHER PUBLICATIONS

Barrett et al., "A Model of Myocardial Ischemia for the Simultaneous Assessment of Electrophysiological Changes and Arrhythmias in Intact Rabbits", J Pharmacol Toxicol Methods 37(1):27-36, 1997.

Barrett et al., "Ischaemia selectivity confers efficacy for suppression of ischaemia-induced arrhythmias in rats", Eur J Pharm 398:365-374, 2000.

Barrett et al., "Atypical Dose Response Curves for Antiarrhythmic Drugs", BPS Proceedings 115P, 1996.

Barrett, "Ischemia Selective Electrophysiological and Antiarrhythmic Actions of RSD1019 in Ischemic Cardiac Tissue", J Mol Cell Cardiol 29:197, 1997.

Barrett et al., "RSD1019 suppresses ischaemia-induced monophasic action potential shortening and arrhythmias in anaesthetized rabbits", Br J Pharm 131(3):405-414, 2000.

Beatch et al., "RSD1235 Selectively Prolongs Atrial Refractoriness and Terminates AF in Dogs with Electrically Remodelled Atria", Pharmacologist 44(2) (Supp I), A15:XIVth Wolrd Congress of Pharmacology: Meeting Abstracts, 2002. Abstract No. 22.11.

Beatch et al., "Effect of a Novel Anti-tussive Compound CP1 Against Citric Acid Induced Cough in Guinea-Pigs", Proc West Pharmacol Soc, 44:252, 2001.

Beatch et al., "Electrophysiological Profile of RSD1235, A New Drug for Conversion of Atrial Fibrillation", Abstract of U.S. Appl. No. 10/674,684, filed Sep. 29, 2003, now U.S. Patent No. 7,101,877 issued Sep. 5, 2006.

Beatch et al., "RSD1235 Rapidly and Effectively Terminates Atrial Fibrillation", Abstract submission ESC Congress Aug. 30-Sep. 3, 2003, in Vienna, Austria.

Beatch et al., "RSD1235, A Novel Atrial-Selective Antiarrhythmic Drug, Shows Rapid and Extensive Oral Absorption in Man", 12th International Congress on Cardiovascular Pharmacotherapy, May 7-10, 2003, Barcelona, Spain.

Beatch et al., "Ventricular Fibrillation, an Uncontrolled Arrhythmia Seeking New Targets", Drug Develop Res 55:45-52, 2002.

Beatch et al., "Aminocyclohexyl Ether Compounds and Uses Thereof," U.S. Appl. No. 11/690,361, filed Mar. 23, 2007; now pending.

Beatch, "Antihistamine-induced Ventricular Arrhythmias", BPS Proceedings 120P, 1996.

Beatch et al., "Characterization of a Non-Human Primate Model of Drug Induced Torsades De Pointes", Proc West Pharmacol Soc 40:13-16, 1997.

Beatch et al., "RSD1235 Selectively Prolongs Atrial Refractoriness and Terminates AF in Dogs with Electrically Remodelled Atria", Pace 24(Part II):698. Abstract 702, May 10, 2002.

Bian et al., "Effects of Kappa-opioid receptor stimulation in the heart and the involvement of protein kinase C", Brit J Pharmacol 124:600-606, 1998.

Billman, "RSD-1235", Curr Opin Investigational Drugs 4(3):352-354, 2003.

Boiadjiev and Lightner, "pH-Sensitive Exciton Chirality Chromophore. Solvatochromic Effects on Circular Dichroism Spectra", Tetrahedron: Asymmetry 7(10):2825-2832, 1996.

Bowen et al., "Characterization of the Enantiomers of cis-N-[2-(3,4-Dichlorophenyl)Ethyl]-N-Methyl-2-(1-Pyrrolidinyl)Cyclohexylamine (BD737 and BD738): Novel Compounds with High Affinity, Selectivity and Biological Efficacy at Sigma Receptors", J Pharmacol Exp Ther 262(1):32-40, 1992.

Cardiome Pharma Corp. (Jan. 31, 2001). "Nortran Drug Effective in Atrial Arrhythmia Model" (http://cardiome.com/wordpress/?p=104). Press Release.

Cardiome Pharma Corp. (Jun. 21, 2001). "Nortran Antiarrhythmia Drug Demonstrates Oral Bioavailability" (http://cardiome.com/wordpress/?p=99). Press Release.

Cardiome Pharma Corp. (Jul. 30, 2001). "Cardiome Pharma Completes Phase I Safety Study" (http://cardiome.com/wordpress/?p=97). Press Release.

Cardiome Pharma Corp. (Jan. 17, 2002). "Cardiome Reports Dosing of First Patient in Pivotal Phase II Study" (http://cardiome.com/wordpress/?p=90). Press Release.

Cardiome Pharma Corp. (Sep. 3, 2002). "Cardiome Drug Effective for Heart Patients" (http://cardiome.com/wordpress/?p=75). Press Release.

Cardiome Pharma Corp. (Dec. 5, 2002). "Cardiome Reports Oral Absorption of RSD1235 in Humans" (http://cardiome.com/wordpress/?p=72). Press Release.

Cardiome Pharma Corp. (Dec. 20, 2004). "Cardiome's Pivotal AF Study Achieves Primary Endpoint" (http://cardiome.com/wordpress/?p=14). Press Release.

Cardiome Pharma Corp. (Feb. 4, 2005). "Cardiome Reports Additional ACT 1 Clinical Results" (http://cardiome.com/wordpress/?p=2). Press Release.

Cardiome Pharma Corp. (Apr. 25, 2005). "Cardiome Successfully Completes Second Phase 1 Trial" (http://cardiome.com/wordpress/?p=230). Press Release.

Cardiome Pharma Corp. (Aug. 31, 2005). "Cardiome Successfully Completes RSD1235 Oral Phase 1 Trial" (http://cardiome.com/wordpress/?p=255). Press Release.

Cardiome Pharma Corp. (Sep. 29, 2005). "Cardiome and Astellas Announce Positive Results from Second Phase 3 Trial" (http://cardiome.com/wordpress/?p=262). Press Release.

Cardiome Pharma Corp. (May 5, 2006). "Cardiome Reports Additional Phase 1 Trial Data for Oral RSD1235" (http://cardiome.com/wordpress/?p=291). Press Release.

Cardiome Pharma Corp. (Jul. 24, 2006). "Cardiome Announces Interim Phase 2A Results for Oral RSD1235" (http://cardiome.com/wordpress/?p=312). Press Release.

Cardiome Pharma Corp. (Sep. 13, 2006). "Cardiome Announces Positive Phase 2A Results for Oral RSD1235" (http://cardiome.com/wordpress/?p=321). Press Release.

Cardiome Pharma Corp. Healthcare (Underweight) Company Report Dec. 12, 2002. 26 pages.

Clohs and Wong, "Validation of a capillary electrophoresis assay for assessing the metabolic stability of verapamil in human liver microsomes", J Cap Elec & Microchip Tech. 007(5/6):113-117, 2002.

Clohs, "Capillary Electrophoresis And Its Applications In The Pharmaceutical Industry—Short Course: One Platform Fits Many Applications", CSC 2002, 52 pages.

Clohs, "Capillary Electrophoresis as an Analytical Tool in the Drug Discovery Process", Presentation CE Symposium, Aug. 2000, 40 pages.

Clohs, "The Versatility of CE for Drug Pharmacokinetics and Metabolism Studies", CE in the Biotechnology & Pharmaceutical Industries (Symposium), Boston, Aug. 2001, 46 pages.

Clohs, "Pharmacokinetics profiling of new drug candidates: a key process in drug discovery", Beckman Coulter P/ACE Setter 4(1):6, Jun. 2000.

Clohs and Winstanley, "CE Analysis of Propranolol in Human Serum Using Dynamic Capillary Coating", CE Currents: LCGC Europe, Reader Service 14, pp. 289-293, May 2002.

Clohs, "Bio-Analytical Applications of Capillary Electrophoresis In A Drug Discovery Setting", CSC Seminar, Jun. 5, 2002, 29 pages.

Clohs, "CE and Drug Metabolism Studies: A Powerful Combination in Drug Discovery", CE in the Biotechnology and Pharmaceutical Industries (Symposium), Washington, DC, Aug. 2002, 31 pages.

Crotti et al., "Regiochemical control of the ring-opening of epoxides by means of chelating processes Part 13 . . .", Chemical Abstracts 129(17):662-663, Abstract No. 216472k, 1998.

Crotti et al., "Synthesis and Ring-Opening Reactions of the Diastereoisomeric cis- and trans-Epoxides Derived from 3-(Benzyloxy)cyclopentene and 2-(Benzyloxy)-2,5-dihydrofuran", Eur J Org Chem 8:1675-1686, 1998.

De Costa et al., "Synthesis and Evaluation of N-Substituted cis-N-Methyl-2-(1-pyrrolidinyl)cyclohexylamines as High Affinity σ Receptor Ligands. Identification of a New Class of Highly Potent and Selective σ Receptor Probes", J Med Chem 33:3100-3110, 1990.

Doci et al., "Local Anesthetic Effects of Intradermal RSD921 In Healthy Subjects", Proceedings of the 100th Annual Meeting of the American Society for Clinical Pharmacology and Therapeutics, San Antonio, Texas, Mar. 18-20, 1999, Abstract PIII-2 in Clin Pharm & Therap 65(2):177, Feb. 1999.

Duan et al., "Potassium Channel Blocking Properties of Propafenone in Rabbit Atrial Myocytes", J Pharm Exp Ther 264(3): 1113-1123, 1993.

Ezrin et al., "Safety and Pharmacokinetics of RSD1235, a Novel Atrial Fibrillation Converting Drug, in Healthy Volunteers", Abstracts: 11th Int. Congress Cardiovasc. Pharmacother. 16 Abstract P297, 2002.

Ezrin et al., "A Dose-Ranging Study of RSD1235, A Novel Antiarrhythmic Agent, In Healthy Volunteers", Pharmacologist, 44(2) (Supplement I), A15: XIVth World Congress of Pharmacology: Meeting Abstracts, 2002. Abstract No. 22.10.

Fedida et al., "Kv1.5 is an Important Component of Repolarizing K[+] Current in Canine Atrial Myocytes", Circulation Research Peer Review Plus Manuscript PDF, 38 pages, 2002.

Franciosi et al., "Phase II Clinical Trial of RSD921 as a Local Anaesthetic in Patients Undergoing Venous Cannulation For Elective Treatment", in Proceedings of the 28th Annual ACCP Meeting Abstract 32, p. 977, Feb. 2000.

Franciosi and McLarnon, "pH-dependent blocking actions of three novel antiarrhythmic compounds on K[+] and Na[+] currents in rat ventricular myocytes", Eur J Pharm 425:95-107, 2001.

Franqueza et al., "Effects of propafenone and 5-hydroxy-propafenone on hKv1.5 channels", Br J Pharm 125:969-978, 1998.

Friess et al., "Central Activity Evoked in the Cat by Cis-Trans Isomers of 1,2-Aminocyclohexanol Dervivatives", Taxicol Appl Pharmacol 3:638-653, 1961.

Grant, "Mechanisms of Atrial Fibrillation and Action of Drugs Used in its Management", Am J Cardiol 82:43N-49N, Oct. 16, 1998.

Halfpenny et al., "Highly Selective k-Opioid Analgesics. 3. Synthesis and Structure-Activity Relationships of Novel N-[2-(1-Pyrrolidinyl)-4- or -5-substituted-cyclohexyl]arylacetamide Derivatives", J Med Chem 33:286-291, 1990.

Halfpenny et al., "Highly Selective k-Opioid Analgesics. 2. Synthesis and Structure-Activity Relationships of Novel N-[(2-Aminocyclohexyl)aryl]acetamide Derivatives", J Med Chem 32:1620-1626, 1989.

Hayes et al., "RSD 992 Enhances Erection and Copulation in Rats and Erection in Primates", Int J Impotence Res, p. 189 (Abstract P24), 1996.

Hayes et al., "Actions of Arylpiperazines on Corpus Cavernosum Smooth Muscle In Vitro", Asia Pac J Pharmacol 12:97-103, 1997.

Hayes et al., "Direct Actions of Arylpiperazines on Rabbit and Human Corpus Caversonal Smooth Muscle In Vitro", Asia Par J Pharmacol, Abstract S15, 1997.

Hesketh et al., "Safety of RSD1235 in a rabbit Purkinje fiber model", in Proceedings of the XIVth World Congress of Phar. Meeting, Abstract No. 22.12, 2002.

Keefe et al., "New Antiarrhythmic Drugs: Their Place in Therapy", Drugs 22:363-400, 1981.

Kertesz et al., "The Electrophysiological and Antiarrhythmic Actions of RSD Analogs of U50,488H in Rats", in Proceedings of the West Pharmacol Soc. 9 pages, 1994.

Lang et al., "Clinical Evaluation of RSD921 As a Local Anaesthetic in Patients Undergoing Venous Cannulation for Elective Treatment", Clin Pharm & Therapeutics, p. 142, Feb. 2000. Abstract PIII-1.

Lewis et al., "Enzyme inhibition during the conversion of squalene to cholesterol", Steroids 60:475-483, Jul. 1995.

Li et al., "Adrenergic Modulation of Ultrarapid Delayed Rectifier K[+] Current in Human Atrial Myocytes", Circ Res 78(5):903-915, May 1996.

Malayev et al., "Mechanism of Clofilium Block of the Human Kv1.5 Delayed Rectifier Potassium Channel", Mol Pharm 47:198-205, 1995.

Martens et al., "Einfache Synthese neuer anellierter Pyrrole", J Synth Org Chem 12:965-967, Dec. 1989.

Matyus et al., "Antiarrhythmic Agents: Current Status and Perspectives", Medicinal Research Reviews 17(5):427-451, 1997.

McLarnon et al., "Mixed Block of K[+] and Na[+] Currents by KC8851, A Structural Analogue of Tedisamil In Vitro and In Vivo Studies", BPS Proceedings 114P, 1996.

Moorman et al., "$pK_a$ Does Not Predict pH Potentiation of Sodium Channel Blockade by Lidocaine and W6211 in Guinea Pig Ventricular Myocardium", The Journal of Pharmacology and Experimental Therapeutics 238(1):159-166, 1986.

Morisawa et al., "Preparation of fluorocarbocyclic nucleosides as antitumor agents", Chemical Abstracts 115(5):904-905, abstract No. 50215n, 1991.

Nakashima et al., "Angiotensin II Type I Receptor Antagonist Prevents the Promotion of Atrial Fibrillation", Pace 24(Part II):698, May 10, 2002. Abstract 701.

Nattel et al., "Effects of the novel antiarrhythmic agent azimilide on experimental atrial fibrillation and atrial electrophysiologic properties", Cardiovascular Research 37:627-635, 1998.

Nattel et al., "RSD1235: a novel antiarrhythmic agent with a unique electrophysiological profile that terminates AF in dogs", Eur. Heart J 22(Suppl):448 (Abstract P2362), 2001.

Nattel, "Experimental evidence for proarrhythmic mechanisms of antiarrhythmic drugs", Cardiovascular Research 37:567-577, 1998.

Nattel et al., "The Role of Channel Opening in Transient Outward Current Block By Quinidine, Flecainide, and 4-Aminopyridine in Human Atrial Myocytes", K Channels II: Regulation and Block, Abstract No. Tu-Pos403, 1994.

Nishi et al., "Studies on 2-Oxoquinoline Derivatives as Blood Platelet Aggregation Inhibitors. IV. Synthesis and Biological Activity of the Metabolites of 6-[4-(1-Cyclohexyl-1H-5-tetrazolyl)butoxy]-2-oxo-1,2,3,4-tetrahydroquinoline (OPC-13013)", Chem. Pharm. Bull 33(3):1140-1147, 1985.

Orth et al., "Cyclopentane-1-amines", Chemical Abstracts 89(15):555, Abstract No. 129113f, 1978.

Orth et al., "The Novel AF Conversion Agent RSD1235 Preferentially Blocks a Late Component of the Human Heart (hH1) $Na^+$ Current Active During Repolarization", EP abstracts Oct. 3, 2003.

Plouvier et al., "Synthesis and Structure Activity Relationships of a Series of 2-Aminocyclohexyl . . . as Potential Ischaemia Selective Ventricular Antiarrhythmics", BMPS 994.

Pugsley and Goldin, "Molecular analysis of the $Na^+$ channel blocking actions of the novel class I antiarrhythmic", Br J Pharm 127:9-18, 1999.

Pugsley et al., "A Characterization of the Antiarrhythmic and Electrophysiological Properties of RSD992, A Novel Arylpiperazine Drug", XIVth World Congress of Pharmacology: Meeting Abstract 22.8, in Pharmacologist 44(2, Supp 1):A15, 2002.

Pugsley et al., "Electropharmacology of Two New Class 1 agents", Heart and Stroke Annual Conference, p. 12, 1995.

Pugsley et al., "Sodium Channel-Blocking Properties of Spiradoline, a Kappa Receptor Agonist, are Responsible for Its Antiarrhythmic Action in the Rat", J Cardiovas Pharmacol 32:863-874, 1998.

Pugsley et al., "Are the arrhythmias due to myocardial ischaemia and infarction dependent upon the sympathetic system?", Cardiol Res 43:830-831, 1999.

Ribeiro et al., "Determination of RSD921 in human plasma by high-performance liquid chromatography-tandem mass spectrometry using tri-deuterated RSD921 as internal standard: application to a phase I clinical trial", J Mass Spectrom 36:1133-1139, 2001.

Rich et al., "Quinidine Block of the Human Cardiac hKv1.5 Channel in Inside-Out Patches, K Channels II: Regulation and Block", Abstract No. Tu-Pos404, p. A209, 1999.

Roden and George, "The Cardiac Ion Channels: Relevance to Management of Arrhythmias", Annu Rev Med 47:135-148, 1996.

Roy et al., "RSD1235 Rapidly and Effectively Terminates Atrial Fibrillation", Eur Heart J, p. 3699, 2003.

Rynbrandt et al., "Cis-1-[2-(p-Anisidinomethyl)cyclohexyl]piperidine and Related Compounds. Oral Hypoglycemic Agents", J Med Chem 14(10): 985-987, 1971.

Sanguinetti, "Modulation of Potassium Channels by Antiarrhythmic and Antihypertensive Drugs", Hypertension 19(3):228-236, Mar. 1992.

Singh, "Antiarrhythmic Drugs: A Reorientation in Light of Recent Developments in the Control of Disorders of Rhythm", Am J Cardiol 81(6A):3D-13D, Mar. 19, 1998.

Singh, "Atrial Fibrillation: Epidemiologic Considerations and Rationale for Conversion and Maintenance of Sinus Rhythm", J Cardiovasc Pharmacol Therapeut 8(Supp 1):S13-S26, 2003.

Snyders et al., "A Rapidly Activating and Slowly Inactivating Potassium Channel Cloned from Human Heart", J. Gen. Physiol. 101:513-543, Apr. 1993.

Snyders and Yeola, "Determinants of Antiarrhythmic Drug Action—Electrostatic and Hydrophobic Components of Block of the Human Cardiac hKv1.5 Channel", Circ Res 77(3):575-583, Sep. 1995.

Srilatha et al., "Alterations in Rabbit Corpus Cavernosal Pharmacology By High Cholesterol Diet", Asia Par J Pharmacol, Abstract S15, 1997.

Steinbeck, "Proarrhythmische Wirkungen von Antiarrhythmika—Theoretische und Klinische Aspekte", Z Kardiol 81(Supp 4):139-143, 1992.

Stevenson, Atrial Fibrillation and Heart Failure—Five More Years, N Engl J Med 351(23):2437-2440, Dec. 2, 2004.

Tong et al., "Determination of an arylether antiarrhythmic and its N-dealkyl metabolite in rat plasma and hepatic microsomal incubates using liquid chromatography-tandem mass spectrometry", J Chromatog B 759:259-266, 2001.

Valenzuela et al., "Comparative effects of nonsedating histamine $H_1$ receptor antagonists, ebastine and terfenadine, on human Kv1.5 channels", Eur J Pharm 326:257-263, 1997.

Valenzuela et al., "Effects of Ropivacaine on a Potassium Channel (hKv1.5) Cloned from Human Ventricle", Anesthesiology 86:718-728, 1997.

Walker, "Antiarrhythmic Drug Development—Illusion and Disillusion?", Drug Develop Res 55:1-2, 2002.

Walker et al., "Determination of an arylacetamide antiarrhythmic in rat blood and tissues using reversed-phase high-performance liquid chromatography", J Chromatog B 675:257-263, 1996.

Walker et al., "Increased Electrophysiological Activity in Raised $K^+$ and low pH Improves Antiarrhythmic Efficacy for a Group of Morpholinocyclohexyl Derivatives", BPS Proceedings 118P, 1996.

Walker and Guppy, "Targeting Ischemic Ventricular Arrhythmias", Cardiac Drug Development Guide, Humana Press Inc., Totowa, NJ, pp. 175-201, 2003.

Wang et al., "Effects of Flecainide, Quinidine, and 4-Aminopyridine on Transient Outward and Ultrarapid Delayed Rectifier Currents in Human Atrial Myocytes", J Pharm Exp Ther 272(1):184-196, 1995.

Wang et al., "Sustained Depolarization-Induced Outward Current in Human Atrial Myocytes", Circ. Res. 73(6):1061-1076, Dec. 1993.

Wat et al., "Effects of Arylbenzacetamides on Neuromuscular Preparation", Proc West Pharmacol Soc 1994.

Wolf et al., "Impact of Atrial Fibrillation on Mortality, Stroke, and Medical Costs", Arch Intern Med 158: 229-234, Feb. 9, 1998.

Wong and Clohs, "Protein Binding Study of AA5, a New Antiarrhythmic Drug", Nortran Pharmaceuticals Inc., Vancouver, BC, Poster Conference, Aug. 2000.

Wong and Clohs, "Capillary Electrophoresis Assay to Assess In Vitro Metabolic Stability of Novel Compounds in Human Liver Microsomes", Cardiome Pharma Corp., Vancouver, BC, AAPS Poster, Oct. 2001.

Yeola et al., "Molecular Analysis of a Binding Site for Quinidine in a Human Cardiac Delayed Rectifier $K^+$ Channel"—Role of S6 in Antiarrhythmic Drug Binding, Circ Res 78(6): 1105-1114, Jun. 1996.

Yong et al., "Low pKa Predicts Antiarrhythmic Efficacy in a Series of Aminocyclohexyl Esters", J Mol Cell Cardiol. Abstract 057, 1997.

Yong et al., "RSD1000: A Novel Antiarrhythmic Agent with Increased Potency Under Acidic and High-Potassium Conditions", J Pharm Exp Ther 289(1):236-244, 1999.

Yong et al., "RSD1000: A Novel Antiarrhythmic Agent with an Improved Therapeutic Index", BPS Proceedings 119P, 1996.

Yong et al., "SAR Evidence that Antiarrhythmic Activity is Unrelated to Opioid Kappa Agonist Activity", BPS Proceedings 117P, 1996.

Zhang et al., "Inhibition of [$^3$H]-U69593 binding and the cardiac effects of U50, 488H by calcium channel blockers in the rat heart", Brit J Pharmacol 120:827-832, 1997.

Zolotoy et al., "Physicochemical Determinants for Drug Induced Blockade of HERG Potassium Channels: Effect of Charge and Charge Shielding", Curr Med Chem 1(3): 1-17, 2003.

* cited by examiner

ION CHANNEL MODULATING COMPOUNDS AND USES THEREOF

CROSS-REFERENCES TO RELATED APPLICATIONS

This application is a continuation-in-part of U.S. patent application Ser. No. 11/619,136 filed Jan. 2, 2007, now pending, which is a continuation of U.S. patent application Ser. No. 11/450,921 filed Jun. 9, 2006, now pending, which is a continuation of U.S. patent application Ser. No. 11/342,270 filed Jan. 27, 2006, now pending; which is a continuation of U.S. patent application Ser. No. 11/018,428 filed Dec. 21, 2004 (U.S. Pat. No. 7,057,053); which is a continuation of U.S. patent application Ser. No. 10/674,684 filed Sep. 29, 2003 (U.S. Pat. No. 7,101,877); which is a continuation of U.S. patent application Ser. No. 09/680,988, filed Oct. 6, 2000 (now abandoned). These applications are incorporated herein by reference in their entireties.

BACKGROUND OF THE INVENTION

1. Field of the Invention

The present invention is generally directed toward ion channel modulating compounds, pharmaceutical compositions and kits containing the ion channel modulating compounds, and therapeutic uses thereof.

2. Description of the Related Art

Cardiac ion channels are proteins that reside in the cell membrane and control the electrical activity of cardiac tissue. In response to external stimuli, such as changes in potential across the cell membrane, ion channels can form a pore through the cell membrane, and allow movement of specific ions into or out of the cell. The integrated behavior of thousands of ion channels in a single cell results in an ion current, and the integrated behavior of many ion currents makes up the characteristic cardiac action potential.

Arrhythmia is a variation from the normal rhythm of the heart beat and generally represents the end product of abnormal ion-channel structure, number or function. Both atrial arrhythmias and ventricular arrhythmias are known. The major cause of fatalities due to cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these will be first heart attacks and 450,000 will be recurrent attacks. About one-third of the people experiencing these attacks will die of them. At least 250,000 people a year die of coronary heart disease with 1 hour of the onset of symptoms and before they reach a hospital. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., *N. Engl. J. Med.* 327(14):1031 Oct. 1, 1992, discussion 1031-2; Kannel and Wolf, *Am. Heart J.* 123(1):264-7 Jan. 1992). Its prevalence is likely to increase as the population ages and it is estimated that 3-5% of patients over the age of 60 years have AF (Kannel W. B., Abbot R. D., Savage D. D., McNamara P. M., *N. Engl. J. Med.* 306(17): 1018-22, 1982; Wolf P. A., Abbot R. D., Kannel W. B. *Stroke.* 22(8):983-8, 1991). While AF is rarely fatal, it can impair cardiac function and is a major cause of stroke (Hinton R. C., Kistler J. P., Fallon J. T., Friedlich A. L., Fisher C. M., *American Journal of Cardiology* 40(4):509-13, 1977; Wolf P. A., Abbot R. D., Kannel W. B., *Archives of Internal Medicine* 147(9):1561-4, 1987; Wolf P. A., Abbot R. D., Kannel W. B. *Stroke.* 22(8):983-8, 1991; Cabin H. S., Clubb K. S., Hall C., Perlmutter R. A., Feinstein A. R., *American Journal of Cardiology* 65(16):1112-6, 1990).

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, there is no satisfactory pharmacotherapy for the treatment and/or prevention of ventricular fibrillation during acute ischemia. In fact, many Class I antiarrhythmic compounds may actually increase mortality in patients who have had a myocardial infarction.

Class Ia, Ic and III antiarrhythmic drugs have been used to convert recent onset AF to sinus rhythm and prevent recurrence of the arrhythmia (Fuch and Podrid, 1992; Nattel S., Hadjis T., Talajic M., *Drugs* 48(3):345-71, 1994). However, drug therapy is often limited by adverse effects, including the possibility of increased mortality, and inadequate efficacy (Feld G. K., *Circulation.* 83(6):2248-50, 1990; Coplen S. E., Antman E. M., Berlin J. A., Hewitt P., Chalmers T. C., *Circulation* 1991; 83(2):714 and *Circulation* 82(4):1106-16, 1990; Flaker G. C., Blackshear J. L., McBride R., Kronmal R. A., Halperin J. L., Hart R. G., *Journal of the American College of Cardiology* 20(3):527-32, 1992; CAST, *N. Engl. J. Med.* 321:406, 1989; Nattel S., *Cardiovascular Research.* 37(3):567-77, 1998). Conversion rates for Class I antiarrhythmics range between 50-90% (Nattel S., Hadjis T., Talajic M., *Drugs* 48(3):345-71, 1994; Steinbeck G., Remp T., Hoffmann E., *Journal of Cardiovascular Electrophysiology.* 9(8 Suppl):S104-8, 1998). Class III antiarrhythmics appear to be more effective for terminating atrial flutter than for AF and are generally regarded as less effective than Class I drugs for terminating of AF (Nattel S., Hadjis T., Talajic M., *Drugs.* 48(3):345-71, 1994; Capucci A., Aschieri D., Villani G. Q., *Drugs & Aging* 13(1):51-70, 1998). Examples of such drugs include ibutilide, dofetilide and sotalol. Conversion rates for these drugs range between 30-50% for recent onset AF (Capucci A., Aschieri D., Villani G. Q., *Drugs & Aging* 13(1): 51-70, 1998), but they are also associated with a risk of inducing the ventricular tachyarrhythmias known as torsades de pointes. For ibutilide, the risk of ventricular proarrhythmia is estimated at ~4.4%, with ~1.7% of patients requiring cardioversion for refractory ventricular arrhythmias (Kowey P. R., VanderLugt J. T., Luderer J. R., *American Journal of Cardiology* 78(8A):46-52, 1996). Such events are particularly tragic in the case of AF as this arrhythmia is rarely a fatal in and of itself.

Therefore, there is a need in the art to identify new antiarrhythmic treatments, for both ventricular arrhythmias as well as for atrial arrhythmias. The present invention fulfills this need, and further provides other related advantages.

BRIEF SUMMARY OF THE INVENTION

As disclosed within the present invention, a variety of cardiac pathological conditions may be treated and/or prevented by the use of one or more ion channel modulating compounds that either singly or together with one or more additional compounds are able to selectively inhibit certain combination of cardiac ionic currents. More specifically, the cardiac currents referred to above are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The cardiac pathological conditions that may be treated and/or prevented by the present invention may include, but are not limited to, arrhythmias such as the various types of atrial and ventricular arrhythmias.

In one embodiment, the present invention provides ion channel modulating compounds that can be used to selectively inhibit cardiac early repolarising currents and cardiac sodium currents.

In another embodiment, the present invention provides ion channel modulating compounds that can be used to selectively inhibit cardiac early repolarising currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation.

In another embodiment, the present invention provides aminocyclohexyl ether compounds of formula (I), or a solvate or pharmaceutically acceptable salt thereof:

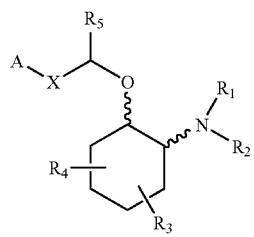
(I)

wherein, independently at each occurrence,

X is selected from a direct bond, —C($R_6$, $R_{14}$)—Y— and —C($R_{13}$)=CH—, with the proviso that when X is a direct bond and A is formula (III) then at least one of $R_7$, $R_8$ and $R_9$ is not hydrogen;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (I), form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]-hexan-3-yl and 3-azabicyclo[3.2.0]heptan-3-yl;

$R_3$ and $R_4$ are independently attached to the cyclohexane ring shown in formula (I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

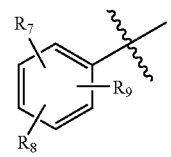
(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$, $R_{16}$) where $R_{15}$ and $R_{16}$ are independently selected from hydrogen, acetyl, methanesulfonyl and $C_1$-$C_6$alkyl;

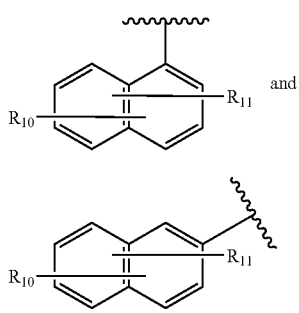

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15}, R_{16})$ where $R_{15}$ and $R_{16}$ are independently selected from hydrogen, acetyl, methanesulfonyl, and $C_1$-$C_6$alkyl;

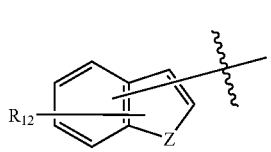

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15}, R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

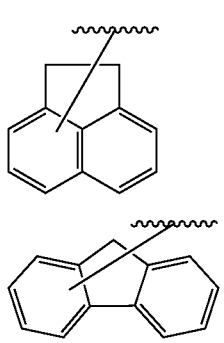

including isolated enantiomeric, diastereomeric and geometric isomers thereof, and mixtures thereof.

In other embodiments, the present invention provides a composition or medicament that includes a compound according to formula (I) in combination with a pharmaceutically acceptable carrier, diluent or excipient, and further provides a method for the manufacture of a composition or medicament that contains a compound according to formula (I).

In other embodiments, the present invention provides pharmaceutical compositions that contain at least one compound of formula (I) in an amount effective to treat a disease or condition in a warm-blooded animal suffering from or having the disease or condition, and/or prevent a disease or condition in a warm-blooded animal that would otherwise occur, and further contains at least one pharmaceutically acceptable carrier, diluent or excipient. The invention further provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. The diseases and conditions to which the compounds, compositions and methods of the present invention have applicability are as follows: arrhythmia, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other metal disorder, and alopecia.

In another embodiment, the present invention provides a pharmaceutical composition containing an amount of a compound of formula (I) effective to produce local analgesia or anesthesia in a warm-blooded animal in need thereof, and a pharmaceutically acceptable carrier, diluent, or excipient. The invention further provides a method for producing, local analgesia or anesthesia in a warm-blooded animal which includes administering to a warm-blooded animal in need thereof an effective amount of a compound of formula (I) or a pharmaceutical composition containing a compound of formula (I). These compositions and methods may be used to relieve or forestall the sensation of pain in a warm-blooded animal.

In another embodiment, the present invention provides a pharmaceutical composition containing an amount of a compound of formula (I) effective to enhance the libido in a warm-blooded animal in need thereof, and a pharmaceutically acceptable carrier, diluent, or excipient. The invention further provides a method for enhancing libido in a warm-blooded animal which includes administering to a warm-blooded animal in need thereof an effective amount of a compound of formula (I) or a pharmaceutical composition containing a compound of formula (I). These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

In another embodiment, the present invention provides a compound of formula (I) or composition containing a compound of formula (I), for use in methods for either modulating ion channel activity in a warm-blooded animal or for modulating ion channel activity in vitro.

These and other embodiments of the present invention will become evident upon reference to the following drawings and detailed description.

DETAILED DESCRIPTION OF THE INVENTION

Figure 1:
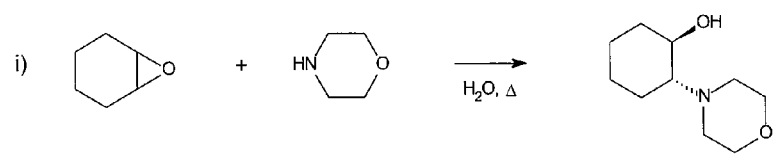
FIG. 1 illustrates the reaction sequence further described in Example 1, for preparing an aminocyclohexyl ether compound of the present invention.
Figure 1:
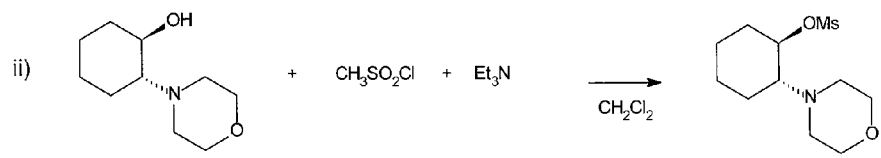
Figure 1:
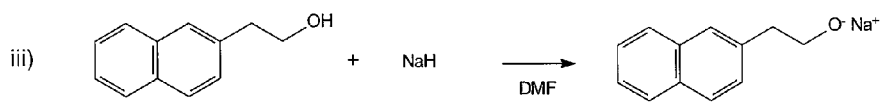
Figure 1:
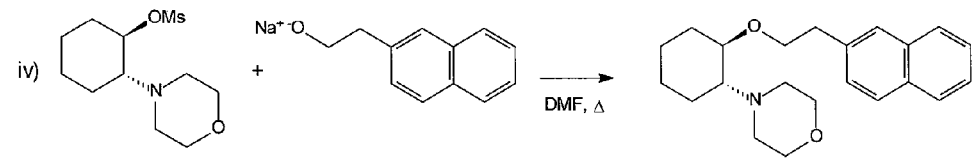

As briefly noted above, in one aspect the present invention provides for the treatment and/or prevention of a variety of cardiac pathological conditions by the use of one or more ion channel modulating compounds that either singly, or together with one or more additional compounds, are able to inhibit selective cardiac ionic currents. More specifically, the cardiac currents referred to above are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current ($I_{to1}$ such as Kv4.2 and Kv4.3), and the ultrarapid delayed rectifier current ($I_{Kur}$ such as Kv1.5, Kv1.4, and Kv2.1). The ultrarapid delayed rectifier current ($I_{Kur}$) has also been described as $I_{sus}$. A second calcium dependent transient outward current ($I_{to2}$) has also been described.

The cardiac pathological conditions that may be treated and/or prevented by the novel methods of the present invention may include, but are not limited to, arrhythmias such as the various types of atrial (supraventricular) and ventricular arrhythmias. The compounds of the present invention are especially useful in treating and/or preventing atrial fibrillation and ventricular fibrillation.

The novel methods of the present invention are especially useful under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation (Janse & Wit, *Physiol. Rev.* 69(4):1049-169, October 1989), and those conditions that precede the onset of arrhythmias such as atrial fibrillation (Pichlmaier et al. *Heart* 80(5):467-72, November 1998). Under conditions described above for cardiac arrhythmias in general, there is an increase in acidity of the cardiac milieu from the normal physiological pH (i.e., the pH of the milieu is lower than normal).

In the novel methods of the present invention of treating and/or preventing arrhythmia, one or more ion channel modulating compounds, either singly or together, are used to inhibit selective cardiac sodium currents and cardiac early repolarising currents. It is preferable that the ion channel modulating compounds generally have a pKa value of about 4 to 9 and more preferably less than about 8. The most preferred pKa values are between about 5 and 7.5. Methods to determine pKa values are well known in the art (see, e.g., Perrin, "Dissociation Constants of Organic Bases in Aqueous Solution", Butterworth, London, 1972). For compounds of the present invention with a preferred pKa value, the fraction of the charged (protonated) species will be increased under the pathological conditions such as cardiac arrhythmias and the presence of an arrhythmogenic substrate in the heart as described above due to the increase in cardiac milieu acidity. Where the charged form of a compound is active, its potency increases under conditions associated with an increases in cardiac milieu acidity.

In other methods of the present invention of treating and/or preventing arrhythmia, one or more ion channel modulating compounds, either singly or together with one or more additional compounds, are used to inhibit selective cardiac ionic currents. More specifically, the cardiac currents referred to above are the sodium currents and early repolarising currents. It is preferable that the ion channel modulating compounds block the said cardiac currents from extracellular loci. Such compounds act on an external locus of the ion channel that is accessible from the extracellular surface. This facilitates access to the ion channel and provides rapid onset kinetics and exhibits frequency dependent blockade of currents. Such properties are all beneficial for compounds used to treat arrhythmias.

The novel methods of the present invention provide treatment and/or prevention of arrhythmias that do not prolong action potential duration in normal cardiac ventricle but rather prolongs action potential duration under conditions when an arrhythmogenic substrate is present in the heart. Blockade of early, rather than late repolarising currents will prolong action potential duration under conditions where action potential duration has been previously reduced. Blockade of early, rather than late, repolarising currents offers another advantage over existing methods. Blockade of late repolarising currents such as $I_{Kr}$ (HERG) and $I_{KS}$ (minK-LQT) prolongs action potential under normal conditions. In so doing there is a risk of precipitating a polymorphic ventricular tachycardia commonly called torsade de pointes which can be fatal (Nattel, 1998). As blockade of early repolarising currents does not prolong action potential duration under normal conditions, the novel methods of the present invention greatly reduce such proarrhythmia risk.

Methods for in vitro assessment of inhibition activity of ion channel modulating compounds on different cardiac ion currents are well known in the art and are briefly described in Example 33 below.

Methods for assessment of proarrhythmia (e.g., torsade de pointes) risk of ion channel modulating compounds are also published in the literature and are briefly described in Example 34 below.

In the novel methods of the present invention of treating and/or preventing arrhythmia, one or more ion channel modulating compounds, either singly or together, are used to inhibit selective cardiac sodium currents and cardiac early repolarising currents. The concentration of each compound is typically between 0.001 and 30 μM.

Thus, the present invention is directed to ion channel modulating compounds that block cardiac early repolarising currents and cardiac sodium currents. The ion channel modulating compounds block the cardiac ion channels responsible for early repolarising currents and sodium currents; and/or block cardiac early repolarising currents and cardiac sodium currents under conditions where an arrhythmogenic substrate is present in the heart; and/or block the cardiac ion channels responsible for early repolarising currents and sodium currents under conditions where an arrhythmogenic substrate is present in the heart; and/or block cardiac early repolarising currents and cardiac sodium currents from extracellular loci in cardiac cells; and/or have pKa values of between 4-9, preferably having have pKa values of between 5-7.5.

In one embodiment, the cardiac early repolarising currents referred to above comprise ionic currents which activate rapidly after depolarization of membrane voltage and which effect repolarisation of the cell. The early repolarising currents may comprise the cardiac transient outward potassium current ($I_{to}$) and/or the ultrarapid delay rectifier current ($I_{Kur}$). The cardiac transient outward potassium current ($I_{to}$) and/or the ultrarapid delay rectifier current ($I_{Kur}$) may comprise at least one of the Kv4.2, Kv4.3, Kv2.1, Kv1.4 and Kv1.5 currents.

The invention also provides a composition comprising one or more of the above-described ion channel modulating compounds in combination with a pharmaceutically acceptable carrier, excipient or diluent.

The present invention provides that the above-described ion channel modulating compound(s) and/or composition(s) containing same may be used in a method for treating or preventing arrhythmia in a warm-blooded animal; and/or may be used in a method for modulating ion channel activity in a warm-blooded animal; and/or may be used in a method for modulating ion channel activity in vitro.

The invention also provides for the use of an ion channel modulating compound in a manufacture of a medicament.

The invention further provides a pharmaceutical composition comprising (a) an amount of an ion modulating compound as described above effective to treat or prevent atrial arrhythmia in a warm-blooded animal in need of the treatment or prevention, and (b) a pharmaceutically acceptable carrier, diluent, or excipient. According to the present invention, this composition may be used in a method for treating or preventing atrial arrhythmia in a warm-blooded animal, where the method comprises administering to a warm-blooded animal in need thereof a therapeutically effective amount of one of the above-described ion channel modulating compounds or a composition containing same.

The invention further provides a pharmaceutical composition comprising (a) an amount of an ion channel modulating compound as described above effective to treat or prevent ventricular arrhythmia in a warm-blooded animal in need of the treatment or prevention, and (b) a pharmaceutically acceptable carrier, diluent, or excipient. This composition may be used in a method for treating or preventing ventricular arrhythmia in a warm-blooded animal, where the method comprises administering to a warm-blooded animal in need thereof a therapeutically effective amount of one of the above-described ion channel modulating compounds or a composition containing same.

The invention further provides a method for inhibiting multiple cardiac ionic current, where the method comprises administering to a warm-blooded animal in need thereof one or more compounds that either singly or together both block cardiac early repolarising currents and cardiac sodium currents, said one or more compounds being administered in an amount effective to block cardiac sodium currents and cardiac early repolarising currents. In this method, said one or more compounds may either singly or together both block cardiac early repolarising currents and cardiac sodium currents from extracellular loci in cardiac cells.

The present invention also provides a method for inhibiting multiple cardiac ionic currents, where the method comprises administering to a warm-blooded animal in need thereof one or more compounds that either singly or together both block the cardiac ion channels responsible for early repolarising currents and sodium channels, said one or more compounds being administered in an amount effective to block the cardiac sodium ion channels and the cardiac early repolarising ion channels. In this method, said one or more compounds may either singly or together both block cardiac ion channels responsible for early repolarising currents and sodium currents from extracellular loci in cardiac cells. Also in this method one compound may block both sodium currents and cardiac early repolarising currents from extracellular loci in cardiac cells. Also in these methods, each of said one or more compounds may have a pKa value of less than 8.

The invention in addition provides a method for treating or preventing a cardiac condition wherein there is an "arrhythmogenic substrate" present in the heart, where the method comprises administering to a warm-blooded animal in need thereof, in an amount effective to treat or prevent said cardiac condition, one or more compounds that either singly or together block cardiac early repolarising currents and cardiac sodium currents. In this method, said one or more compounds may either singly or together both block cardiac early repolarising currents and cardiac sodium currents from extracellular loci in cardiac cells. Also in this method, one compound may both block cardiac early repolarising currents and cardiac sodium currents from extracellular loci in cardiac cells. Also in these methods, each of said one or more compounds may have a pKa value of less than 8.

Furthermore, the present invention provides a method for treating or preventing a cardiac condition wherein there is an "arrhythmogenic substrate" present in the heart, where this method comprises administering to a warm-blooded animal in need thereof, in an amount effective to treat or prevent said cardiac condition, one or more compounds that either singly or together both block cardiac ion channels responsible for early repolarising currents and sodium currents. In this method, said one or more compounds may either singly or together both block cardiac ion channels responsible for early repolarising currents and sodium currents from extracellular loci in cardiac cells. Also in this method, one compound may both block cardiac ion channels responsible for early repolarising currents and sodium currents from extracellular loci in cardiac cells. Additionally in this method, each of said one or more compounds may have a pKa value of less than 8.

The present invention provides a method for treating or preventing a cardiac condition wherein there is an increase in acidity from the normal physiological pH of the cardiac milieu, where the method comprises administering to a warm-blooded animal in need thereof, in an amount effective to treat or prevent said cardiac condition, one or more compounds that either singly or together both block cardiac early repolarising currents and cardiac sodium currents. In this method, said one or more compounds may either singly or together both block cardiac ion channels responsible for early repolarising currents and sodium currents from extracellular loci in cardiac cells. Also in this method, one compound may block cardiac ion channels responsible for early repolarising currents and in addition block sodium currents from extracellular loci in cardiac cells. In this method, each of said one or more compounds may have a pKa value of less than 8.

The present invention also provides a method for treating or preventing a cardiac condition wherein there is an increase in acidity from the normal physiological pH of the cardiac milieu, where the method comprises administering to a warm-blooded animal in need thereof, in an amount effective to treat or prevent said cardiac condition, one or more compounds that either singly or together both block cardiac ion channels responsible for early repolarising currents and sodium currents. In this method, said one or more compounds may either singly or together both block cardiac ion channels responsible for early repolarising currents and sodium currents from extracellular loci in cardiac cells. Also in this method, one compound may both block cardiac ion channels responsible for early repolarising currents and sodium currents from extracellular loci in cardiac cells. Additionally, in this method, each of said one or more compounds may have a pKa value of less than 8.

In a preferred embodiment, in the above-described methods, the cardiac condition is ventricular arrhythmia. In another preferred embodiment, in the above-described methods, the cardiac condition is atrial arrhythmia. In some instances, the increase in acidity of the cardiac milieu is due to myocardial ischaemia. Additionally, or alternatively, the increase in acidity of the cardiac milieu is due to high heart rate. Additionally, or alternatively, the increase in acidity is due to inflammation. Additionally, or alternatively, the increase in acidity is due to the presence of an "arrhythmogenic substrate" in the heart. Additionally, or alternatively, the increase in acidity is due to conditions which precede atrial fibrillation.

In another aspect, the present invention is directed to aminocyclohexyl ether compounds, pharmaceutical compositions containing the aminocyclohexyl ether compounds, and various uses for the compound and compositions. Such uses include blockage of ion channels in vitro or in vivo, the treatment of arrhythmias, the production of anesthesia, and other uses as described herein. An understanding of the present invention may be aided by reference to the following definitions and explanation of conventions used herein.

Definitions and Conventions

The aminocyclohexyl ether compounds of the invention have an ether oxygen atom at position 1 of a cyclohexane ring, and an amine nitrogen atom at position 2 of the cyclohexane ring, with other positions numbered in corresponding order as shown below in structure (A):

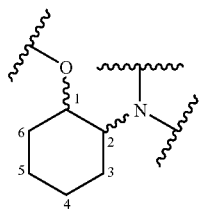

(A)

The bonds from the cyclohexane ring to the 1-oxygen and 2-nitrogen atoms in the above formula may be relatively disposed in either a cis or trans relationship. In a preferred embodiment of the present invention, the stereochemistry of the amine and ether substituents of the cyclohexane ring is either (R,R)-trans or (S,S)-trans. In another preferred embodiment the stereochemistry is either (R,S)-cis or (S,R)-cis.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of the invention containing the A-X—CH($R_5$)— group where A equals formula (III)

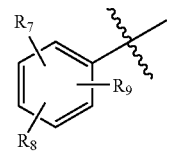

(III)

are intended to encompass compounds having the group (B):

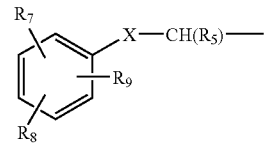

(B)

where the group (B) is intended to encompass groups wherein any ring atom that could otherwise be substituted with hydrogen, may instead be substituted with either $R_7$, $R_8$ or $R_9$, with the proviso that each of $R_7$, $R_8$ and $R_9$ appears once and only once on the ring. Ring atoms that are not substituted with any of $R_7$, $R_8$ or $R_9$ are substituted with hydrogen. In those instances where the invention specifies that a non-aromatic ring is substituted with more than one R group, and those R groups are shown connected to the non-aromatic ring with bonds that bisect ring bonds, then the R groups may be present at different atoms of the ring, or on the same atom of the ring, so long as that atom could otherwise be substituted with a hydrogen atom.

Likewise, where the invention specifies compounds containing the A-X—CH($R_5$)— group where A equals the aryl group (VI)

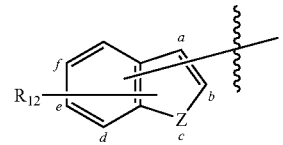

(VI)

the invention is intended to encompass compounds wherein —X—CH($R_5$)— is joined through X to the aryl group (VI) at any atom which forms the aryl group (VI) so long as that atom of group (VI) could otherwise be substituted with a hydrogen atom. Thus, there are seven positions (identified with the letters "a" through "g") in structure (VI) where the —X—CH($R_5$)— group could be attached, and it is attached at one of those seven positions. The $R_{12}$ group would occupy one and only one of the remaining six positions, and hydrogen atoms would be present in each of the five remaining positions. It is to be understood that when Z represents a divalent atom, e.g., oxygen or sulfur, then Z cannot be directly bonded to —X—CH($R_5$)—.

When the invention specifies the location of an asymmetric divalent radical, then that divalent radical may be positioned in any possible manner that provides a stable chemical structure. For example, for compounds containing the A-X—CH ($R_5$)— group where X is C($R_{14}$, $R_6$)—Y—, the invention provides compounds having both the A-C($R_{14}$, $R_6$)—Y—CH ($R_5$)— and A-Y—C($R_{14}$, $R_6$)—CH($R_5$)— groups.

A wavy bond from a substituent to the central cyclohexane ring indicates that that group may be located on either side of the plane of the central ring.

The compounds of the present invention contain at least two asymmetric carbon atoms and thus exist as enantiomers and diastereomers. Unless otherwise noted, the present invention includes all enantiomeric and diastereomeric forms of the aminocyclohexyl ether compounds of the invention. Pure stereoisomers, mixtures of enantiomers and/or diastereomers, and mixtures of different compounds of the invention are included within the present invention. Thus, compounds of the present invention may occur as racemates, racemic mixtures and as individual diastereomers, or enantiomers with all isomeric forms being included in the present invention. A racemate or racemic mixture does not imply a 50:50 mixture of stereoisomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard the identity of the other member of the set. However, combinations of substituents and/or variables are permissible only if such combinations result in stable compounds.

In accordance with the present invention and as used herein, the following terms are defined to have following meanings, unless explicitly stated otherwise:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C=O)— group containing the specified number of carbon atoms. Examples include acetyl [$CH_3C$=O—, a $C_2$acyl] and propionyl [$CH_3CH_2C$=O—, a $C_3$acyl].

"Alkanoyloxy" refers to an ester substituent wherein the ether oxygen is the point of attachment to the molecule. Examples include propanoyloxy [($CH_3CH_2C$=O—O—, a $C_3$alkanoyloxy] and ethanoyloxy [$CH_3C$=O—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to a alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2OC$=O—, a $C_3$alkoxycarbonyl] and methoxycarbonyl [$CH_3OC$=O—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing an hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be blocked, so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of formula (I)" encompass compositions that contain more than one compound of formula (I).

Compounds of the Present Invention

The compounds of the present invention are amines which may be represented by formula (I):

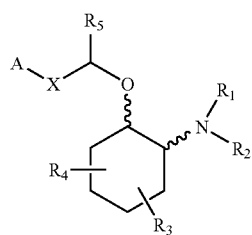

(I)

Compounds of formula (I) are aminocyclohexyl ethers. More specifically, these aminocyclohexyl ethers are substituted at position 2 of the cyclohexyl ring with an amine group —NR$_1$R$_2$. The cyclohexyl ring may also be substituted with additional substituents (designated as R$_3$ and R$_4$) as described in more detail below. Examples of specific embodiments of compounds represented by formula (I) are described below Depending upon the selection of substituents R$_1$ and R$_2$, the compounds of formula (I) may be primary, secondary, or tertiary amines (i.e., both R$_1$ and R$_2$ are hydrogen, only one of R$_1$ and R$_2$ is hydrogen, or neither of R$_1$ and R$_2$ are hydrogen, respectively). In one embodiment of the invention, the compounds of formula (I) are tertiary amines, i.e., neither R$_1$ nor R$_2$ is hydrogen. Where the amine is tertiary, it may be a cyclic amine. Amine substituents R$_1$ and R$_2$ may be independently selected from substituents which include hydrogen, alkyl groups containing from one to eight carbon atoms (i.e., $C_1$-$C_8$alkyl), alkoxyalkyl groups containing from three to eight carbon atoms (i.e., $C_3$-$C_8$alkoxyalkyl), alkyl groups containing from one to eight carbon atoms where one of the carbon atoms is substituted with a hydroxyl group (i.e., $C_1$-$C_8$hydroxyalkyl), and aralkyl groups containing from seven to twelve carbon atoms (i.e., $C_7$-$C_{12}$aralkyl).

Alternatively, R$_1$ and R$_2$, when taken together with the nitrogen atom to which they are directly attached in formula (I), may form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, R$_1$ and R$_2$, when taken together with the 2-amino nitrogen of formula (I), may complete a bicyclic ring. Bicyclic rings include, for example, 3-azabicyclo[3.2.2] nonane, 2-azabicyclo[2.2.2]octane, 3-azabicyclo[3.1.0]hexane, and 3-azabicyclo[3.2.0]heptane. For these derivatives, the 2-substituents of the cyclohexyl ethers of formula (I) are the following groups: 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]-heptan-3-yl.

Preferably, R$_1$ and R$_2$, when taken together, contain only a single heteroatom. Preferred heteroatoms include nitrogen, oxygen and sulfur. An example of a ring in which R$_1$ and R$_2$ together include an oxygen heteroatom is the morpholinyl group. An example of a ring where R$_1$ and R$_2$ together include a second nitrogen heteroatom is the piperazinyl group.

Cyclohexane substituents R$_3$ and R$_4$ may be independently attached to ring positions 3, 4, 5 or 6 (i.e., both R$_3$ and R$_4$ may be attached to the same ring position or each attached to different ring positions). $R_3$ and $R_4$ are independently selected from hydrogen, hydroxy, $C_1$-$C_6$alkyl, and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the ether side chain, —CH($R_5$)—X-A, in formula (I) may take several forms. For example, a compound of formula (J) may have X as a —C($R_6$, $R_{14}$)—Y— group, where Y may be any of a direct bond, an oxygen atom (O), a sulfur atom (S) or a $C_1$-$C_4$alkylene group. $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl. Thus, compounds of the invention include compounds of formula (I) where $R_6$ and $R_{14}$ are hydrogen and Y is a direct bond, such that X may be $CH_2$.

Alternatively, X may be an alkenylene moiety, e.g., a cis- or trans-alkenylene moiety, C($R_{13}$)=CH, where $R_{13}$ may be any of hydrogen, $C_1$-$C_6$alkyl, $C_3$-$C_8$cycloalkyl, aryl or benzyl. For compounds of formula (I) where X is an alkenylene moiety, X is preferably a trans-alkenylene moiety.

Alternatively, X may be a direct bond. Independent of the selections for A, X and other variables, $R_5$ is selected from hydrogen, $C_1$-$C_6$alkyl, aryl and benzyl.

In one embodiment of the present invention, X is either a —C($R_6$, $R_{14}$)—Y— or a C($R_{13}$)=CH group, and is not a direct bond. In another embodiment, the compounds of the invention exclude those compounds wherein X is a direct bond when $R_1$ and $R_2$ are hydrogen. In another embodiment, X is selected from a direct bond, —C($R_6$, $R_{14}$)—Y—, and —C($R_{13}$)=CH—, with the proviso that when X is a direct bond and A is formula (III) then at least one of $R_7$, $R_8$ and $R_9$ is not hydrogen. In another embodiment, the compounds of the invention exclude those compounds wherein X is a direct bond when A is formula (III) and each of $R_7$, $R_8$ and $R_9$ is hydrogen. In another embodiment, the compounds of the invention exclude those compounds wherein X is a direct bond when A is formula (III).

Ether side chain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$-$C_{12}$alkyl and $C_3$-$C_{13}$carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII) respectively.

A suitable "A" group within the compounds of the present invention is a phenyl ring represented by formula (III):

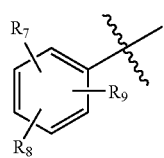

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, aryl and N($R_{15}$, $R_{16}$) where $R_{15}$ and $R_{16}$ are independently selected from hydrogen, acetyl, methanesulfonyl, and $C_1$-$C_6$alkyl.

For compounds of formula (I) where X is a direct bond or $CH_2$, at least one of $R_7$, $R_8$ and $R_9$ is preferably selected from amine (—$NR_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl, $C_1$-$C_6$thioalkyl or aryl groups. For compounds of formula (I) when X is CH=CH, and $R_3$ and $R_4$ are hydrogen, at least one of $R_7$, $R_8$ and $R_9$ is preferably a substituent other than hydrogen. In one embodiment, the present invention provides compounds of formula (J) where A includes phenyl groups of formula (III) such that at least one of $R_7$, $R_8$ and $R_9$ is not hydrogen, i.e., formula (III) is a phenyl group that contains at least one non-hydrogen substituent. In another embodiment, $R_7$, $R_8$ and $R_9$ are selected from amine (—$NR_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl and $C_1$-$C_6$thioalkyl, i.e., none of $R_7$, $R_8$ or $R_9$ is aryl. In another embodiment, A does not include a phenyl ring of formula (III) when X is a direct bond.

Other suitable "A" groups in compounds of the present invention are 1-naphthyl groups as represented by formula (IV):

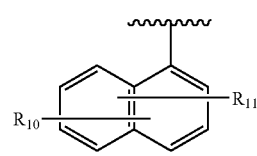

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$, $R_{16}$) where $R_{15}$ and $R_{16}$ are independently selected from hydrogen, acetyl, methanesulfonyl, and $C_1$-$C_6$alkyl.

Other suitable "A" groups in compounds of the present invention are 2-naphthyl group as represented by formula (V):

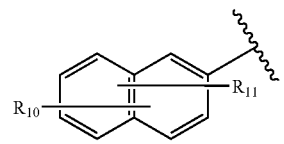

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15}, R_{16})$ where $R_{15}$ and $R_{16}$ are independently selected from hydrogen, acetyl, methanesulfonyl, and $C_1$-$C_6$alkyl, as defined above.

Other suitable "A" groups in compounds of the present invention are aromatic groups represented by formula (VI):

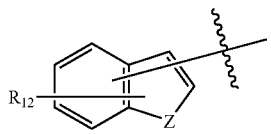

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15}, R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is O, and thianaphthene where Z is S. As described below, in a preferred embodiment, Z is O, S or N—$R_{17}$, and in a particularly preferred embodiment Z is O or S.

Another suitable "A" group in compounds of the present invention are acenaphthyl groups as represented by formula (VII):

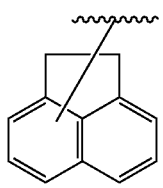

(VII)

Still another suitable "A" group in compounds of the present invention is the fluorenyl group represented by formula (VIII):

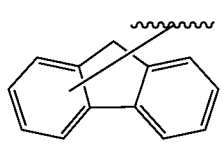

(VIII)

Preferably, ether side chain component A is an acenaphthyl or fluorenyl group only when X is a direct bond or $CH_2$. In further preferred embodiments, the acenaphthyl group is a 1-acenaphthyl group, and the fluorenyl group is a 9-fluorenyl group.

As mentioned above, the present invention provides aminocyclohexyl ethers represented by formula (I). In a preferred embodiment X is $(CH_2)$—Y. For these embodiments, Y is preferably a direct bond, an oxygen atom, or a sulfur atom. In a particularly preferred embodiment, Y is a direct bond or an oxygen atom. In another preferred embodiment Y is a direct bond and X is $C(R_6, R_{14})$, where $R_6$ and $R_{14}$ are as defined above. In another preferred embodiment, where X is $C(R_{13})$=CH, $R_{13}$ is a hydrogen atom. For these embodiments, $R_3$ and $R_4$ are preferably independently attached to the cyclohexane ring at the 4- or 5-positions.

In a preferred embodiment, the invention provides compounds having formula (IX), or a solvate or pharmaceutically acceptable salt thereof:

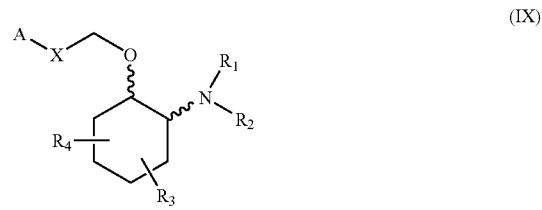

(IX)

wherein, independently at each occurrence,

X is selected from a direct bond, —CH=CH— and —$C(R_6, R_{14})$—Y—;

Y is selected from a direct bond, O and S; and $R_1$, $R_2$, $R_3$, $R_4$, $R_6$, $R_7$, $R_8$, $R_9$, $R_{10}$, $R_{11}$, $R_{12}$, $R_{14}$, A and Z are defined as above for compounds of formula (I).

In another preferred embodiment, the invention provides a compound having formula (X), or a solvate or pharmaceutically acceptable salt thereof:

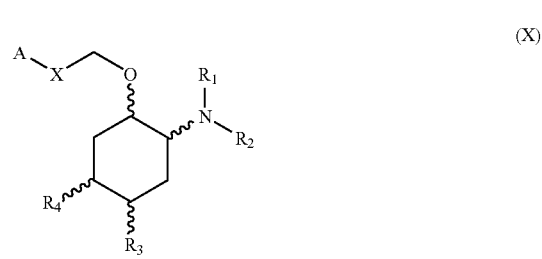

(X)

wherein, independently at each occurrence,

X is selected from a direct bond, —CH=CH— and —$C(R_6, R_{14})$—Y—;

Y is selected from a direct bond, O, and S;

$R_1$, $R_2$, $R_6$ and $R_{14}$ are defined as above for compounds of formula (I);

$R_3$ and $R_4$ are independently attached to the cyclohexane ring at the 4- or 5-positions, and are independently selected from hydrogen and $C_1$-$C_6$alkoxy; and A is selected from $C_5$-$C_{12}$alkyl, $C_3$-$C_8$cycloalkyl, and any of formulae (III), (IV), (V), and (VI) as above for compounds of formula (I), wherein Z, $R_7$, $R_8$, $R_9$, $R_{10}$, $R_{11}$ and $R_{12}$ are defined as above for compounds of formula (I).

In another preferred embodiment, the invention provides compounds having formula (XI), or a solvate or pharmaceutically acceptable salt thereof:

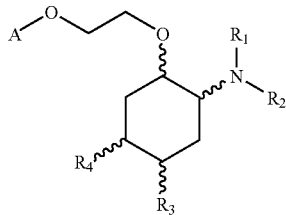

(XI)

wherein, independently at each occurrence, $R_1$ and $R_2$ are defined as above for compounds of formula (I);

$R_3$ and $R_4$ are independently attached to the cyclohexane ring at the 4- or 5-positions, and are independently selected from hydrogen and methoxy; and A is selected from $C_5$-$C_{12}$alkyl, $C_3$-$C_8$cycloalkyl, and any of formulae (III), (IV), (V), and (VI) as above for compounds of formula (I), wherein Z, $R_7$, $R_8$, $R_9$, $R_{10}$, $R_{11}$ and $R_{12}$ are defined as above for compounds of formula (I).

In another preferred embodiment, the invention provides compounds of formula (XII), or a solvate or pharmaceutically acceptable salt thereof:

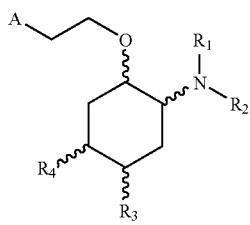

(XII)

wherein, independently at each occurrence, $R_1$ and $R_2$ are defined as above for compounds of formula (I);

$R_3$ and $R_4$ are independently attached to the cyclohexane ring at the 4- or 5-positions, and are independently selected from hydrogen and methoxy; and A is selected from $C_5$-$C_{12}$alkyl, $C_3$-$C_8$cycloalkyl, and any of formulae (III), (IV), (V), and (VI) as above for compounds of formula (I), wherein Z, $R_7$, $R_8$, $R_9$, $R_{10}$, $R_{11}$ and $R_{12}$ are defined as above for compounds of formula (I).

In another preferred embodiment, the invention provides compounds of formula (XIII), or a solvate or pharmaceutically acceptable salt thereof:

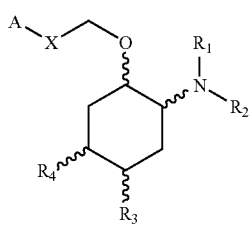

(XIII)

wherein, independently at each occurrence,

X is selected from —C($R_6$, $R_{14}$)—Y— and —CH=CH—;

Y, $R_1$, $R_2$, $R_6$ and $R_{14}$ are defined as above for compounds of formula (I);

$R_3$ and $R_4$ are independently attached to the cyclohexane ring at the 4- or 5-positions, and are independently selected from hydrogen and methoxy; and A is selected from $C_3$-$C_8$cycloalkyl and any of formulae (III), (IV), (V), (VI), (VII) and (VIII) as above for compounds of formula (I), where $R_8$ and $R_9$ are defined as above for compounds of formula (I); $R_7$, $R_{10}$, $R_{11}$ and $R_{12}$ are hydrogen, and Z is selected from O, S and N—$R_{17}$ where $R_{17}$ is selected from hydrogen and methyl.

In another preferred embodiment, the invention provides compounds having formula (XIV), or a solvate or pharmaceutically acceptable salt thereof:

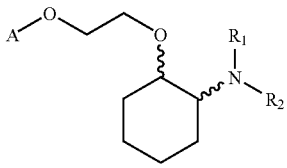

(XIV)

wherein, independently at each occurrence, $R_1$ and $R_2$ are defined as above for compounds of formula (I);

A is selected from any of formulae (III), (IV), (V) and (VI) as above for compounds of formula (I), wherein $R_7$, $R_{10}$, $R_{11}$, and $R_{12}$, are hydrogen, $R_8$ and $R_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and $NH_2$, with the proviso that at least one of $R_8$ and $R_9$ is not hydrogen; and Z is selected from O and S.

In another preferred embodiment, the invention provides compounds having formula (XV), or a solvate or pharmaceutically acceptable salt thereof:

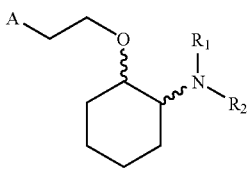

(XV)

wherein, independently at each occurrence, $R_1$ and $R_2$ are defined as above for compounds of formula (I); and A is selected from any of formulae (III), (IV), (V) and (VI) as defined above for compounds of formula (I), wherein $R_7$, $R_{10}$, $R_1$, and $R_{12}$, are hydrogen, $R_8$ and $R_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and $NH_2$, with the proviso that at least one of $R_8$ and $R_9$ is not hydrogen; and Z is selected from O and S.

In another preferred embodiment, the invention provides compounds having formula (XVI), or a solvate or pharmaceutically acceptable salt thereof:

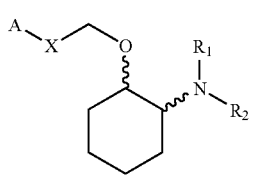

(XVI)

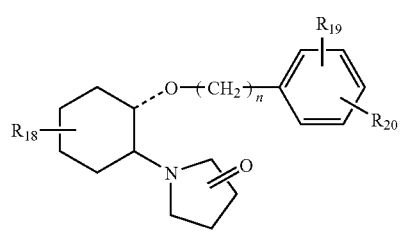

(XVIII)

wherein, independently at each occurrence,

X is selected from a direct bond, trans-CH=CH—, —CH$_2$— and —CH$_2$—O—;

R$_1$ and R$_2$ are both methoxyethyl or, when taken together with the nitrogen atom to which they are attached, complete a ring selected from pyrrolidinyl, 2-ketopyrrolidinyl, 3-ketopyrrolidinyl, 2-acetoxypyrrolidinyl, 3-acetoxypyrrolidinyl, 2-hydroxypyrrolidinyl, 3-hydroxypyrrolidinyl, thiazolidinyl, piperidinyl, 2-ketopiperidinyl, 3-ketopiperidinyl, 4-ketopiperidinyl, acetylpiperazinyl, 1,4-dioxa-7-azaspiro[4.4]non-7-yl, hexahydroazepinyl, morpholinyl, N-methylpiperazinyl and 3-azabicyclo[3.2.2]nonanyl; and A is selected from cyclohexyl, monochlorophenyl, 2,6-dichlorophenyl, 3,4-dichlorophenyl, 2-bromophenyl, 2,4-dibromophenyl, 3-bromophenyl, 4-bromophenyl, 3,4-dimethoxyphenyl, 1-naphthyl, 2-naphthyl, 3-benzo(b)thiophenyl, 4-benzo(b)thiophenyl, (2-trifluoromethyl)phenyl, 2,4-di(trifluoromethyl)phenyl, and (4-trifluoromethyl)phenyl.

In another preferred embodiment, the invention provides compounds having formula (XVII), or a solvate or pharmaceutically acceptable salt thereof:

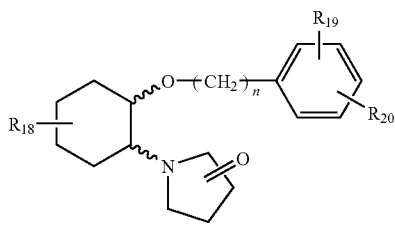

(XVII)

wherein, independently at each occurrence, n is selected from 1, 2 and 3;

R$_{18}$ is either hydrogen or methyl and is independently attached to the cyclohexane ring shown in formula (XVII) at one of the 3-, 4-, 5- or 6-positions;

R$_{19}$ is selected from a group consisting of bromine, chlorine, fluorine and hydrogen; and R$_{20}$ is selected from a group consisting of bromine, chlorine and fluorine;

including isolated enantiomeric, diastereomeric and geometric isomers thereof, and mixtures thereof.

In another preferred embodiment, the invention provides compounds having a trans configuration of formula (XVII) as represented by formula (XVIII), or a solvate or pharmaceutically acceptable salt thereof:

wherein, independently at each occurrence, n is selected from 1, 2 and 3;

R$_{18}$ is either hydrogen or methyl and is independently attached to the cyclohexane ring shown in formula (XVII) at one of the 3-, 4-, 5- or 6-positions;

R$_{19}$ is selected from a group consisting of bromine, chlorine, fluorine and hydrogen; and R$_{20}$ is selected from a group consisting of bromine, chlorine and fluorine;

including isolated enantiomeric, diastereomeric and geometric isomers thereof, and mixtures thereof.

In yet another preferred embodiment, the invention provides compounds having formula (IXX); or a solvate or pharmaceutically acceptable salt thereof:

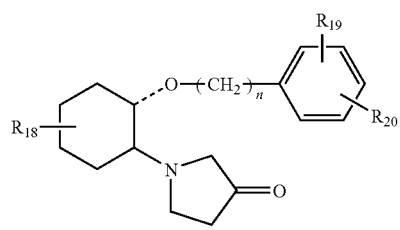

(IXX)

wherein, independently at each occurrence, n is selected from 1, 2 and 3;

R$_{18}$ is either hydrogen or methyl and is independently attached to the cyclohexane ring shown in formula (XVII) at one of the 3-, 4-, 5- or 6-positions;

R$_{19}$ is selected from a group consisting of bromine, chlorine, fluorine and hydrogen; and R$_{20}$ is selected from a group consisting of bromine, chlorine and fluorine;

including isolated enantiomeric, diastereomeric and geometric isomers thereof, and mixtures thereof.

The following are further preferred compounds of the present invention, including isolated enantiomeric and diastereomeric isomers thereof, and mixtures thereof; and pharmaceutically acceptable salts thereof:

(1R,2R)/(1S,2S)-[2-(4-morpholinyl)-1-(2-naphthenethoxy)]cyclohexane

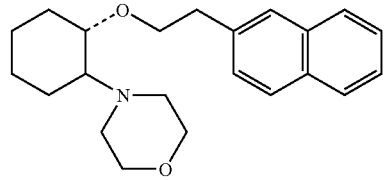

(1R,2R)/(1S,2S)-[2-(4-morpholinyl)-1-(1-naphthenethoxy)]cyclohexane

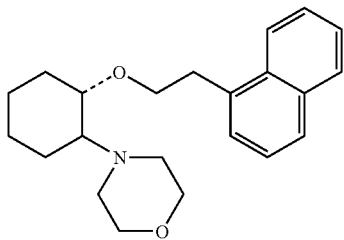

(1R,2R)/(1S,2S)-[2-(4-morpholinyl)-1-(4-bromophenethoxy)]cyclohexane

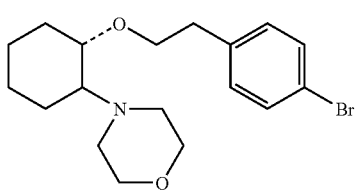

(1R,2R)/(1S,2S)-[2-(4-morpholinyl)-1-[2-(2-naphthoxy)ethoxy]]cyclohexane

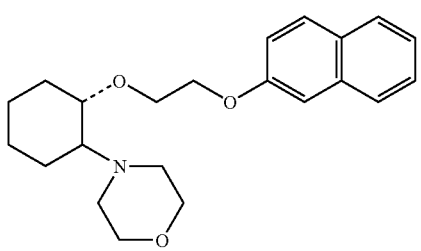

(1R,2R)/(1S,2S)-[2-(4-morpholinyl)-1-[2-(4-bromophenoxy)ethoxy]]cyclohexane

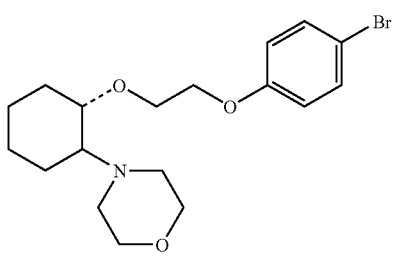

(1R,2R)/(1S,2S)-[2-(4-morpholinyl)-1-(3,4-dimethoxyphenethoxy)]cyclohexane

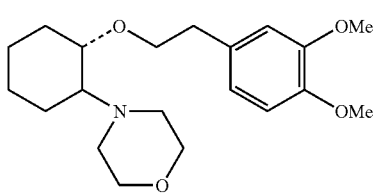

(1R,2R)/(1S,2S)-[2-(1-pyrrolidinyl)-1-(1-naphthenethoxy)]cyclohexane

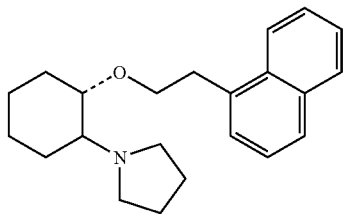

(1R,2R)/(1S,2S)-[2-(4-morpholinyl)-1-(2-(benzo[b]thiophen-3-yl)]cyclohexane

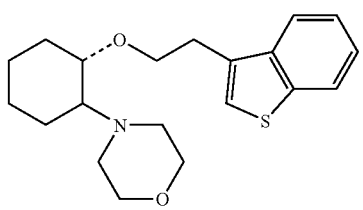

(1R,2R)/(1S,2S)-[2-(4-morpholinyl)-1-(2-(benzo[b]thiophen-4-yl)]cyclohexane

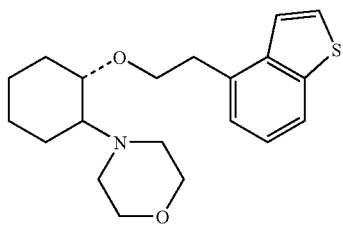

(1R,2R)/(1S,2S)-[2-(4-morpholinyl)-1-(3-bromophenethoxy)]cyclohexane

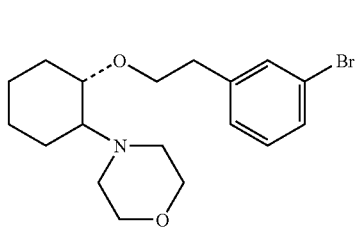

(1R,2R)/(1S,2S)-[2-(4-morpholinyl)-1-(2-bromophenethoxy)]cyclohexane

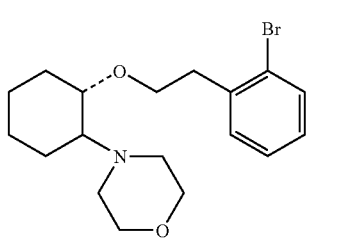

27

(1R,2R)/(1S,2S)-[2-(4-morpholinyl)-1-(3(3,4-dimethoxyphenyl)propoxy)]cyclohexane

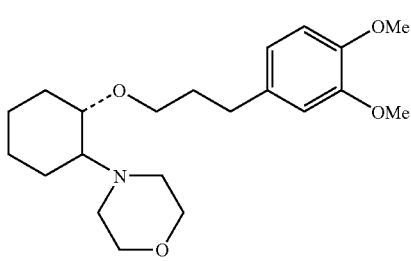

(1R,2R)/(1S,2S)-[2-[bis(2-methoxyethyl)aminyl]-1-(2-naphthenethoxy)]cyclohexane

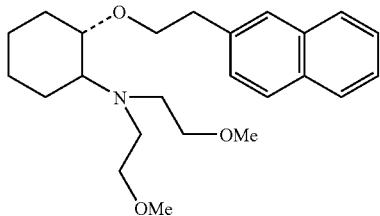

(1R,2R)/(1S,2S)-2-(4-morpholinyl)-1-(3,4-dichlorophenethoxy)cyclohexane

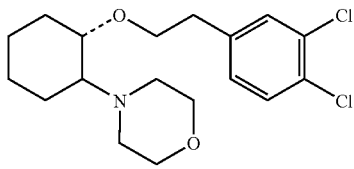

(1R,2R)/(1S,2S)-2-(3-ketopyrrolidinyl)-1-(1-naphthenethoxy)cyclohexane

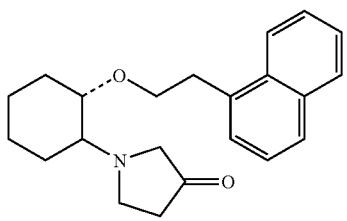

(1R,2R)/(1S,2S)-2-(1-acetylpiperazinyl)-1-(2-naphthenethoxy)cyclohexane

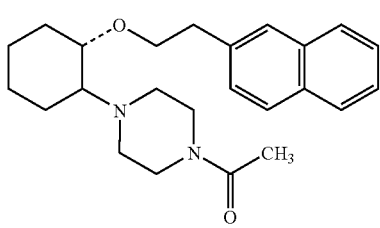

28

(1R,2R)/(1S,2S)-2-(3-ketopyrrolidinyl)-1-(2,6-dichlorophenethoxy)cyclohexane

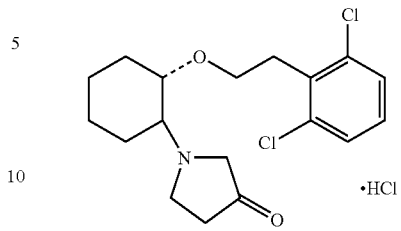

(1R,2R)/(1S,2S)-2-[1,4-dioxa-7-azaspiro[4.4]non-7-yl]-1-(1-naphthenethoxy)cyclohexane

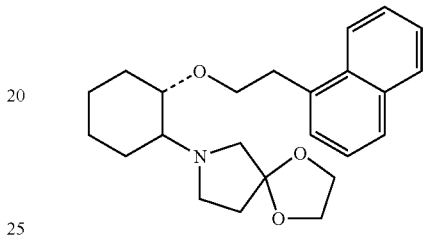

(1R,2S)/(1S,2R)-2-(4-morpholinyl)-1-[(2-trifluoromethyl)phenethoxy]cyclohexane monohydrochloride

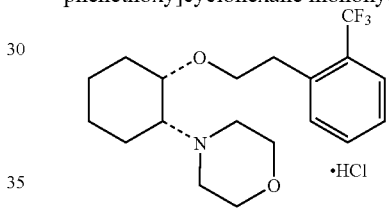

(1R,2R)/(1S,2S)-2-(3-ketopyrrolidinyl)-1-[3-(cyclohexyl)propoxy]cyclohexane monohydrochloride

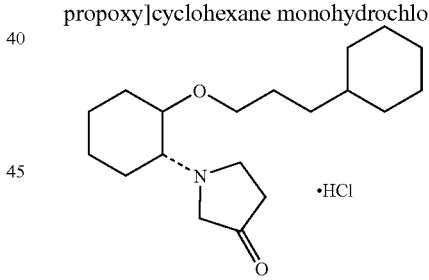

(1R,2R)/(1S,2S)-2-(3-acetoxypyrrolidinyl)-1-(1-naphthenethoxy)cyclohexane monohydrochloride

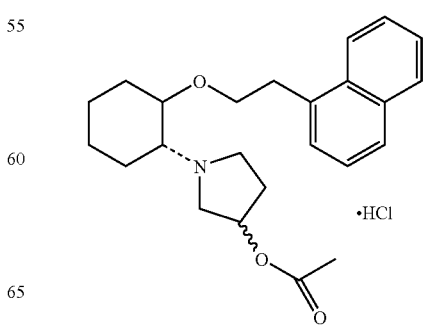

(1R,2R)/(1S,2S)-2-(4-morpholinyl)-1-[(2,6-dichlorophenyl)methoxy]cyclohexane monohydrochloride

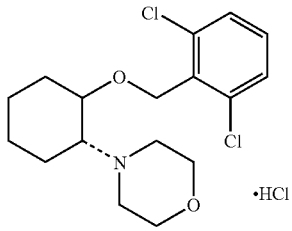

(1R,2R)/(1S,2S)-2-(3-ketopyrrolidinyl)-1-[(2,6-dichlorophenyl)methoxy]cyclohexane monohydrochloride

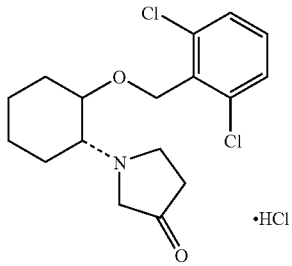

(1R,2R)/(1S,2S)-2-(3-hydroxypyrrolidinyl)-1-(2,6-dichlorophenethoxy)cyclohexane monohydrochloride

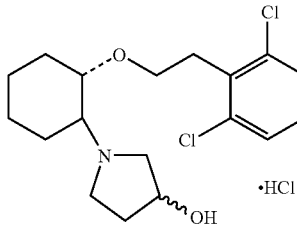

(1R,2R)/(1S,2S)-2-(3-ketopyrrolidinyl)-1-(2,2-diphenylethoxy)cyclohexane monohydrochloride

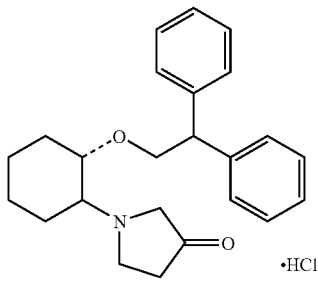

(1R,2R)/(1S,2S)-2-(3-thiazolidinyl)-1-(2,6-dichlorophenethoxy)cyclohexane monohydrochloride

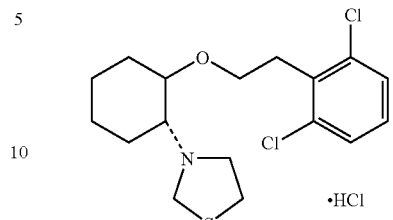

(1R,2S)/(1S,2R)-2-(3-ketopyrrolidinyl)-1-(1-naphthenethoxy)cyclohexane monohydrochloride

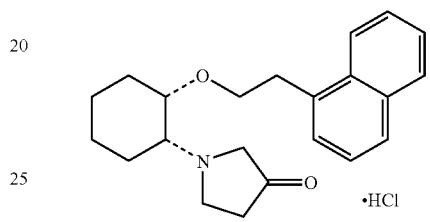

(1R,2R)/(1S,2S)-2-(3-hydroxypyrrolidinyl)-1-(3,4-dimethoxyphenethoxy)cyclohexane monohydrochloride

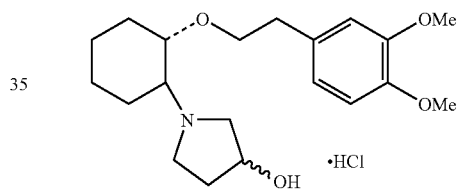

Outline of Method of Preparation of Compounds of the Invention

The aminocyclohexyl ether compounds of the present invention contain amino and ether sidechains disposed in a 1, 2 arrangement on a cyclohexane ring. Accordingly, the amino and ether sidechains may be disposed in either a cis or trans relationship, relative to one another and the plane of the cyclohexane ring. The present invention provides synthetic methodology whereby cis or trans compounds may be prepared.

Trans compounds of the present invention may be prepared in analogy with known synthetic methodology (see, e.g., Shanklin, Jr. et al., U.S. Pat. No. 5,130,309). FIG. 1 outlines the preparation of a trans compound of the invention, where this preparation is more fully described in Example 1. As outlined in FIG. 1, the preparation of a trans compound of the invention may be achieved by following a four step procedure.

In a first step (denoted "i" in FIG. 1), cyclohexene epoxide undergoes a ring-opening reaction with an amine. See, e.g., Szmuszkovicz, U.S. Pat. No. 4,145,435. While the reaction can occur at room temperature, typically elevated temperature is preferred in order to drive the reaction to completion in a commercially desirable length of time. The reaction is typically conducted in a solvent, such as water, and the reflux temperature of the solvent provides a suitable temperature.

Equal molar amounts of the amine and cyclohexene epoxide typically provide satisfactory results. In any event, the amine nitrogen reacts with the epoxide group to form a 1-hydroxy 2-amino cyclohexane, where the hydroxy and amine groups are typically disposed in a trans relationship. A wide variety of amine compounds and substituted cyclohexene oxides may be employed in this general reaction, and FIG. 1 illustrates this reaction in the instance where the amine is morpholine and the cyclohexene oxide is unsubstituted. For other amines or substituted cyclohexene epoxides that may contain other reactive functional groups, appropriate protection groups are introduced prior to step i) being carried out. Suitable protecting groups are set forth in, for example, Greene, "Protective Groups in Organic Chemistry", John Wiley & Sons, New York N.Y. (1991).

In a second step (denoted "ii)" in FIG. 1) the hydroxy group that was derived from the epoxide, is converted into an activated form. An "activated form" as used herein means that the hydroxy group is converted into a good leaving group. The leaving group illustrated in FIG. 1 is a mesylate group, and that is a preferred leaving group. However, the hydroxy group could be converted into other leaving groups according to procedures well known in the art. In a typical reaction, the aminocyclohexanol compound is treated with methanesulfonyl chloride in the presence of a base, such as triethylamine as shown in FIG. 1. The reaction is satisfactorily conducted at about 0° C. An excess of the methanesulfonyl chloride, relative to the aminocyclohexanol, is typically preferred in order to maximally convert the more valuable aminocyclohexanol into the activated form. For some other aminocyclohexanol compounds, it may be necessary to introduce appropriate protection groups prior to step ii) being performed. Suitable protecting groups are set forth in, for example, Greene, "Protective Groups in Organic Chemistry", John Wiley & Sons, New York N.Y. (1991).

In a third step (denoted "iii)" in FIG. 1) an alcohol is reacted with a strong base to provide an alkoxide salt. Conversion of an alcohol to an alkoxide (also known as an alcoholate) using strong base is a general reaction, and will work with a wide variety of hydroxy-containing compounds. In some instances, the alcohol compound may have other reactive functional groups that are desirably protected prior to contact of the alcohol with strong base. Suitable protecting groups are set forth in, for example, Greene, "Protective Groups in Organic Chemistry", John Wiley & Sons, New York N.Y. (1991). Such alcohols are either commercially available or may be obtained by procedures described in the art or adapted therefrom, where suitable procedures may be identified through the Chemical Abstracts and Indices therefor, as developed and published by the American Chemical Society.

In a fourth step (denoted "iv)" in FIG. 1), the alcoholate of step "iii)" is reacted with the activated aminocyclohexanol of step "ii)". Thus, generally stated, compounds of the present invention may be prepared by reacting an activated form of the appropriate 1,2-aminocyclohexanol (1 mol) with an alcoholate (1.25 mol) prepared by treatment of the selected alcohol (1.25 mol) with, for example, sodium hydride (1.3 mol). The 1,2-aminocyclohexanol (1 mol) can be activated by forming the corresponding mesylate, in the presence of methanesulfonyl chloride (1.25 mol) and triethylamine (1.5 mol). The mesylate is added quickly to the alcoholate, in a suitable solvent such as dimethylformamide. The reaction temperature is monitored carefully in order to avoid undesired side-reactions such as β-elimination. In general, a reaction temperature of 80-90° C. for 2 hours is typically suitable to form compounds of the invention. When the reaction has proceeded to substantial completion, the desired product is recovered from the reaction mixture by conventional organic chemistry techniques, and is purified generally by column chromatography followed by recrystallisation. Protective groups may be removed at the appropriate stage of the reaction sequence. Suitable methods are set forth in, for example, Greene, "Protective Groups in Organic Chemistry", John Wiley & Sons, New York N.Y. (1991).

The reaction sequence described above (and shown in FIG. 1) generates the aminocyclohexyl ether as the free base. The pure enantiomeric forms can be obtained by preparative chiral HPLC. The free base may be converted, if desired, to the monohydrochloride salt by known methodologies, and subsequently, if desired, to other acid addition salts by reaction with inorganic or organic salts. Acid addition salts can also be prepared metathetically by reacting one acid addition salt with an acid which is stronger than that of the anion of the initial salt.

Figure 2:
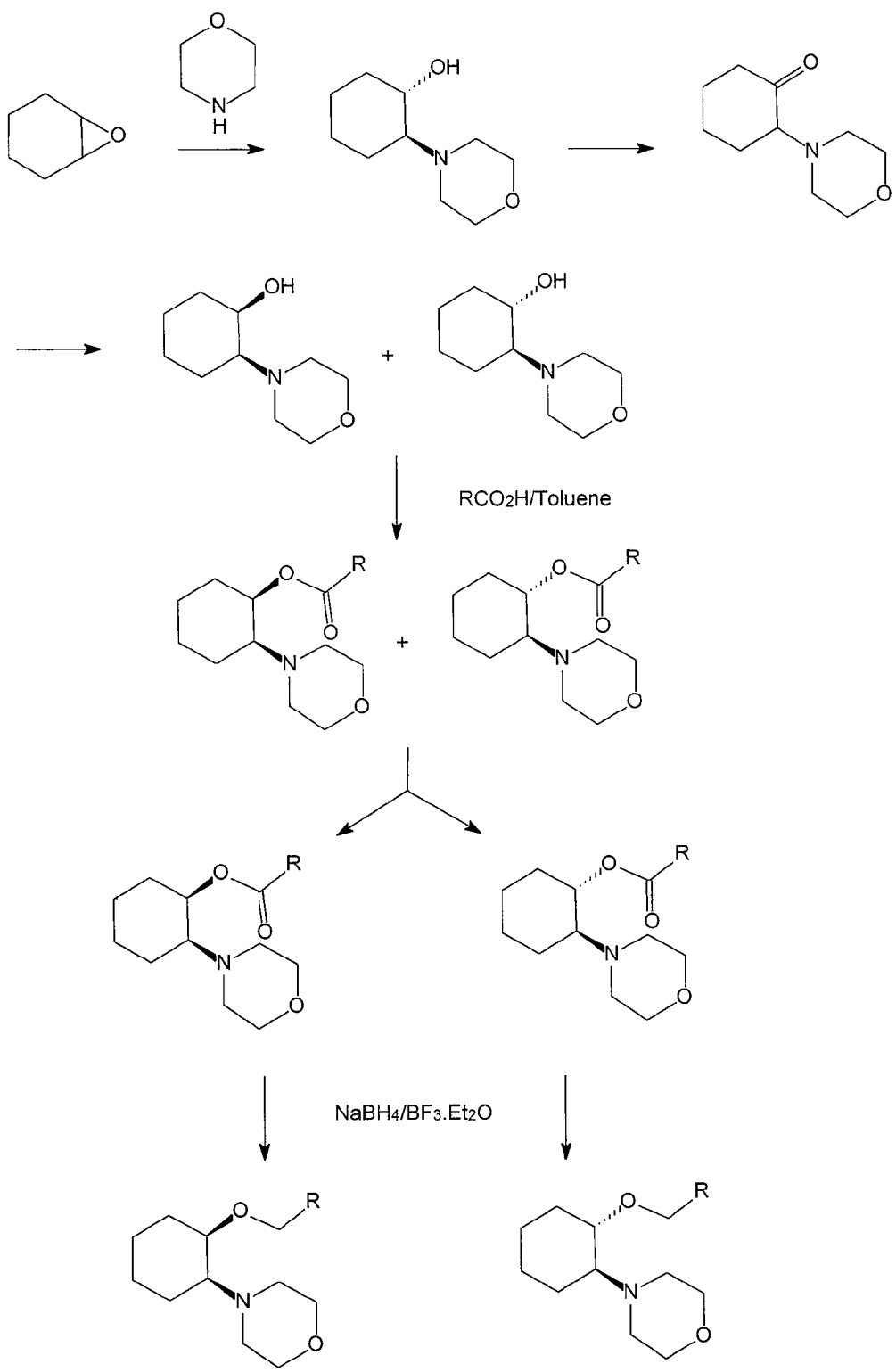
FIG. 2 illustrates a procedure whereby either cis- or trans-aminocyclohexyl ether compounds of the present invention may be prepared.

Cis or trans compounds of the invention may be prepared according to the chemistry outlined in FIG. 2. As shown in FIG. 2, 1,2-aminocyclohexanones may be prepared by Swern oxidation of the corresponding trans-1,2-aminocyclohexanol compounds (which may be prepared as described above) using oxalyl chloride/dimethyl sulfoxide (see, e.g., Synthesis 1980, 165). Subsequent reduction of the aminocyclohexanone with lithium aluminum hydride or sodium borohydride provides a mixture of cis- and trans-aminocyclohexanols. The mixture of aminoalcohols may be esterified with an appropriate carboxylic acid by azeotropic distillation in toluene in the presence of a catalytic amount of p-toluenesulfonic acid, to provide a diastereomeric mixture of cis- and trans-esters. The mixture of diastereomeric esters can be separated by preparative chromatography by one of ordinary skill in the art. The racemic cis- or trans ester preparation could then be reduced with sodium borohydride in the presence of Lewis acid to the corresponding racemic cis- or trans-ether (see, e.g., *J. Org. Chem.* 25, 875, 1960 and *Tetrahedron* 18, 953, 1962). The racemic cis-ether can be resolved by preparative chiral HPLC as discussed above for the trans-compound.

Figure 3:
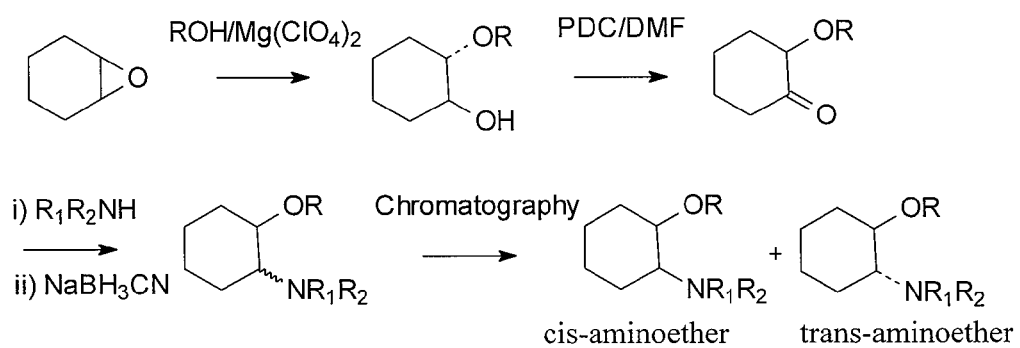
FIG. 3 illustrates synthetic methodology that may be employed to prepare either cis or trans stereoisomers of the compounds of the present invention.

Alternatively, cis and trans compounds of the invention may be prepared according to the chemistry outlined in FIG. 3. As shown in FIG. 3, cyclohexene oxide can react with an alcohol (ROH) in the present of Mg(ClO$_4$)$_2$ (see, e.g., M. Chini et al., *Synlett*, 673-676, 1992) to provide 1,2-hydroxy-cyclohexyl ethers. Oxidation with pyridinium dichromate (see, e.g., R. Oshima et al., *J. Org. Chem.*, 50, 2613-2621, 1985) yielded the corresponding 1,2-alkoxycyclohexanone. Subsequent reductive amination (R. F. Borch et al., *J. Am. Chem. Soc.*, 93(12), 2897-2904, 1971) provides a mixture of cis- and trans-aminocyclohexyl ethers. The mixture of diastereomeric ethers can be separated by chromatography by one of ordinary skill in the art. The racemic cis- or trans-ether so prepared could then be resolved by classical recrystallization methods well known in the art or by preparative chiral HPLC to provide the individual enantiomer: trans-(1R,2R), trans-(1S,2S), cis-(1R,2S) or cis-(1S,2R) aminoethers.

The synthetic procedures described herein, especially when taken with the general knowledge in the art, provide sufficient guidance to those of ordinary skill in the art to perform the synthesis, isolation, and purification of the compounds of the present invention.

Compositions and Modes of Administration

In another embodiment, the present invention provides compositions which include a cyclohexylamine compound as described above in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing a cyclohexylamine compound as described above, in admixture with a pharmaceutically acceptable carrier, excipient or diluent. The invention further provides a pharmaceutical composition containing an effective amount of a cyclohexylamine compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of cyclohexylamine compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. For instance, epinephrine may be combined with an aminocyclohexyl ether compound of the invention, to provide a composition useful to induce local anesthesia. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a cyclohexylamine compound as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydroxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active cyclohexylamine compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cyclohexylamine compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The composition in solid or liquid form may include an agent which binds to the cyclohexylamine compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment of arrhythmia, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease and other metal disorders, and alopecia. Other agents known to cause libido enhancement, local analgesia or anesthesia may be combined with compounds of the present invention.

The pharmaceutical compositions may be prepared by methodology well known in the pharmaceutical art. The aminocyclohexyl compounds of the invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the cyclohexylamine compound with water, and preferably buffering agents, so as to form a solution. The water is preferably sterile pyrogen-free water. A surfactant may be added to facilitate the formation of a homogeneous solution or suspension. Surfactants are compounds that non-covalently interact with the cyclohexylamine compound so as to facilitate dissolution or homogeneous suspension of the cyclohexylamine compound in the aqueous delivery system. Surfactants are desirably present in aqueous compositions of the invention because the cyclohexylamine compounds of the present invention are typically hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

Pharmacological Testing

As noted above, the present invention provides for utilizing the compounds described above in in vitro and in vivo methods. In one embodiment, ion channels, such as cardiac sodium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating or preventing a variety of diseases or disorders caused by defective or inadequate function of the ion channels. The compounds of the invention are found to have significant activity in modulating ion channel activity both in vivo and in vitro.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. The diseases and conditions to which the compounds, compositions and methods of the present invention may be applied as follows: arrhythmia, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other mental disorder, and alopecia.

Furthermore, the present invention provides a method for producing local analgesia or anesthesia in a warm-blooded animal which includes administering to a warm-blooded animal in need thereof an effective amount of a compound of formula (I) or a pharmaceutical composition containing a compound of formula (I). These methods may be used to relieve or forestall the sensation of pain in a warm-blooded animal.

Furthermore, the present invention provides a method wherein a preparation that contains ion channels is contacted with, or a warm-blooded animal (e.g., a mammal, such as a human) is administered an effective amount of an aminocyclohexyl ether compound of the invention. Suitable preparations containing cardiac sodium channels include cells isolated from cardiac tissue as well as cultured cell lines. The step of contacting includes, for example, incubation of ion channels with a compound under conditions and for a time sufficient to permit modulation of the activity of the channels by the compound.

In another embodiment, the compounds described above are provided for treating arrhythmia. As used herein, "treating arrhythmia" refers to both therapy for arrhythmia and for the prevention of arrhythmias occurring in a heart that is susceptible to arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred. The dosage amount and frequency are selected to create an effective level of the agent without harmful effects. It will generally range from a dosage of from about 0.1 to about 100 mg/kg/day, and typically from about 0.1 to 10 mg/kg where administered orally or intravenously for antiarrhythmic effect.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be coadministered with epinephrine in order to include local anesthesia.

In order to assess whether a compound has a desired pharmacological activity with the present invention, it is subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous boluses every 8 minutes to a pentobarbital anesthetized rat. The effects of the compound on blood pressure, heart rate and the ECG are measured 30 seconds, 1, 2, 4 and 8 minutes after each dose. Increasing doses are given until the animal dies. The cause of death is identified as being of either respiratory or cardiac origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests are performed using rat tissue. In order to ensure that a compound is not having effects which are only specific to rat tissue, further experiments are performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, halothane anesthetized baboons (*Papio anubis*). In this preparation, a blood pressure cannula and ECG electrodes are suitably placed in an anesthetized baboon. In addition, a stimulating electrode is placed into the right ventricle, together with a monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

In addition to the tests described above and in Examples 28-31, the pharmacological activity related to atrial arrhythmia (e.g. atrial fibrillation and atrial flutter) of the compounds of the present invention may be evaluated by other in vivo animal models established in the literature. Two such models are described below in Example 32 and Example 33.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23 G needle as applied to the shaved back of a guinea pig (*Cavia porcellus*) is assessed following subcutaneous administration of sufficient (50 µl, 10 mg/ml) solution in saline to raise a visible bleb on the skin. Each test was done on the central area of the bleb and also on its periphery to check for diffusion of the test solution from the point of administration. If the test animal produces a flinch in response to the stimulus, this demonstrates the absence of blockade of pain sensation. Testing was carried out at intervals for up to 4 hours post administration. The sites of bleb formation were examined after 24 hours and showed no skin abnormalities consequent to local administration of test substances or of saline, the vehicle used for preparation of the test solutions.

Other Compositions

The present invention also provides kits that contain a pharmaceutical composition which includes one or more compounds of the above formulae. The kit also includes instructions for the use of the pharmaceutical composition for modulating the activity of ion channels, for the treatment of arrhythmia or for the production of local analgesia and/or anesthesia, and for the other utilities disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

The following examples are offered by way of illustration and not by way of limitation. In the Examples, and unless otherwise specified, starting materials were obtained from well-known commercial supply houses, e.g., Aldrich Chemical Company (Milwaukee, Wis.), and were of standard grade and purity. "Ether" and "ethyl ether" each refers to diethyl ether; "h." refers to hours; "min." refers to minutes; "GC" refers to gas chromatography; "v/v" refers to volume per volume; and ratios are weight ratios unless otherwise indicated.

EXAMPLES

Example 1

(±)-trans-[2-(4-morpholinyl)-1-(2-naphthenethoxy)] cyclohexane Monohydrochloride Compound #1

(i) Morpholine (5 mL, 57 mmol), cyclohexene oxide (5.8 mL, 57 mmol) and water (3 mL) were refluxed for 1.5 h. GC analysis showed the reaction to be complete. The cooled mixture was partitioned between saturated NaOH solution (50 mL) and ether (75 mL). The aqueous layer was backwashed with ether (30 mL) and the combined ether layers were dried over sodium sulfate. The ether was removed in vacuo to leave a yellow oil (9.83 g). The crude product, (±)-trans-[2-(4-morpholinyl)]cyclohexanol, was purified by vacuum distillation (b.p. 75-80° C. at full vacuum) to give a clear liquid (8.7 g). Yield 82.5%.

(ii) To a chilled (0° C.) solution of (±)-trans-[2-(4-morpholinyl)]cyclohexanol (6.0 g, 32.4 mmol) and triethylamine (6.8 mL, 48 mmol) in dichloromethane (100 mL) was added via cannula a solution of methanesulfonyl chloride (3.10 mL, 40 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide 8.5 g (100% yield) of the crude mesylate.

(iii) To sodium hydride, 80% oil dispersion previously washed with hexanes (3×20 mL), (1.24 g, 51.6 mmol) in dry dimethylformamide (50 mL) was added via cannula a solution of 2-naphthenethanol (6.8 g, 40 mmol) in dry dimethylformamide (50 mL). Addition was followed by gas evolution and, as the reaction mixture was stirred at room temperature, it began to gel. The mesylate as prepared in (ii) above was dissolved in dimethylformamide (50 mL) and the resulting solution was added quickly via cannula to the slurry of alcoholate. The reaction mixture was heated to 80° C. and then the temperature reduced to 40° C. The resulting yellow solution was poured into ice-water (1500 mL) and extracted with ethyl acetate (3×300 mL). The combined organic extracts were backwashed with a saturated aqueous solution of sodium chloride (500 mL) and dried over sodium sulfate. Evaporation of the solvent in vacuo provided 13.4 g of an amber oil which was dissolved in water (150 mL) and the pH of the solution was adjusted to pH 2 with aqueous 1M HCl. The acidic aqueous solution was extracted with ethyl ether (2×100 mL)

and then basified to pH 10 with 50% sodium hydroxide aqueous solution. The basic aqueous solution was extracted with ethyl ether (2×100 mL), the combined organic layers were dried over sodium sulfate and concentrated in vacuo to leave 7.16 g of the crude free aminoether. The crude product was purified by chromatography on silica gel 60 (70-230 mesh) with a mixture of ethyl acetate-chloroform (1:1, v/v) as eluent to yield 4.37 g of the pure free base. The product was dissolved in ethyl ether (80 mL) and converted to the monohydrochloride salt by adding saturated solution of HCl in ethyl ether (80 mL). An oil came out of the solution, the solvent was evaporated in vacuo and the residue dissolved in the minimum amount of warm ethyl alcohol, addition of a large volume of ethyl ether triggered crystallization. The crystals were collected to afford 3.83 g (31% yield) of the title compound, m.p. 158-160° C., having the elemental analysis indicated in Table 1.

Example 2

(±)-trans-[2-(4-morpholinyl)-1-(1-naphthenethoxy)]cyclohexane Monohydrochloride

Compound #2

(i) The starting trans-aminocyclohexanol is prepared according to example 1.

(ii) To a chilled (0° C.) solution of (±)-trans-[2-(4-morpholinyl)]cyclohexanol (6.0 g, 32 mmol) and triethylamine (6.8 mL, 48 mmol) in dichloromethane (100 mL) was added via cannula a solution of methanesulfonyl chloride (3.10 mL, 40 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide 9.0 g of the crude mesylate.

(iii) To sodium hydride, 80% oil dispersion, previously washed with hexanes (3×20 mL) (1.30 g, 51.6 mmol), in dry dimethylformamide (50 mL) was added via cannula a solution of 1-naphthenethanol (6.8 g, 40 mmol) in dry dimethylformamide (50 mL). Addition was followed by evolution of gas and the reaction mixture was stirred at room temperature for 4 hours. The mesylate as prepared in (ii) above was dissolved in dry dimethylformamide (50 mL) and the resulting solution was added quickly (3 min.) via cannula to the slurry of alcoholate. The reaction mixture was heated to 80° C. for 3 hours, then the temperature was reduced to 35° C. for overnight stirring. The reaction mixture was poured into ice-water (1500 mL) and extracted with ethyl acetate (3×300 mL). The combined organic extracts were backwashed with a saturated aqueous solution of sodium chloride (500 mL) and dried over sodium sulfate. Evaporation of the solvent in vacuo provided 12.0 g of an oil which was dissolved in ether (80 mL) and treated with a saturated solution of HCl in ether. A sticky product came out of solution, the solvent was evaporated in vacuo and the resulting crude hydrochloride salt was dissolved in water (200 mL). The acidic aqueous solution was extracted with ethyl ether (2×1100 mL) and then basified to pH 10 with 50% sodium hydroxide aqueous solution. The basic aqueous solution was extracted with ethyl ether (2×100 mL), the combined organic layers were dried over sodium sulfate and concentrated in vacuo to leave 7.20 g of the crude free amino ether. The crude product was purified by chromatography on silica gel 60 (70-230 mesh) with a mixture of ethyl acetate-dichloromethane (1:1, v/v) as eluent to provide the pure free base. The product was dissolved in ethyl ether (80 mL) and converted to the monohydrochloride salt by adding a saturated solution of HCl in ethyl ether (80 mL). A white product precipitated and this solid was collected and dissolved in the minimum amount of warm ethyl alcohol; addition of a large volume of ethyl ether triggered crystallization. The crystals were collected to afford 2.30 g of the title compound, m.p. 198-200° C., having the elemental analysis indicated in Table 1.

Example 3

(±)-trans-[2-(4-morpholinyl)-1-(4-bromophenethoxy)]cyclohexane Monohydrochloride Compound #3

(i) The starting trans-aminocyclohexanol is prepared according to example 1.

(ii) To a chilled (0° C.) solution of (±)-trans-[2-morpholinyl)]cyclohexanol (3.0 g, 16.2 mmol) and triethylamine (3.4 mL, 24 mmol) in dichloromethane (25 mL) was added via cannula a solution of methanesulfonyl chloride (1.55 mL, 20.0 mmol) in dichloromethane (25 mL). The addition was completed in 5 min., the reaction mixture was stirred for another hour at 0° C. and then at room temperature for 2 hours. The reaction mixture was diluted with dichloromethane (50 mL) and washed with water (2×50 mL) and the combined aqueous washings back extracted with dichloromethane (25 mL). The combined organic layers were dried over sodium sulfate and concentrated in vacuo to provide 4.7 g of the crude mesylate.

(iii) To sodium hydride, 80% oil dispersion, previously washed with hexanes (3×10 mL), (0.62 g, 25.8 mmol) in dry dimethylformamide (25 mL) was added via cannula a solution of 4-bromophenethylalcohol (4.0 g, 20 mmol) in dimethylformamide (50 mL). Addition was followed by evolution of gas and the reaction mixture was stirred at room temperature for 4 hours. The mesylate as prepared in (ii) above was dissolved in dry dimethylformamide (50 mL) and the resulting solution was added quickly (3 min.) via cannula to the slurry of alcoholate. The reaction mixture was heated to 80° C. for 2 hours, then the temperature was reduced to 35° C. and the reaction stirred overnight. The reaction mixture was poured into ice-water (800 mL) and extracted with ethyl acetate (3×200 mL). The combined organic extracts were backwashed with a saturated aqueous solution of sodium chloride (150 mL) and dried over sodium sulfate. Evaporation of the solvent in vacuo provided 7.4 g of an oil which was dissolved in ether (80 mL) was treated with a saturated solution of HCl in ether. An oil came out of solution, the solvent was evaporated in vacuo and the residue was dissolved in water (100 mL). The acidic aqueous solution was extracted with ethyl ether (2×50 mL) and then basified to pH 10 with 50% sodium hydroxide aqueous solution. The basic aqueous solution was extracted with ethyl ether (2×50 mL), the combined organic layers were dried over sodium sulfate and concentrated in vacuo to leave 3.67 g of the crude free amino ether. The crude product was purified by chromatography on silica gel 60 (70-230 mesh) with a mixture of ethyl acetate-dichloromethane (1:1, v/v) as eluent to provide the pure free base. The product was dissolved in ethyl ether (30 mL) and converted to the monohydrochloride salt by adding a saturated solution of HCl in ethyl ether (30 mL). The solvent was evaporated and the residue dissolved in the minimum amount of ethyl alcohol, addition of a large volume of ethyl ether triggered crystallization. The crystals were collected to afford 1.31 g of the title compound, m.p. 148-151° C., having the elemental analysis indicated in Table 1.

Example 4

(±)-trans-[2-(4-morpholinyl)-1-[2-(2-naphthoxy) ethoxy)]cyclohexane Monohydrochloride Compound #4

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide 4.3 g (100% yield) of the crude mesylate.

(iii) To sodium hydride, 80% oil dispersion, previously washed with hexanes (3×10 mL), (0.7 g, 29 mmol) in dry dimethylformamide (50 mL) was added via cannula a solution of 2-(2-naphthoxy)ethanol (3.76 g, 20.0 mmol) in dry dimethylformamide (50 mL). Addition was followed by evolution of gas and the reaction mixture was stirred at room temperature for 90 min. The mesylate as prepared in (ii) above was dissolved in dry dimethylformamide (50 mL) and the resulting solution was added quickly (3 min.) via cannula to the reaction mixture. The resulting reaction mixture was heated overnight to 90° C. and then cooled to room temperature. The reaction mixture was poured into ice-water (800 mL) and extracted with ethyl acetate (3×200 mL). The combined organic extracts were backwashed with a saturated aqueous solution of sodium chloride (300 mL) and dried over sodium sulfate. Evaporation of the solvent in vacuo provided 7.8 g of a yellow oil which was dissolved in ether (100 mL) and treated with a saturated solution of HCl in ether (100 mL). The resulting precipitate was collected, partially solubilized in water (200 mL) and the heterogeneous aqueous solution was extracted with ether (2×100 mL). The remaining insoluble material was collected and recrystallized in boiling ethanol (75 mL) to provide a first crop of the desired product. The acidic aqueous solution was basified to pH 10 with aqueous 50% NaOH and extracted with ether (2×50 mL). The combined organic extracts were dried over sodium sulfate and concentrated in vacuo to provide 1.6 g of the crude free amino ether. The product was purified by chromatography on silica gel 60 (70-230 mesh) using a mixture of ethyl acetate-dichloromethane as eluent to yield 0.73 g of a pale yellow oil. The pure free base was then dissolved in ether (50 mL) and converted to the monohydrochloride salt by adding a saturated solution of HCl in ether (50 mL). The white precipitate was collected and recrystallized in boiling ethanol (40 mL) to provide a second crop. Combination of the two crops afforded 1.03 g of the title compound, m.p. 235-237° C., having the elemental analysis indicated in Table 1.

Example 5

(±)-trans-[2-(4-morpholinyl)-1-[2-(4-bromophenoxy) ethoxy)]]cyclohexane Monohydrochloride Compound #5

(i) The starting trans-aminocyclohexanol is prepared according to example 1.

(ii) To a chilled (0° C.) solution of (I)-trans-[2-(4-morpholinyl)]cyclohexanol (3.0 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide 3.95 g (92% yield) of the crude mesylate.

(iii) To sodium hydride, 80% oil dispersion, previously washed with hexanes (3×10 mL), (0.63 g, 26 mmol) in dry dimethylformamide (50 mL) was added via cannula a solution of 2-(4-bromophenoxy)ethanol (4.34 g, 20.0 mmol) in dry dimethylformamide (50 mL). Addition was followed by evolution of a gas and the reaction mixture was stirred at room temperature for 90 min. The mesylate as prepared in (ii) above was dissolved in dry dimethylformamide (50 mL) and the resulting solution was added quickly (3 min.) via cannula to the reaction mixture. The reaction mixture was heated to 90° C. for 90 min. and then the temperature was reduced to 40° C. and the reaction was stirred overnight. The reaction mixture was poured into ice-water (800 mL) and extracted with ethyl acetate (3×200 mL). The combined organic extracts were backwashed with a saturated aqueous solution (300 mL) of sodium chloride and dried over sodium sulfate. Evaporation of the solvent in vacuo provided 8.35 g of a yellow oil which was dissolved in ether (100 mL) and treated with a saturated solution of HCl in ether (100 mL). The resulting white solid was collected and recrystallized in boiling ethanol (150 mL) to yield 3.7 g (54% yield) of the pure title compound, m.p. 228-230° C., having the elemental analysis indicated in Table 1.

Example 6

(±)-trans-[2-(4-morpholinyl)-1-(3,4-dimethoxyphenethoxy)]cyclohexane Monohydrochloride Compound #6

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide 4.18 g of the crude mesylate.

(iii) To sodium hydride, 80% oil dispersion, previously washed with hexanes (3×10 mL), (0.64 g, 27 mmol) in dry dimethylformamide (50 mL) was added via cannula a solution of 3,4-dimethoxyphenethyl alcohol (3.64 g, 20.0 mmol) in dry dimethylformamide (50 mL). Addition was followed by evolution of a gas and the reaction mixture was stirred at room temperature for 90 min. The mesylate as prepared in (ii) above was dissolved in dry dimethylformamide (50 mL) and the resulting solution was added quickly (3 min.) via cannula to the reaction mixture. The reaction mixture was heated to 80° C. for 90 min. and then the temperature was reduced to 40° C. and stirring continued overnight. The reaction mixture was poured into ice-water (800 mL) and extracted with ethyl acetate (3×200 mL). The combined organic extracts were backwashed with a saturated aqueous solution of sodium chloride (300 mL) and dried over sodium sulfate. Evaporation of the solvent in vacuo provided 7.18 g of the crude product which was dissolved in ether (100 mL) and treated with a saturated solution of HCl in ether (100 mL). The solvent was evaporated in vacuo and the residual oil was taken up with water (100 mL) and extracted with ether (2×50 mL). The aqueous layer was basified to pH10 with 50% NaOH aqueous solution and extracted with ether (2×50 mL). The combined organic layers were dried over sodium sulfate and concentrated in vacuo. The crude product was purified by chromatography on silica gel 60 (70-230 mesh) using a mixture of ethyl acetate and dichloromethane (1:1, v/v) as eluent to provide 2.8 g of a pale yellow oil. The free base was dissolved in ether (80 mL) and converted to the monohydrochloride salt by adding a saturated solution of HCl in ether (80 mL). The sticky precipitate was collected, dissolved in the minimum amount of ethanol and a large excess of ether was added to trigger crystallization of 2.24 g (36% yield) of the title compound, m.p. 148-150° C., having the elemental analysis indicated in Table 1.

Example 7

(±)-trans-[2-(1-pyrrolidinyl)-1-(1-naphthenethoxy)] cyclohexane Monohydrochloride Compound #7

(i) Pyrrolidine (25 mL, 300 mmol), cyclohexene oxide (30 mL, 297 mmol) and water (10 mL) were refluxed for 3 h. GC analysis showed the reaction to be complete. The cooled mixture was partitioned between saturated NaOH solution (10 mL) and ether (150 mL). The aqueous layer was backwashed with ether (2×100 mL) and the combined ether layers were dried over sodium sulfate. The ether was removed in vacuo to leave a yellow oil. The crude product was purified by vacuum distillation (b.p. 66-69° C. at full vacuum) to give a clear liquid (43.9 g). Yield 87%.

(ii) To a chilled (0° C.) solution of (±)-trans-[2-(pyrrolidinyl)]cyclohexanol (2.74 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 10 min., the reaction mixture was washed with water (2×50 mL) and the combined aqueous washings back extracted with dichloromethane (50 mL). The combined organic layers were dried over sodium sulfate and concentrated in vacuo to provide 3.24 g of the crude mesylate.

(iii) To sodium hydride, 80% oil dispersion, previously washed with hexanes (3×10 ml), (0.64 g, 27 mmol) in dry dimethylformamide (50 mL) was added via cannula a solution of 1-naphthenethanol (3.64 g, 20.0 mmol) in dry dimethylformamide (50 mL). Addition was followed by evolution of a gas and the reaction mixture was stirred at room temperature for 90 min. The mesylate as prepared in (ii) above was dissolved in dry dimethylformamide (50 mL) and the resulting solution was added quickly (3 min.) via cannula to the reaction mixture. The reaction mixture was heated to 80° C. for 90 min. and then its temperature was reduced to 40° C. and it was stirred overnight. The reaction mixture was poured into ice-water (800 mL) and extracted with ethyl acetate (3×200 mL). The combined organic extracts were backwashed with a saturated aqueous solution with sodium chloride (300 mL) and dried over sodium sulfate. Evaporation of the solvent in vacuo provided 9.00 g of the crude product which was dissolved in ether (50 mL) and treated with a saturated solution of HCl in ether (50 mL). The solvent was evaporated in vacuo and the residual oil was taken up with water (100 mL) and extracted with ether (2×50 mL). The aqueous layer was basified to pH10 with 50% NaOH aqueous solution and extracted with ether (2×50 mL). The combined organic layers were dried over sodium sulfate and concentrated in vacuo. The crude product was purified by chromatography on silica gel 60 (70-230 mesh) using a mixture of ethyl methanol and chloroform (2:8, v/v) as eluent. The free amino ether was partially dissolved in ether (80 mL), insoluble materials were filtered off, and then a saturated solution of HCl in ether (80 mL) was added to the filtrate. The solvent was evaporated in vacuo, the residue was dissolved in acetone and addition of aliquots of ether triggered slow crystallization. 2 crops of the title compound (0.88 g), m.p. 103-105° C. were collected, having the elemental analysis indicated in Table 1.

Example 8

(±)-trans-[2-(4-morpholinyl)-1-(2-(benzo[B] thiophen-3-yl)ethoxy)]cyclohexane Monohydrochloride Compound #8

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 5 min., the reaction mixture was stirred for another hour at 0° C. and then at room temperature for 3 hours. The reaction mixture was washed with water (3×30 mL) and the combined aqueous washings back extracted with dichloromethane (50 mL). The combined organic layers were dried over sodium sulfate and concentrated in vacuo to provide 5.25 g of the crude mesylate.

(iii) To sodium hydride, 80% oil dispersion, previously washed with hexanes (3×10 mL), (0.60 g, 25 mmol) in dry dimethylformamide (50 mL) was added via cannula a solution of 2-(benzo[b]thiophen-3yl)ethanol (3.56 g, 20.0 mmol) in dry dimethylformamide (50 mL). Addition was followed by evolution of gas and the reaction mixture was stirred at room temperature for 3 hours. The mesylate as prepared in (ii) above was dissolved in dry dimethylformamide (50 mL) and the resulting solution was added quickly (2 min.) via cannula to the reaction mixture. The reaction mixture was heated to 75° C. for 2 hours, then the temperature was reduced to 65° C. and stirring continued overnight. The reaction mixture was poured into ice-water (800 mL) and extracted with ethyl acetate (3×200 mL). The combined organic extracts were backwashed with a saturated aqueous solution (300 mL) of sodium chloride and dried over sodium sulfate. Evaporation of the solvent in vacuo provided 7.7 g of an oil which was dissolved in ether (100 mL) and treated with a saturated solution of HCl in ether (100 mL). An oil precipitated from the solution, the solvent was evaporated in vacuo and the resulting crude hydrochloride salt was dissolved in water (200 ml). The acidic aqueous solution was extracted with ethyl ether (2×100 mL) and then basified to pH 10 with aqueous 50% sodium hydroxide. The basic aqueous solution was extracted with ethyl ether (3×100 mL), the combined organic layers were dried over sodium sulfate and concentrated in vacuo to leave 3.30 g of the crude free aminoether. The crude product was purified by chromatography on silica gel 60 (70-230 mesh) with a mixture of ethyl acetate and dichloromethane (1:1, v/v) as eluent to provide the free base. The product was dissolved in ethyl ether (100 mL) and converted to the monohydrochloride salt by adding a saturated solution of HCl in ethyl ether (100 mL). The solvent was evaporated in vacuo and the residue was dissolved in the minimum amount of boiling methanol to provide a first crop (0.7 g) of crystalline product on cooling. Addition of diethyl ether to the methanol filtrate provided a second crop (0.55 g). The two crops were combined to yield 1.25 g of the title compound, m.p. 158-160° C., having the elemental analysis indicated in Table 1.

Example 9

(±)-trans-[2-(4-morpholinyl)-1-(2-(benzo[B]thiophen-4-yl)ethoxy)]cyclohexane Monohydrochloride Compound #9

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24.0 mmol) in dichloromethane (50 mL) was added via cannula a solution of methanesulfonyl chloride (1.55 mL, 20.0 mmol) in dichloromethane (50 mL). The addition was completed in 5 min., the reaction mixture was stirred for another hour at 0° C. and then at room temperature for 3 hours. The reaction mixture was washed with water (2×30 mL) and the combined aqueous washings back extracted with dichloromethane (50 mL). The combined organic layers were dried over sodium sulfate and concentrated in vacuo to provide 4.24 g of the crude mesylate.

(iii) To sodium hydride, 80% oil dispersion, previously washed with hexanes (3×10 mL), (0.60 g, 25 mmol) in dry dimethylformamide (50 mL) was added via cannula a solution of 2-(benzo[b]thiophen-4-yl)ethanol (3.56 g, 20.0 mmol) in dry dimethylformamide (50 mL). Addition was followed by evolution of a gas and the reaction mixture was stirred at room temperature for 3 hours. The mesylate as prepared in (ii) above was dissolved in dry dimethylformamide (50 mL) and the resulting solution was added quickly (2 min.) via cannula to the reaction mixture. The reaction mixture was heated to 85° C. for 2 hours, then the temperature was reduced to 40° C. and the reaction stirred overnight. The reaction mixture was poured into ice-water (800 mL) and extracted with ethyl acetate (3×200 mL). The combined organic extracts were backwashed with a saturated aqueous solution (300 mL) of sodium chloride and dried over sodium sulfate. Evaporation of the solvent in vacuo provided 8.2 g of an oil which was dissolved in ether (100 mL) and treated with a saturated solution of HCl in ether (100 mL). An oil precipitated and the solvent was evaporated in vacuo and the resulting crude hydrochloride salt was dissolved in water (200 mL). The acidic aqueous solution was extracted with ethyl ether (2×100 mL) and then basified to pH 10 with an aqueous solution of sodium hydroxide (50% w/v). The basic aqueous solution was extracted with ethyl ether (3×100 mL), the combined organic layers were dried over sodium sulfate and concentrated in vacuo to leave 3.0 g of the crude free aminoether. The crude product was purified by chromatography on silica gel 60 (70-230 mesh) with a mixture of ethyl acetate-dichloromethane (1:1, v/v) as eluent to provide the pure free base. The product was dissolved in ethyl ether (50 mL) and converted to the monohydrochloride salt by adding a saturated solution of HCl in ethyl ether (50 mL). The solvent was evaporated in vacuo, the residue was dissolved in the minimum amount of cold ethanol and addition of ether triggered formation of crystals (1.17 g), m.p. 178-180° C., having the elemental analysis indicated in Table 1.

Example 10

(±)-trans-[2-(4-morpholinyl)-1-(3-bromophenethoxy)]cyclohexane Monohydrochloride Compound #10

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 5 min., the reaction mixture was stirred for another hour at 0° C. and then at room temperature for 3 hours. The reaction mixture was washed with water (2×30 mL) and the combined aqueous washings back extracted with dichloromethane (50 mL). The combined organic layers were dried over sodium sulfate and concentrated in vacuo to provide 5.4 g of the crude mesylate.

(iii) To sodium hydride, 80% oil dispersion, previously washed with hexanes (3×10 mL), (0.60 g, 25 mmol) in dry dimethylformamide (50 mL) was added via cannula a solution of 3-bromophenethyl alcohol (4.0 g, 20 mmol) in dry dimethylformamide (50 mL). Addition was followed by evolution of a gas and the reaction mixture was stirred at room temperature for 3 hours. The mesylate as prepared in (ii) above was dissolved in dry dimethylformamide (50 mL) and the resulting solution was added quickly (2 min.) via cannula to the reaction mixture. The reaction mixture was heated to 85° C. for 2 hours, then the temperature was reduced to 45° C. and the reaction stirred overnight. The reaction mixture was poured into ice-water (800 mL) and extracted with ethyl acetate (3×200 mL). The combined organic extracts were backwashed with a saturated aqueous solution of sodium chloride (300 mL) and dried over sodium sulfate. Evaporation of the solvent in vacuo provided 8.0 g of an oil which was dissolved in ether (100 mL) and treated with a saturated solution of HCl in ether (100 mL). An oil precipitated and the solvent was evaporated in vacuo and the resulting crude hydrochloride salt was dissolved in water (200 mL). The acidic aqueous solution was extracted with ethyl ether (2×100 mL) and then basified to pH 10 with an aqueous solution of sodium hydroxide (50% w/v). The basic aqueous solution was extracted with ethyl ether (3×100 mL), the combined organic layers were dried over sodium sulfate and concentrated in vacuo to leave 2.9 g of the crude free aminoether. The crude product was purified by chromatography on silica gel 60 (70-230 mesh) with a mixture of ethyl acetate-dichloromethane (1:1, v/v) as eluent to provide the pure free base. The product was dissolved in ethyl ether (50 mL) and converted to the monohydrochloride salt by adding saturated solution of HCl in ethyl ether (50 mL). The solvent was evaporated in vacuo, the residue was dissolved in the minimum amount of cold ethanol and addition of ether triggered formation of crystals (0.53 g), m.p. 145-148° C., having the elemental analysis indicated in Table 1.

Example 11

(±)-trans-[2-(4-morpholinyl)-1-(2-bromophenethoxy)]cyclohexane Monohydrochloride Compound #11

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24.0 mmol) in dichloromethane (50 mL) was added via cannula a solution of methanesulfonyl chloride (1.55 mL, 20.0 mmol) in dichloromethane (50 mL). The addition was completed in 5 min., the reaction mixture was stirred for another hour at 0° C. and then at room temperature for 3 hours. The reaction mixture was washed with water (2×30 mL) and the combined aqueous washings back extracted with dichloromethane (50 mL). The combined organic layers were dried over sodium sulfate and concentrated in vacuo to provide 5.9 g of the crude mesylate.

(iii) To sodium hydride, 80% oil dispersion, previously washed with hexanes (3×10 mL), (0.60 g, 25 mmol) in dry dimethylformamide (50 mL) was added via cannula a solution of 2-bromophenethyl alcohol (4.0 g, 20 mmol) in dry dimethylformamide (50 mL). Addition was followed by evolution of a gas and the reaction mixture was stirred at room temperature for 3 hours. The mesylate as prepared in (ii) above was dissolved in dry dimethylformamide (50 mL) and the resulting solution was added quickly (2 min.) via cannula to the reaction mixture. The reaction mixture was heated to 85° C. for 2 hours, then the temperature was reduced to 45° C. and the reaction stirred overnight. The reaction mixture was poured into ice-water (800 mL) and extracted with ethyl acetate (3×200 mL). The combined organic extracts were backwashed with a saturated aqueous solution of sodium chloride (300 mL) and dried over sodium sulfate. Evaporation of the solvent in vacuo provided 8.4 g of an oil which was dissolved in 1.0 M HCl aqueous solution (50 mL), the volume was adjusted to 200 mL with water and the pH adjusted to pH 2 with 1.0 M HCl aqueous solution. The acidic aqueous solution was extracted with ethyl ether (3×100 mL) and then basified to pH 10 with 50% aqueous sodium hydroxide solution. The basic aqueous solution was extracted with ethyl ether (3×100 mL), the combined organic layers were dried over sodium sulfate and concentrated in vacuo to leave 2.8 g of the crude free aminoether. The crude product was purified by chromatography on silica gel 60 (70-230 mesh) with a mixture of ethyl acetate-dichlororethane (1:1, v/v) as eluent to provide the pure free base. The product was dissolved in ethyl ether (50 mL) and converted to the monohydrochloride salt by adding saturated solution of HCl in ethyl ether (50 mL). The solvent was evaporated in vacuo, the residue was dissolved in the minimum amount of cold ethanol and addition of ether triggered formation of crystals which were collected in two crops (0.74 g), m.p. 140-142° C., having the elemental analysis indicated in Table 1.

Example 12

(±)-trans-[2-(4-morpholinyl)-1-(3-(3,4-dimethoxyphenyl)-1-propoxy)]cyclohexane Monohydrochloride Compound #12

(i) The starting trans-aminocyclohexanol is prepared according to example 1.

(ii) To a chilled (0° C.) solution of (±)-trans-[2-(4-morpholinyl)]cyclohexanol (3.0 g, 16.2 mmol) and triethylamine (3.4 mL, 24 mmol) in dichloromethane (50 mL) was added via cannula a solution of methanesulfonyl chloride (1.55 mL, 20.0 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide the crude mesylate.

(iii) To sodium hydride, 80% oil dispersion, previously washed with hexanes (3×10 mL), (0.6 g, 27 mmol) in dry dimethylformamide (50 mL) was added via cannula a solution of 3-(3,4-dimethoxyphenyl)-1-propanol (3.93 g, 20.0 mmol) in dry dimethylformamide (50 mL). Addition was followed by evolution of a gas and the reaction mixture was stirred at room temperature for 90 min. The mesylate as prepared in (ii) above was dissolved in dry dimethylformamide (50 mL) and the resulting solution was added quickly (3 min.) via cannula to the reaction mixture. The reaction mixture was heated to 90° C. for 90 min. and then the temperature was reduced to 45° C. and stirring continued overnight. The reaction mixture was poured into ice-water (800 mL) and extracted with ethyl acetate (3×200 mL). The combined organic extracts were backwashed with a saturated aqueous solution of sodium chloride (300 mL) and dried over sodium sulfate. Evaporation of the solvent in vacuo provided 8.5 g of the crude product which was dissolved in 15% HCl aqueous solution (200 mL) and extracted with ether (2×100 mL). The aqueous layer was basified to pH 10 with 50% NaOH aqueous solution and extracted with ether (2×100 mL). The combined organic layers were dried over sodium sulfate and concentrated in vacuo. The crude product was purified by chromatography on silica gel 60 (70-230 mesh) using a mixture of ethyl acetate and dichloromethane (1:1, v/v) as eluent to provide the free base which was dissolved in ether (80 mL) and converted to the monohydrochloride salt by adding a saturated solution of HCl in ether (80 mL). The sticky precipitate was collected, dissolved in the minimum amount of warm ethanol and a large excess of ether was added to trigger crystallization of the title compound, m.p. 175-177° C., having the elemental analysis indicated in Table 1.

Example 13

(±)-trans-[2-[bis(2 Methoxyethyl)amino]-1-(2-naphthenethoxy)]cyclohexane Monohydrochloride Compound #13

(i) Bis-(2-methoxyethyl)amine (25 mL, 169 mmol) and cyclohexene oxide (17.2 mL, 170 mmol) were mixed in water (5 mL) and the resulting mixture was refluxed for 30 hours. The cooled reaction mixture was partitioned between 10% NaOH aqueous (200 mL) and diethyl ether (200 mL). The aqueous layer was extracted twice more with diethyl ether (2×100 mL), the combined organic layers were washed with water (8 mL) and dried over sodium sulfate. The solvent was evaporated in vacuo to provide the crude product which was vacuum distilled to provide 26.4 g of pure colorless oil.

(ii) To a chilled (0° C.) solution of (±)-trans-2-[bis(2-methoxyethyl)amino]cyclohexanol) 4.63 g, 20.00 mmol) and triethylamine (3.4 mL, 24.00 mmol) in dichloromethane (50 mL) was added via cannula a solution of methanesulfonyl chloride (1.55 mL, 20.00 mmol) in dichloromethane (50 mL). The additional was completed in 5 min., the reaction mixture was stirred for another hour at 0° C. and then at room temperature for 4 hours. The reaction mixture was washed with water (2×30 mL) and the combined aqueous washings back-extracted with dichloromethane (50 mL). The combined organic layers were dried over sodium sulfate and concentrated in vacuo to provide 4.87 g of the crude mesylate.

(iii) To sodium hydride, 80% oil dispersion, previously washed with hexanes (3×10 mL), (0.60 g, 25.00 mmol) in anhydrous dimethylformamide (50 mL) was added via cannula a solution of 2-naphthenethanol (3.4 g, 20.00 mmol) in anhydrous dimethylformamide (50 mL). Addition was followed by hydrogen bubbling, the reaction mixture was stirred at room temperature for 90 min. The mesylate as prepared in (ii) above was dissolved in dry dimethylformamide (50 mL) and the resulting solution was added quickly (3 min.) via cannula to the reaction mixture. The reaction mixture was heated up to 90° C. in 2 hours, then the temperature was reduced to 40° C. and the reaction stirred overnight. The reaction mixture was poured into ice-water (800 mL) and extracted with ethyl acetate (3×200 mL). The combined organic extracts were backwashed with a sodium chloride saturated aqueous solution (300 mL) and dried over sodium sulfate. Evaporation of the solvent in vacuo provided 8.1 g of an oil which was dissolved in 1M HCl aqueous solution (50 mL) and the volume completed to 200 mL with water. The acidic aqueous solution was extracted with diethyl ether (2×100 mL) and then basified to pH 10 with 50% sodium hydroxide aqueous solution. The basic aqueous solution was extracted with ethyl ether (2×100 mL), the combined organic layers were dried over sodium sulfate and concentrated in vacuo to leave 3.58 g of the crude free aminoether. The crude product was purified by chromatography column using silica gel 60, 70-230 mesh from BDH Inc. with a mixture of methanol and dichloromethane (2:8, v/v) as eluent to provide the pure free base. The product was dissolved in diethyl ether (50 mL) and converted to the monohydrochloride salt by adding ethereal HCl (50 mL). The solvent was evaporated in vacuo to yield 0.75 g of the title compound (not recrystallized).

Example 14

(1R,2R)/(1S,2S)-2-(4-morpholinyl)-1-(3,4-dichlorophenethoxy)cyclohexane Monohydrochloride Compound #14

The basic overall approach used to synthesize this compound is analogous to that shown in FIG. 1.

(i) (1R,2R)/(1S,2S)-2-(4-Morpholinyl)cyclohexanol: A mixture of cyclohexene oxide (206.5 mL, 2 mol, 98%) and morpholine (175 mL, 2 mol) in water (60 mL) was refluxed for 3.5 h. Morpholine (5.3 mL) was added to the reaction mixture, which was then further refluxed for 1.5 h. in order to complete the reaction. The cooled reaction mixture was then partitioned between 40% NaOH aqueous solution (100 mL) and diethyl ether (200 mL). The aqueous layer was separated from the organic layer and extracted twice more with diethyl ether (2×100 mL). The combined organic extracts were dried over sodium sulfate and the solvent was evaporated in vacuo. Vacuum distillation yielded 342.3 g (92.4%) of the title compound.

(ii) To a chilled (0° C.) solution of (1R,2R)/(1S,2S)-2-(4-morpholinyl)cyclohexanol (40.76 g, 0.22 mol) and triethylamine (36.60 mL, 0.26 mmol) in dichloromethane (400 mL) was added dropwise a solution of methanesulfonyl chloride (20.53 mL, 0.26 mol) in dichloromethane (50 mL). The reaction mixture was stirred at 0° C. for 45 min. and then at room temperature for 3 hours. The reaction mixture was then washed with water (2×100 mL); the combined washings were back-extracted with dichloromethane (100 mL). The combined organic extracts were dried over sodium sulfate and the solvent was evaporated in vacuo to yield the crude mesylate suitable for the next step without any further purification.

(iii) 3,4-Dichlorophenethyl alcohol: To a solution of lithium aluminum hydride (7.79 g, 195 mmol) in anhydrous diethyl ether (435 mL) was added slowly as a powder, via a solid dropping funnel, 3,4-dichlorophenyl acetic acid (27.20 g, 130 mmol). When the addition was completed, the reaction mixture was refluxed for 12 hours. The reaction was quenched by cautious addition of saturated sodium sulfate aqueous solution (20 mL), the resulting insoluble was then filtered off and the filtrate was concentrated in vacuo to yield 25.09 g of the desired alcohol.

(iv) To NaH (6.00 g, 0.2 mol, 80% dispersion in oil) in anhydrous ethylene glycol dimethyl ether (200 mL) was added a solution of 3,4-dichlorophenethyl alcohol (38.87 g, 0.2 mol) in anhydrous ethylene glycol dimethyl ether (100 mL). The resulting mixture was stirred for 3 hours at ambient temperature under argon atmosphere.

(v) The mesylate (ii) in anhydrous ethylene glycol dimethyl ether (100 mL) was added quickly to the alkoxide (iv) and the resulting reaction mixture was readily refluxed for 16 hours. To the cooled reaction mixture was added water (200 mL) and the organic solvent was evaporated in vacuo. The resulting aqueous solution was further diluted with water (200 mL) and the pH was adjusted to pH 1.5 with 10% HCl aqueous solution. The acidic aqueous layer was extracted with diethyl ether (500 mL) to eliminate the unreacted 3,4-dichlorophenethyl alcohol. Further basification of the aqueous layer with 5M NaOH aqueous solution to pH 5.7 followed by extraction with diethyl ether provided the crude title compound contaminated with some remaining mesylate (ii). The solvent of the organic extract at pH 5.7 was evaporated in vacuo, the residue was then refluxed in a mixture of ethanol-water (1:1, v/v, 200 mL) in the presence of sodium hydride (4.12 g, 0.1 mol) for 2 hours in order to hydrolyzed the remaining mesylate. The cooled reaction mixture was diluted with water (300 mL) and the organic solvent was evaporated in vacuo. The pH of the residual aqueous solution was adjusted to pH 5.7 with 6M HCl aqueous solution followed by extraction with diethyl ether (700 mL). The organic extract was concentrated in vacuo to yield the pure aminoether. The residual product was then partitioned between 1M HCl aqueous solution (300 mL) and dichloromethane (300 mL). The acidic aqueous solution was extracted twice more with dichloromethane (2×300 mL). The combined organic layers were dried over sodium sulfate, the solvent was evaporated in vacuo and the residue was recrystallized from a mixture of ethanol-hexanes (3:7, v/v, 700 mL) to yield 49.3 g of the title compound, having the elemental analysis indicated in Table 1.

Example 15

(1R,2R)/(1S,2S)-2-(3-ketopyrrolidinyl)-1-(1-naphthenethoxy)cyclohexane Monohydrochloride Compound #15

Figure 4A:
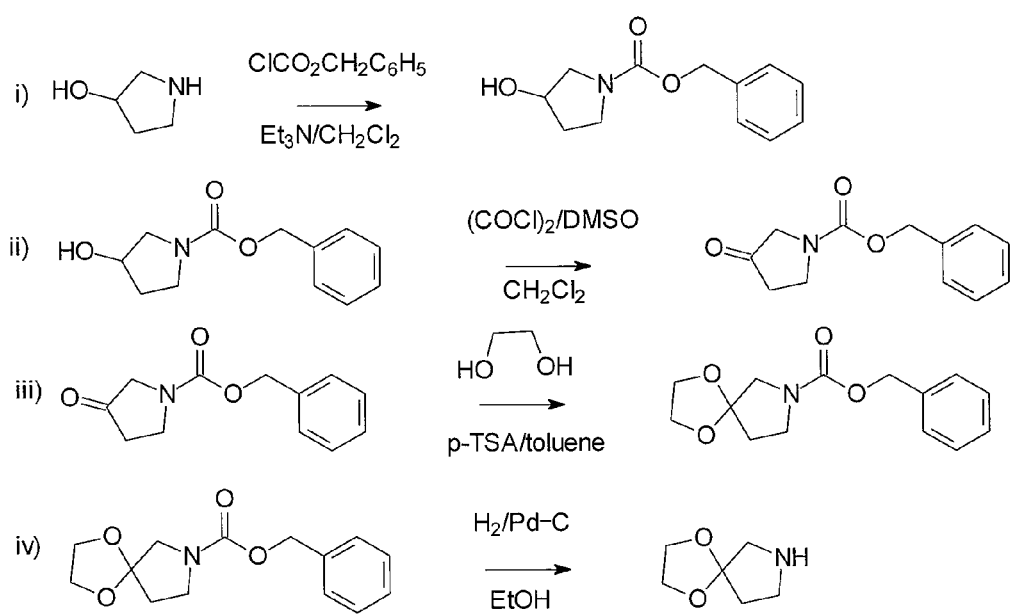
FIGS. 4A and 4B illustrate the synthetic methodology described in Example 15.
Figure 4B:
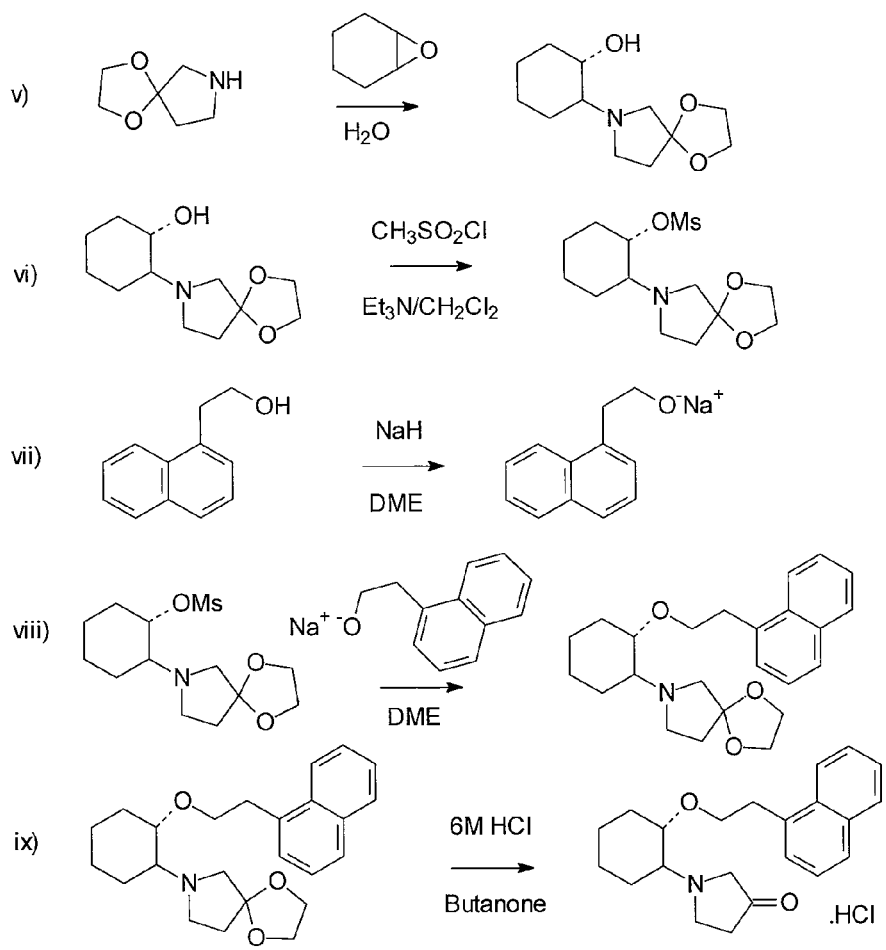

Synthesis of Compound #15 follows the sequence of reactions shown in FIG. 4A and FIG. 4B, and is described in detail below.

(i) N-Benzyloxycarbonyl-3-pyrrolidinol: To a chilled (−60° C.) solution of (R)-(+)-3-pyrrolidinol (20.0 g, 98%, 224.9 mmol) and triethylamine (79.2 mL, 99%, 562 mmol) in dichloromethane (200 mL) was added dropwise a solution of benzyl chloroformate (33.8 mL, 95%, 224.9 mmol) in dichloromethane (80 mL). After the addition was completed within 45 min, the reaction mixture (a yellow suspension) was allowed to warm up to room temperature and was stirred under argon at room temperature overnight. The reaction mixture was then quenched with 1M HCl aqueous solution (350 mL) and the organic layer was collected. The acidic aqueous layer was extracted with dichloromethane (2×150 mL) and the combined organic layers were dried over sodium sulfate. Evaporation in vacuo of the solvent provided 59.62 g of pale yellow oil, which was further pumped under high vacuum for 15 min to yield 58.23 g (17% over theoretical yield) of the crude title compound suitable for the next step without any further purification.

(ii) N-Benzyloxycarbonyl-3-pyrrolidinone: To a chilled (−60° C.) solution of oxalyl chloride (23 mL, 98%, 258.6 mmol) in dichloromethane (400 mL) was added dropwise a solution of anhydrous dimethyl sulfoxide (36.7 mL, 517.3 mmol) in dichloromethane (20 mL) at such a rate to keep the temperature below −40° C. The reaction mixture was then stirred at −60° C. for 15 min. Then a solution of N-benzyloxycarbonyl-3-pyrrolidinol (58.22 g, step i, no more than 224.9 mmol) in dichloromethane (80 mL) was added dropwise, keeping the reaction mixture temperature below −50° C. The reaction mixture was then stirred at −60° C. for 30 min before adding triethylamine (158.3 mL, 99%, 1.125 mol). The resulting mixture was allowed to warm up to room temperature and then washed with water (600 mL), 1M HCl aqueous solution (580 mL) and water (400 mL). The organic layer was dried over sodium sulfate and concentrated in vacuo to leave 54.5 g of amber oil, which was further pumped under high vacuum with stirring at room temperature for 25 min. to give 52.08 g (5.6% over theoretical yield) of the crude title compound suitable for the next step without any further purification.

(iii) 7-Benzyloxycarbonyl-1,4-dioxa-7-azaspiro[4.4]nonane: A mixture of N-benzyloxycarbonyl-3-pyrrolidinone (51.98 g, step ii, no more than 224.9 mmol) and ethylene glycol (18.8 mL, 99+%, 337.4 mmol) in toluene (180 mL) with a catalytic amount of p-toluenesulfonic acid monohydrate (1.04 g, 5.4 mmol) was refluxed in a Dean & Stark apparatus for 16 hours. The reaction mixture was then diluted with more toluene (250 mL) and washed with saturated sodium bicarbonate aqueous solution (150 mL) and saturated sodium chloride aqueous solution (2×150 mL). The combined aqueous layers were back-extracted with toluene (100 mL). The combined organic layers were dried over sodium sulfate and concentrated in vacuo to leave 79.6 g of dark oil. The crude product was dissolved in ethanol (500 mL), and running it through a bed of activated carbon (80 g), decolorized the resulting solution. The charcoal was washed with more ethanol (1000 mL) and toluene (500 mL). The filtrate was concentrated in vacuo and further pumped under high vacuum for 1 hour to yield 63.25 g (6.8% over theoretical yield) of the crude title compound suitable for the next step without any further purification.

(iv) 1,4-Dioxa-7-azaspiro[4.4]nonane: A mixture of 7-benzyloxycarbonyl-1,4-dioxa-7-azaspiro[4.4]nonane (34.79 g, step iii, no more than 123.7 mmol) and 10% Pd—C (13.9 g) in ethanol (90 mL) was hydrogenolyzed (60 psi) in a Parr shaker apparatus at room temperature for 1.5 hour. The catalyst was filtered off, the solvent was evaporated in vacuo and the residue was pumped under high vacuum for 20 min. to yield 15.86 g of the title compound (yield 99.3%).

(v) (1R,2R)/(1S,2S)-2-(1,4-Dioxa-7-azaspiro[4.4]non-7-yl)cyclohexanol: A mixture of 1,4-dioxa-7-azaspiro[4.4]nonane (23.54 g, step iv, no more than 182 mmol), cyclohexene oxide (22.6 mL, 98%, 219 mmol) and water (7.8 mL) was heated at 80° C. for 2 hours. The reaction mixture was then partitioned between 40% sodium hydroxide aqueous solution (60 mL) and diethyl ether (120 mL). The basic aqueous layer was extracted twice more with diethyl ether (2×120 mL). The combined organic extracts were dried over sodium sulfate and concentrated in vacuo. The residue was then pumped under high vacuum at 50° C. for 1 hour under stirring (to remove the excess of cyclohexene oxide) to yield 32.79 g of the crude title compound (yield 79.3%).

(vi) To a chilled (0° C.) solution of (1R,2R)/(1S,2S)-2-(1,4-dioxa-7-azaspiro[4.4]non-7-yl)cyclohexanol (27.47 g, 120 mmol, step v) and triethylamine (15.86 g, 156 mmol) in dichloromethane (240 mL) was added dropwise methanesulfonyl chloride (18.23 g, 156 mmol). The reaction mixture was stirred at 0° C. for 45 min. and then at room temperature for 3 hours. The reaction mixture was then washed with a mixture of water-saturated sodium bicarbonate aqueous solution (1:1, v/v, 120 mL). The washing layer was collected and was back-extracted with dichloromethane (120 mL). The combined organic extracts were dried over sodium sulfate, the solvent was evaporated in vacuo and the residue was pumped under high vacuum for 4 hours to yield the crude mesylate suitable for the next step without any further purification.

(vii) To sodium hydride (4.32 g, 144 mmol) suspended in anhydrous ethylene glycol dimethyl ether (80 mL) was added a solution of 1-naphthenethanol (25.31 g, 144 mmol) in anhydrous ethylene glycol dimethyl ether (80 mL). The resulting mixture was then stirred at room temperature for 4 hours.

(viii) (1R,2R)/(1S,2S)-2-[1,4-dioxa-7-azaspiro[4.4]non-7-yl]-1-(1-naphthenethoxy)cyclohexane: A solution of mesylate (vi) in anhydrous ethylene glycol dimethyl ether (80 mL) was added quickly to the alkoxide (vii) and the resulting mixture was readily heated to reflux under argon for 66 hours. The cooled reaction mixture was quenched with water (200 mL) and the organic solvent was evaporated in vacuo. The remaining aqueous solution was diluted with water (500 mL) and acidified with 10% HCl aqueous solution to pH 0.5. The acidic aqueous layer was extracted with diethyl ether (2×500 mL) in order to extract unreacted 1-naphthenethanol. The pH of the aqueous solution was adjusted to pH 4.8 with 5M NaOH aqueous solution and then extracted with diethyl ether (600 mL). The aqueous solution was further basified to pH 5.7 and extracted with diethyl ether (600 mL). The same procedure was repeated at pH 6.5 and 12.1. Analysis by gas chromatography of the different ether extracts showed that organic extracts at pH 4.8, 5.7 and 6.5 contained the title compound whereas ether extract at pH12.1 contained only unknown impurities. The organic extracts at pH 4.8, 5.7 and 6.5 were combined and dried over sodium sulfate. The solvent was evaporated in vacuo and the residue was pumped under high vacuum for 3.5 hours to yield 35.82 g (75% yield) of the title compound suitable for the next step without any further purification.

(ix) (1R,2R)/(1S,2S)-2-(3-Ketopyrrolidinyl)-1-(1-naphthenethoxy)cyclohexane monohydrochloride: A solution of (1R,2R)/(1S,2S)-2-[1,4-dioxa-7-azaspiro[4.4]non-7-yl]-1-(1-naphthenethoxy)cyclohexane (13.73 g, 36.0 mmol, step vi) with 6M HCl aqueous solution (50 mL) in 2-butanone (200 mL) was refluxed for 12 hours. The butanone was evaporated in vacuo and the residual aqueous solution was diluted to 250 mL with water. The aqueous solution was extracted with diethyl ether (2×200 mL) and then with dichloromethane (2×200 mL). The pooled dichloromethane extracts were dried over sodium sulfate and the solvent was evaporated in vacuo. The residual oil was azeotropically dried with toluene. The resulting sticky product was vigorously stirred overnight in diethyl ether (500 mL) with occasional scratching to trigger crystallization of the reaction product. The resulting solid was collected and solubilized in a small amount of dichloromethane (~10 mL), addition of a large quantity of diethyl ether (~400 mL) triggered recrystallization. The solid was collected, dried under high vacuum for 3 hours to yield 9.3 g (76% yield) of the title compound, having the elemental analysis indicated in Table 1.

Example 16

(1R,2R)/(1S,2S)-2-(1-acetylpiperazinyl)-1-(2-naphthenethoxy)cyclohexane Monohydrochloride Compound #16

Compound #16 was prepared according to a procedure similar as the one depicted in FIG. 1 and further detailed in Example 14.

(i) (1R,2R)/(1S,2S)-2-(1-Acetylpiperazinyl)-1-cyclohexanol: A mixture of 1-acetylpiperazine (5 g, 39 mmol) and cyclohexene oxide (3.95 mL, 39 mmol) in water (1.2 mL) was refluxed for 16 hours. The cooled reaction mixture was partitioned between 40% NaOH aqueous solution (20 mL) and diethyl ether (2×20 mL). The combined organic layers were dried over sodium sulfate and the solvent was evaporated in vacuo to yield 7.63 g of the title compound as white crystals (87% yield)

(ii) To a chilled (0° C.) solution of (1R,2R)/(1S,2S)-2-(1-acetylpiperazinyl)-1-cyclohexanol (3.65 g, 16.2 mmol) and triethylamine (3.4 mL, 24 mmol) in dichloromethane (50 mL) was added dropwise a solution of methanesulfonyl chloride (1.55 mL, 20 mmol) in dichloromethane (50 mL). The reaction mixture was stirred at 0° C. for one hour and then allowed to warm up to ambient temperature. The reaction mixture was then washed with water (2×50 mL) and the combined washings were back-extracted with dichloromethane (50 mL). The combined organic layers were dried over sodium sulfate and the solvent was evaporated in vacuo to yield the crude mesylate suitable for the next step without any further purification.

(iii) To a suspension of sodium hydride (0.8 g, 24 mmol, previously washed with hexanes (2×15 mL)) in anhydrous dimethylformamide (50 mL) was added a solution of 2-naphthenethanol in anhydrous dimethylformamide (50 mL). The resulting mixture was stirred at room temperature for 30 min.

(iv) (1R,2R)/(1S,2S)-2-(1-Acetylpiperazinyl)-1-(2-naphthenethoxy)cyclohexane monohydrochloride: the mesylate (ii) in solution in anhydrous dimethylformamide (50 mL) was added quickly to the alkoxide mixture (iii) and the resulting mixture was heated to 80° C. for 16 hours. The cooled reaction mixture was poured into ice water (800 mL) and extracted with ethyl acetate (3×200 mL). The combined organic extracts were back-washed with brine (200 mL) and the solvent was evaporated in vacuo. The residual oil was taken up with water (80 mL) and the resulting aqueous solution was acidified to pH 2 with 6M HCl aqueous solution. The acidic aqueous solution was extracted with diethyl ether (3×40 mL) in order to extract the unreacted 2-naphthenethanol. The pH of the aqueous layer was adjusted to pH10 with 50% NaOH aqueous solution and extracted with diethyl ether (3×40 mL). The combined organic extracts were dried over sodium sulfate and the solvent was evaporated in vacuo to yield the crude free aminoether. Purification by column chromatography of silica gel using a mixture of ethyl acetate-dichloromethane (1:1, v/v) as eluent provided the pure free base. Conversion to the hydrochloride salt was accomplished with ethereal HCl followed by recrystallization in a mixture of ethanol-diethyl ether provided the title compound, having the elemental analysis indicated in Table 1.

Example 17

(1R,2R)/(1S,2S)-2-(3-ketopyrrolidinyl)-1-(2,6-dichlorophenethoxy)cyclohexane Monohydrochloride Compound #17

Compound #17 was prepared in 10 steps according to the procedure described in Example 16. Steps (i) to (v) were identical to those in Example 16.

(vi) To a chilled (0° C.) solution of (1R,2R)/(1S,2S)-2-(1,4-dioxa-7-azaspiro[4.4]non-7-yl)cyclohexanol (27.77 g, 120 mmol) and triethylamine (22 mL, 156 mmol) in dichloromethane (240 mL) was added methanesulfonyl chloride (12.32 mL, 156 mmol). The reaction mixture was stirred at 0° C. for 45 min. and then at room temperature for 3 hours. The reaction mixture was washed with water (2×100 mL) and the combined washings were back-extracted with dichloromethane (120 mL). The combined organic extracts were dried over sodium sulfate and the solvent was evaporated in vacuo to yield the crude mesylate which was further pumped under high vacuum for 4 hours prior to use in step ix.

(vii) 2,6-Dichlorophenethyl alcohol: a suspension of lithium aluminum hydride (13.75 g, 365.75 mmol) in anhydrous diethyl ether (500 mL) was added via a powder addition funnel 2,6-dichlorophenylacetic acid (50 g, 243.75 mmol). The resulting reaction mixture was refluxed for 16 hours and then quenched by slow addition of a sodium sulfate saturated aqueous solution (25 mL). The resulting slurry was stirred for 3 hours and then filtered, the insoluble was carefully washed with diethyl ether (2×100 mL). The combined ether filtrates were dried over sodium sulfate and the solvent was evaporated in vacuo to yield 38.6 g (85% yield) of the title compound.

(viii) To sodium hydride (144 mmol, 4.32 g, 80% oil dispersion) in anhydrous ethylene glycol dimethyl ether (80 mL) was added a solution of 2,6-dichlorophenethyl alcohol (27.65 g, 144 mmol) in anhydrous ethylene glycol dimethyl ether (80 mL). The resulting mixture was stirred at room temperature under argon atmosphere for 4 hours.

(ix) (1R,2R)/(1S,2S)-2-[1,4-Dioxa-7-azaspiro[4.4]non-7-yl]-1-(2,6-dichlorophenethoxy)cyclohexane: The mesylate (vi) in anhydrous ethylene glycol dimethyl ether (80 mL) was added quickly to the alkoxide mixture (viii) and the resulting mixture was readily refluxed for 66 hours. The cooled reaction mixture was poured into water (200 mL) and the organic solvent was evaporated in vacuo. The residual aqueous solution was diluted with more water to a volume of 700 mL, acidified to pH 0.5 with 6M HCl aqueous solution and extracted with diethyl ether (2×600 mL). The pH of the aqueous layer was adjusted to pH 5.9 and then the aqueous solution was extracted with diethyl ether (700 mL). The organic extract was dried over sodium sulfate and the solvent was evaporated in vacuo to yield 34.0 g of the title compound (70% yield).

(x) (1R,2R)/(1S,2S)-2-(3-Ketopyrrolidinyl)-1-(2,6-dichlorophenethoxy)cyclohexane monohydrochloride: A mixture of (1R,2R)/(1S,2S)-2-[1,4-dioxa-7-azaspiro[4.4]non-7-yl]-1-(2,6-dichlorophenethoxy)cyclohexane (15.85 g, 38.9 mmol, step ix) and 6M HCl aqueous solution (100 mL) in 2-butanone (400 mL) was refluxed for 16 hours. The cooled reaction mixture was diluted with water (100 mL) and the organic solvent was evaporated in vacuo. The organic layer was further diluted with water (400 mL), extracted with diethyl ether (500 mL) and with dichloromethane (2×600 mL). The combined dichloromethane extracts were dried over sodium sulfate and the solvent was evaporated in vacuo. Azeotropic distillation with toluene provided the title compound which was further dried under high vacuum for 15 min. The hydrochloride salt was crystallized by triturating in diethyl ether, the crystals were collected and recrystallized from a mixture of ethanol-diethyl ether to yield 11.85 g of pure product (77% yield), having the elemental analysis indicated in Table 1.

Example 18

(1R,2R)/(1S,2S)-2-[1,4-dioxa-7-azaspiro[4.4]non-7-yl]-1-(1-naphthenethoxy)cyclohexane Monohydrochloride Compound #18

(1R,2R)/(1S,2S)-2-[1,4-Dioxa-7-azaspiro[4.4]non-7-yl]-1-(1-naphthenethoxy)cyclohexane (1.2 g, 3.14 mmol, from Example 15, step (viii)) in diethyl ether (80 mL) was treated with ethereal HCl. The solvent was evaporated in vacuo and the residue was taken up with diethyl ether, triturating gave a solid, which was collected and precipitated from a mixture of dichloromethane-diethyl ether to yield 0.85 g of the title compound, having the elemental analysis indicated in Table 1.

Example 19

(1R,2S)/(1S,2R)-2-(4-morpholinyl)-1-[(2-trifluoromethyl)phenethoxy]cyclohexane Monohydrochloride Compound #19

(i) 2-(4-Morpholinyl)cyclohexanone: To a chilled (−70° C.) solution of oxalyl chloride (20 mL, 0.23 mol) in dichloromethane (500 mL) was added dropwise a solution of anhydrous dimethylsulfoxide (34 mL, 0.48 mol) in dichloromethane (50 mL) and the resulting mixture was stirred for 5 min. at a temperature below −60° C. Then a solution of (1R,2R)/(1S,2S)-2-(4-morpholinyl)cyclohexanol (37.05 g, 0.2 mol) in dichloromethane (50 mL) was added dropwise in order to maintain the reaction temperature below −60° C. and the reaction mixture was stirred for 15 min. Triethylamine (140 mL) was added dropwise to the reaction mixture, keeping the reaction temperature below −50° C., and then the reaction mixture was allowed to warm up to room temperature. The reaction mixture was poured into water (600 mL) and the aqueous layer was separated and extracted with dichloromethane (2×500 mL). The combined organic layers were dried over sodium sulfate and the solvent was removed in vacuo. Vacuum distillation yielded 35.1 g (96% yield) of the title compound.

(ii) 2-(4-Morpholinyl)cyclohexanol: To a chilled (0° C.) suspension of sodium borohydride (2.14 g, 56 mmol) in isopropanol (120 mL) was added a solution of 2-(4-morpholinyl) cyclohexanol (24.7 g, 135 mmol, step i) in isopropanol (80 mL). The resulting reaction mixture was stirred at 0° C. for 10 min. and then 30 min. at ambient temperature. Water (200 mL) was added to the reaction mixture and the organic solvent was evaporated in vacuo. The residual aqueous solution was then extracted with ethyl acetate (4×50 mL), the combined organic extracts were dried over sodium sulfate and the solvent was evaporated in vacuo to yield 22.48 g of the title compound suitable for the next step without any further purification.

(iii) (1S,2R)/(1R,2S)-2-(4-Morpholinyl)cyclohexyl 2-(trifluoromethyl)phenylacetate: A mixture of 2-(4-morpholinyl) cyclohexanol (7.41 g, 40 mmol, step ii), 2-(trifluoromethyl) phenylacetic acid (10.21 g, 49 mmol) and p-toluenesulfonic acid monohydrate (40 mg) in toluene (60 mL) was refluxed in a Dean & Stark apparatus for 48 hours. To the cooled reaction mixture was added saturated sodium bicarbonate aqueous solution (40 mL), the aqueous layer was separated and extracted with ethyl acetate (3×50 mL). The combined organic layers were dried over sodium sulfate and the solvent was evaporated in vacuo to yield a mixture of (1S,2R)/(1R,2S)-2-(4-morpholinyl)cyclohexyl 2-(trifluoromethyl)phenylacetate and (1R,2R)/(1S,2S)-2-(4-morpholinyl)cyclohexyl 2-(trifluoromethyl)phenylacetate. Chromatography by dry column of the cis/trans mixture with mixtures of ethyl acetate-hexanes (+0.5% isopropylamine v/v) as eluents provided 3.19 g of the crude title compound contaminated by the starting material 2-(4-morpholinyl)cyclohexanol. The crude product was partitioned between dichloromethane (30 mL) and 0.5M HCl aqueous solution (7 mL). The aqueous layer was separated and further extracted with dichloromethane (2×18 mL). The combined organic layers were dried over sodium sulfate and the solvent was evaporated in vacuo. Recrystallization from a mixture of ethanol-hexanes yielded 2.78 g of the title compound.

(iv) (1S,2R)/(1R,2S)-2-(4-Morpholinyl)-1-[(2-trifluoromethyl)phenethoxy]cyclohexane monohydrochloride: To a mixture of (1 S,2R)/(1R,2S)-2-(4-morpholinyl)cyclohexyl 2-(trifluoromethyl)phenylacetate (1.64 g, 4.28 mmol, step iii) and sodium borohydride (332 mg, 8.70 mmol) in anhydrous tetrahydrofuran (35 mL) under reflux was added a solution of boron trifluoride diethyl etherate (8.2 mL, 65 mmol) over 1.5 hour. The reaction mixture was quenched by addition of water (~70 mL), the organic solvent was evaporated in vacuo and the pH of the residual aqueous solution was adjusted to pH 9.6. The aqueous layer was extracted with diethyl ether (2×70 mL), the combined organic extracts were dried over sodium sulfate and the solvent was evaporated in vacuo. The residue was then partitioned between 0.5M HCl aqueous solution (50 mL) and diethyl ether (2×50 mL). The aqueous solution was basified to pH 5.9 and extracted with diethyl ether (50 mL). The organic layer was collected, dried over sodium sulfate and the solvent was evaporated in vacuo to yield the crude free aminoether. The free base was converted to the hydrochloride salt by partition between 0.5M HCl aqueous solution (10 mL) and dichloromethane (10 mL). The acidic aqueous solution was extracted once more with dichloromethane (10 mL), the combined organic extracts were dried over sodium sulfate and the solvent was evaporated in vacuo. Recrystallization from a mixture of ethanol-hexanes yielded 636 mg (38% yield) of the title compound, having the elemental analysis indicated in Table 1.

Example 20

(1R,2R)/(1S,2S)-2-(3-ketopyrrolidinyl)-1-[3-(cyclohexyl)propoxy]cyclohexane Monohydrochloride Compound #20

(i) 3-Cyclohexyl-1-propyl bromide: To the chilled (0° C.) 3-cyclohexyl-1-propanol (5 g, 35.15 mmol) was added slowly a solution of phosphorus tribromide (1.1 mL, 17.6 mmol) in dichloromethane (2 mL). Upon completion of the addition, the reaction mixture was allowed to warm up to room temperature and was stirred for 4 hours. The reaction was quenched by addition of saturated sodium bicarbonate aqueous solution (5 mL) and 10% NaOH (10 mL). The resulting mixture was extracted with diethyl ether (3×50 mL), the combined organic extracts were dried over sodium sulfate and the solvent was evaporated in vacuo to provide an oil. Vacuum distillation yielded 3.4 g (47% yield) of the title compound.

(ii) (1R,2R)/(1S,2S)-2-[1,4-Dioxa-7-azaspiro[4.4]non-7-yl]-1-[3-(cyclohexyl)propoxy]cyclohexane: To a suspension of sodium hydride (200 mg, 8.33 mmol) in anhydrous dimethylformamide (20 mL) was added a solution of (1R,2R)/(1S,2S)-2-(1,4-dioxa-7-azaspiro [4.4]non-7-yl)cyclohexanol (1.5 g, 6.6 mmol) in anhydrous dimethylformamide (10 mL). The resulting mixture was stirred at room temperature for 30 min. and then a solution of 3-(cyclohexyl)propyl bromide (1.67 g, 8.15 mmols) in anhydrous dimethylformamide was quickly added. The reaction mixture was stirred at room temperature for 16 hours. The reaction mixture was poured into water (200 mL) and then extracted with ethyl acetate (3×50 mL). The combined organic extracts were back-washed with brine (50 mL) and the solvent was evaporated in vacuo. The residue was taken up with water (50 mL) and the pH was adjusted to pH 1.0 with 6M HCl aqueous solution. The acidic aqueous solution was extracted with diethyl ether (2×50 mL), then basified to pH 5.0-5.5 with 5M NaOH aqueous solution and extracted with diethyl ether (3×50 mL). The combined organic extracts at pH 5.0-5.5 were concentrated in vacuo to provide the crude title compound suitable for the next step without any further purification.

(iii) (1R,2S)/(1S,2R)-2-(3-Ketopyrrolidinyl)-1-[3-(cyclohexyl)propoxy]cyclohexane monohydrochloride: (1R,2R)/(1S,2S)-2-[1,4-Dioxa-7-azaspiro[4.4]non-7-yl]-1-[3-(cyclohexyl)propoxy]cyclohexane (ii) in a mixture of 6M HCl aqueous solution-butanone (1:4, v/v, 100 mL) was refluxed for 16 hours. The cooled reaction mixture was concentrated in vacuo and the residual aqueous solution was diluted with water (~50 mL). The acidic aqueous solution was extracted with diethyl ether (50 mL) and then with dichloromethane (3×50 mL). The dichloromethane extracts were dried over sodium sulfate and the solvent was evaporated in vacuo to provide the crude title compound. The hydrochloride salt was crystallized by triturating in a mixture of diethyl ether-hexanes (1:1, v/v, ~200 mL) and then precipitated from a mixture of dichloromethane-diethyl ether-hexanes to yield 0.8 g of the title compound, having the elemental analysis indicated in Table 1.

Example 21

(1R,2R)/(1S,2S)-2-(3-acetoxypyrrolidinyl)-1-(1-naphthenethoxy)cyclohexane Monohydrochloride Compound #21

(i) (1R,2R)/(1 S,2S)-2-(3-Hydroxypyrrolidinyl)-1-(1-naphthenethoxy)cyclohexane monohydrochloride: To a chilled (0° C.) solution of sodium borohydride in isopropanol (20 mL) was added a solution of (1R,2R)/(1S,2S)-2-(3-ketopyrrolidinyl)-1-(1-naphthenethoxy)cyclohexane monohydrochloride (1.4 g, 3.75 mmol) in isopropanol (30 mL). The resulting mixture was stirred at 0° C. for 15 min. and then 30 min. at room temperature. The reaction was quenched by addition of water, the reaction mixture was evaporated to dryness and the residue was washed with dichloromethane (2×20 mL). The dichloromethane washings were dried over sodium sulfate and the solvent was evaporated in vacuo to yield the title compound.

(ii) (1R,2R)/(1S,2S)-2-(3-Acetoxypyrrolidinyl)-1-(1-naphthenethoxy)cyclohexane monohydrochloride: The intermediate alcohol (i) was then refluxed in acetic anhydride (15 mL) for 2 hours. The excess acetic anhydride was removed in vacuo; the residue was taken up with water (100 mL) and extracted with diethyl ether (2×30 mL). The aqueous solution was basified to pH 8.0 and extracted with diethyl ether (3×50 mL). The combined organic extracts were dried over sodium sulfate and concentrated in vacuo. The residual oil was dissolved in a small amount of dichloromethane and a large volume of diethyl ether was added in order to trigger crystallization of 1.0 g (65% yield) of the title compound, having the elemental analysis indicated in Table 1.

Example 22

(1R,2R)/(1S,2S)-2-(4-morpholinyl)-1-[(2,6-dichlorophenyl)methoxy]cyclohexane Monohydrochloride Compound #22

Compound #22 was prepared according to the Williamson ether synthesis. To a suspension of sodium hydride, 80% oil dispersion (337 mg, 11 mmol) in ethylene glycol dimethyl ether (20 mL) was added a solution of (1R,2R)/(1S,2S)-2-(4-morpholinyl)-1-cyclohexanol (2.0 g, 10.8 mmol) in ethylene glycol dimethyl ether (10 mL). The resulting reaction mixture was stirred at room temperature under argon atmosphere for 3 hours, then a solution of 2,6-dichlorobenzyl bromide in ethylene glycol dimethyl ether (10 mL) was added and the reaction mixture was refluxed for 16 hours. The cooled reaction mixture was poured into water (40 mL) and the organic solvent was evaporated in vacuo. The residual aqueous solution was diluted with more water (60 mL) and acidified to pH 0.5 with 6M HCl aqueous solution. The acidic aqueous solution was extracted with diethyl ether (2×40 mL) and then the pH was adjusted to pH 5.5. Extraction with diethyl ether (3×50 mL) followed by drying over sodium sulfate and concentration in vacuo provided the pure aminoether. The hydrochloride salt was precipitated by treatment of the free base with ethereal HCl. Recrystallization from a mixture of acetone-methanol-diethyl ether yielded 2.6 g (68% yield) of the title compound, having the elemental analysis indicated in Table 1.

Example 23

(1R,2R)/(1S,2S)-2-(3-ketopyrrolidinyl)-1-[(2,6-dichlorophenyl)methoxy]cyclohexane Monohydrochloride Compound #23

Compound #23 was prepared in 7 steps according to the procedure detailed in Example 15. Steps (i) to (v) were identical to the ones described in Example 15. The ether synthesis (step vi) was carried out according to the Williamson ether synthesis as in Example #22.

(vi) (1R,2R)/(1S,2S)-2-[1,4-Dioxa-7-azaspiro[4.4]non-7-yl]-1-[(2,6-dichlorophenyl)methoxy]cyclohexane: To a suspension of sodium hydride, 80% oil dispersion (222 mg, 7.25 mmol) in ethyleneglycol dimethyl ether (20 mL) was added a solution of (1R,2R)/(1S,2S)-2-(1,4-dioxa-7-azaspiro[4.4]non-7-yl)cyclohexanol (1.5 g, 6.60 mmol, step (v) of Example 15) in ethylene glycol dimethyl ether (10 mL). The resulting mixture was stirred at room temperature for 2 hours and then a solution of 2,6-dichlorobenzyl bromide (1.9 g, 7.9 mmol) in ethylene glycol dimethyl ether (10 mL) was added. The reaction mixture was refluxed for 16 hours under argon atmosphere, the solvent was evaporated in vacuo and the residue was taken up with water (70 mL). The aqueous solution was acidified to pH 0.5 with 6M HCl aqueous solution and then extracted with diethyl ether (2×40 mL). Basification of the aqueous solution to pH 4.5-5.5, followed by extraction with diethyl ether (4×40 mL), drying of the combined organic extracts over sodium sulfate and evaporation of the solvent in vacuo provided the intermediate title compound.

(vii) (1R,2R)/(1S,2S)-2-(3-Ketopyrrolidinyl)-1-[(2,6-dichlorophenyl)methoxy]cyclohexane monohydrochloride: The ketal intermediate (step vi) in a mixture of 6M HCl-butanone (1:4, v/v, 100 mL) was refluxed for 16 hours. The butanone was evaporated in vacuo and the residual aqueous layer was diluted with more water (100 mL). The acidic aqueous layer was extracted with diethyl ether (2×40 mL) and then with dichloromethane (3×40 mL). The combined dichloromethane extracts were dried over sodium sulfate and the solvent was evaporated in vacuo to provide the crude title compound. The product was crystallized by triturating in diethyl ether and reprecipitated from a mixture of dichloromethane-diethyl ether to yield 1.8 g (72% yield) of the title compound, having the elemental analysis indicated in Table 1.

Example 24

(1R,2R)/(1S,2S)-2-(3-hydroxypyrrolidinyl)-1-(2,6-dichlorphenethoxy)cyclohexane Monohydrochloride Compound #24

To a solution of compound #17 (5.0 g, 12.7 mmol) in isopropanol (120 mL) was added sodium borohydride (2.0 g, 52.8 mmol) as a powder and the resulting mixture was stirred at room temperature until completion of the reaction. The reaction was quenched with water (40 mL) and then concentrated to dryness. The residue was washed with dichloromethane (50 mL); the filtrate was dried over sodium sulfate, concentrated in vacuo to provide the title compound, which crystallized after 3 hours under high vacuum. Elemental analysis results of the product is shown in Table 1.

Example 24A (1R,2R)/(1S,2S)-2-(3-hydroxypyrrolidinyl)-1-(3,4-dimethoxyphenethoxy)cyclohexane Monohydrochloride Compound #24A Compound #24A was prepared from (1R,2R)/(1S,2S)-2-(3-ketopyrrolidinyl)-1-(3,4-dimethoxyphenethoxy)cyclohexane by reduction with sodium borohydride in a procedure similar to that described above for Compound #24. The substrate (1R,2R)/(1S,2S)-2-(3-ketopyrrolidinyl)-1-(3,4-dimethoxyphenethoxy)cyclohexane was synthesized according to the method described in Example 17.

Spectroscopic analyses of the product are consistent with the structure for Compound #24A: $^{13}$C NMR (75 MHz, CDCl$_3$) δ 148.558, 147.255, 131.854, 131.815, 120.663, 112.249, 111.004, 79.298, 79.112, 70.959, 70.735, 69.620, 69.497, 63.276, 59.675, 59.351, 55.805, 55.712, 48.699, 48.443, 36.346, 34.326, 34.169, 28.811, 28.765, 27.090, 27.032, 23.300, 23.222, 22.921, 22.863. HR-MS: Calculated for $C_{20}H_{31}N_4O$ 349.22531, found 349.22578.

Example 25

(1R,2R)/(1S,2S)-2-(3-ketopyrrolidinyl)-1-(2,2-diphenylethoxy)cyclohexane Monohydrochloride Compound #25

Compound #25 was prepared in 10 steps according to a procedure identical to the one described in Examples 15 and 17. Steps (i) to (v) were identical to Example 15.

(vi) To a chilled (0° C.) solution of (1R,2R)/(1S,2S)-2-(1,4-dioxa-7-azaspiro[4.4]non-7-yl)cyclohexanol (2.0 g, 8.8 mmol) and triethylamine (2.1 mL, 15 mmol) in dichloromethane (30 mL) was added methanesulfonyl chloride (0.9 mL, 11.44 mmol). The reaction mixture was stirred at 0° C. for 45 min. and then at room temperature for 3 hours. The reaction mixture was diluted with dichloromethane (25 mL), washed with water (2×25 mL) and the combined washings were back-extracted with dichloromethane (25 mL). The combined organic extracts were dried over sodium sulfate and the solvent was evaporated in vacuo to yield the crude mesylate which was further pumped under high vacuum for 30 min. prior to use in step ix.

(vii) (2,2-Diphenyl)ethyl alcohol: To lithium aluminum hydride (2.85 g, 23.56 mmol) in anhydrous diethyl ether (150 mL) was added, as a powder, diphenylacetic acid (5.0 g, 56 mmol). The resulting reaction mixture was gently refluxed for one hour. The reaction was quenched with sodium sulfate saturated aqueous solution and the resulting precipitate was filtered off. The filtrate was concentrated in vacuo to yield 4.0 g (86% yield) of the title compound.

(viii) To sodium hydride, previously washed with hexanes, (253 mg, 10.56 mmol) in suspension in ethylene glycol dimethyl ether (15 mL) was added a solution of 2,2-diphenylethyl alcohol (2.09 g, 10.56 mmol, step vii) in ethylene glycol dimethyl ether (15 mL). The resulting mixture was stirred at room temperature under argon atmosphere for 30 min.

(ix) (1R,2R)/(1S,2S)-2-(1,4-Dioxa-7-azaspiro[4.4]non-7-yl)-1-(2,2-diphenylethoxy)cyclohexane: The mesylate (vi) in ethylene glycol dimethyl ether (20 mL) was added quickly to the alkoxide (viii) and the reaction mixture was refluxed for 5 days. The cooled reaction mixture was concentrated in vacuo, the residue was taken up with water (50 mL) and the pH was adjusted to pH 1.0 with 6M HCl aqueous solution. The acidic aqueous solution was extracted with diethyl ether (2×50 mL), the aqueous layer was collected and basified to pH 6.0. Extraction with diethyl ether (2×50 mL) followed by drying over sodium sulfate and evaporation of the solvent in vacuo yielded 1.55 g (43% yield) of the title compound.

(x) (1R,2R)/(1S,2S)-2-(3-Ketopyrrolidinyl)-1-(2,2-diphenylethoxy)cyclohexane monohydrochloride: A mixture of (1R,2R)/(1S,2S)-2-(1,4-dioxa-7-azaspiro[4.4]non-7-yl)-1-(2,2-diphenylethoxy)cyclohexane (1.55 g, 3.8 mmol) in 6M HCl-butanone (1:4, v/v, 50 mL) was refluxed for 2 hours. The butanone was evaporated in vacuo and the residue was taken up with water (50 mL). The aqueous solution was extracted with diethyl ether (2×50 mL); the aqueous layer was collected and extracted with dichloromethane (2×50 mL). The combined dichloromethane extracts were dried over sodium sulfate and concentrated in vacuo to yield the crude title compound. The product was crystallized by triturating in diethyl ether and reprecipitated from a mixture of dichloromethane-diethyl ether to yield 1.21 g (80% yield) of the title compound, having the elemental analysis indicated in Table 1.

Example 26

(1R,2R)/(1S,2S)-2-(3-thiazolidinyl)-1-(2,6-dichlorophenethoxy)cyclohexane Monohydrochloride Compound #26

(i) (1R,2R)/(1S,2S)-2-(3-Thiazolidinyl)cyclohexanol: To anhydrous magnesium perchlorate (12.93 g, 53.3 mmol) was added a solution of cyclohexene oxide (6.1 mL, 58.6 mmol) in anhydrous acetonitrile (25 mL) and the resulting mixture was stirred at room temperature for 20 min. Then a solution of thiazolidine (5.16 g, 55.0 mmol) in anhydrous acetonitrile was added and the reaction mixture was heated at 35° C. for 16 hours. The reaction mixture was concentrated in vacuo and the residue was partitioned between water (350 mL) and diethyl ether (350 mL). The aqueous layer was separated and extracted once more with diethyl ether (350 mL). The combined organic extracts were dried over sodium sulfate and concentrated in vacuo to provide the crude product. The crude aminoalcohol was purified by dry-column chromatography with a mixture of ethyl acetate-hexanes (1:1, v/v) as eluent to yield 4.83 g (47% yield) of the title compound.

(ii) To a chilled (0° C.) solution of (1R,2R)/(1S,2S)-2-(3-thiazolidinyl)cyclohexanol (3.17 g, 16.9 mmol) and triethylamine (3.08 mL, 22.0 mmol) in dichloromethane (30 mL) was added dropwise methanesulfonyl chloride (1.74 mL, 22.0 mmol). The reaction mixture was stirred at 0° C. for one hour and then at ambient temperature for 3 hours. The reaction mixture was diluted with dichloromethane (20 mL) and washed with water (2×30 mL). The combined washings were back-extracted with dichloromethane (25 mL) and the combined organic extracts were dried over sodium sulfate. Evaporation of the solvent in vacuo yielded the mesylate suitable for the next step without any further purification.

(iii) To sodium hydride, 80% oil dispersion (608 mg, 20.28 mmol) in ethylene glycol dimethyl ether (30 mL) was added a solution of 2,6-dichlorophenethyl alcohol (3.87 g, 20.28 mmol, example 4, step vii) in ethyleneglycol dimethyl ether (15 mL). The resulting mixture was stirred at room temperature under argon atmosphere for 2 hours.

(iv) (1R,2R)/(1S,2S)-2-(3-Thiazolidinyl)-1-(2,6-dichlorophenethoxy)cyclohexane monohydrochloride: The mesylate (ii) in ethylene glycol dimethyl ether (15 mL) was added quickly to the alkoxide (iii) and the reaction mixture was refluxed for 40 hours. The cooled reaction mixture was poured into water (100 mL) and the organic solvent was evaporated in vacuo. The residual aqueous solution was diluted with more water (100 mL) and the pH was adjusted to pH 1.5. The acidic aqueous solution was extracted with diethyl ether (3×100 mL), the combined organic extracts were dried over sodium sulfate and the solvent was removed in vacuo to provide the crude free base. The product was purified by dry-column chromatography with a mixture of ethyl acetate-hexanes (1:10, v/v) as eluent to yield 2.4 g of the crude free aminoether. The pure product (1.0 g) was converted to the hydrochloride salt by treatment with ethereal HCl and the resulting salt was recrystallized from a mixture of acetone-diethyl ether to yield 0.69 g of the title compound, having the elemental analysis indicated in Table 1.

Example 27

(1R,2S)/(1S,2R)-2-(3-Ketopyrrolidinyl)-1-(1-naphthenethoxy)cyclohexane monohydrochloride Compound #27

Compound #27 was prepared in 8 steps according to the synthetic scheme depicted in FIG. 3. Steps (i) to (iv) were identical to those described in Example 15.

(v) (1R,2R)/(1S,2S)-1-(1-Naphthenethoxy)-2-cyclohexanol: To anhydrous magnesium perchlorate (270 mg, 1.2 mmol) in anhydrous acetonitrile (1.7 mL) was added cyclohexene oxide (0.12 g, 1.2 mmol). The resulting mixture was stirred for 15 min. at room temperature and then 1-naphthenethanol (2.7 g, 10.15 mmol) was added. The reaction mixture was refluxed and more cyclohexene oxide (2.0 mL, 2.0 g, 20 mmol) was added to the refluxing reaction mixture at a rate of 0.4 mL/hour. Reflux was stopped after 16 hours and the cooled reaction mixture was partitioned between diethyl ether (50 mL) and saturated sodium bicarbonate aqueous solution (30 mL). The aqueous layer was separated and extracted twice more with diethyl ether (2×40 mL). The combined organic extracts were back-washed with water (15 mL), brine (15 mL) and dried over sodium sulfate. Evaporation of the solvent in vacuo yielded the crude title compound suitable for the next step without any further purification.

(vi) 1-(1-Naphthenethoxy)-2-cyclohexanone: To a solution of (1R,2R)/(1S,2S)-2-(1-naphthenethoxy)-1-cyclohexanol (1.0 g, step v) in dimethylformamide (20 mL) was added pyridinium dichromate (5.0 g, 13.2 mmol) in small portions and the resulting reaction mixture was stirred at room temperature for 16 hours. The reaction mixture was poured into water (100 mL) and the resulting slurry was extracted with diethyl ether (3×50 mL). The combined organic extracts were back-washed with 1M NaOH aqueous solution (30 mL), brine (30 mL) and dried over sodium sulfate. Evaporation of the solvent provided 1.0 g of the crude title compound suitable for the next step of the reaction.

(vii) (1R,2S)/(1S,2R)-2-(1,4-Dioxa-7-azaspiro[4.4]non-7-yl)-1-(1-naphthenethoxy)cyclohexane: To a solution of 1,4-dioxa-7-azaspiro[4.4]nonane (5.17 g, 40 mmol) and 1-(1-naphthenethoxy)-2-cyclohexanone (1.79 g, 6.58 mmol, step vi, 77% pure) in anhydrous methanol (10 mL) was added 5N HCl methanolic solution (2.7 mL) and then sodium cyanoborohydride (397 mg, 6 mmol). The reaction mixture was further diluted with anhydrous methanol (7 mL) and stirred at room temperature for 16 hours. The reaction mixture was quenched by addition of 6M HCl aqueous solution (40 mL), the organic solvent was evaporated in vacuo, the residual aqueous solution was diluted to 100 mL with water and the pH was adjusted to pH 0.5 with 6M HCl aqueous solution. The acid aqueous layer was extracted with diethyl ether (100 mL); the aqueous layer was separated and basified to pH 6.7 with 5M NaOH aqueous solution. Extraction with diethyl ether (100 mL), followed by drying over sodium sulfate and evaporation of the solvent in vacuo provided, after purification by dry-column chromatography with mixtures of ethyl acetate-hexanes (1:9 to 1:6, v/v, +0.5% v/v isopropylamine) as eluents, 1.28 g of crude (1R,2S)/(1S,2R)-2-(1,4-dioxa-7-azaspiro[4.4]non-7-yl)-1-(1-naphthenethoxy)cyclohexane and (1R,2R)/(1S,2S)-2-(1,4-dioxa-7-azaspiro[4.4]non-7-yl)-1-(1-naphthenethoxy)cyclohexane. Separation of (1R,2S)/(1S,2R)-2-(1,4-dioxa-7-azaspiro[4.4]non-7-yl)-1-(1-naphthenethoxy)cyclohexane from (1R,2R)/(1S,2S)-2-(1,4-dioxa-7-azaspiro[4.4]non-7-yl)-1-(1-naphthenethoxy)cyclohexane was performed by preparative HPLC (Waters Delta Prep 4000, PrePak cartridge 40×100 mm, isopropanol-hexanes (2:98, v/v, +0.05% v/v diethylamine)) to yield 590 mg of the title compound.

viii) (1R,2S)/(1S,2R)-2-(3-Ketopyrrolidinyl)-1-(1-naphthenethoxy)cyclohexane monohydrochloride: A mixture of (1R,2S)/(1S,2R)-2-(1,4-dioxa-7-azaspiro[4.4]non-7-yl)-1-(1-naphthenethoxy)cyclohexane (480 mg, 1.23 mmol, step vii) in 6M HCl aqueous solution-butanone (1:4, v/v, 40 mL) was refluxed for 2 hours. The organic solvent was evaporated in vacuo, the residual aqueous solution was diluted to 50 mL with water and extracted twice with diethyl ether (2×50 mL) and then thrice with dichloromethane (3×50 mL). The combined dichloromethane extracts were dried over sodium sulfate and the solvent was evaporated in vacuo, the residual oil was further dried by azeotropic distillation of toluene. The title compound was crystallized by triturating in hexanes (430 mg, 93% yield), and has elemental analysis indicated in Table 1.

TABLE 1

| Compound | Formula | Calculated | Found |
|---|---|---|---|
| #1 | $C_{22}H_{30}NO_2Cl$ | C 70.29, H 8.04, N 3.73% | C 69.36, H 8.17, N 3.73% |

TABLE 1-continued

| Compound | Formula | Calculated | Found |
|---|---|---|---|
| #2 | $C_{22}H_{30}NO_2Cl$ | C 70.29, H 8.04, N 3.73% | C 69.78, H 8.06, N 3.56% |
| #3 | $C_{18}H_{27}NO_2BrCl$ | C 53.41, H 6.72, N 3.46% | C 53.16, H 6.77, N 3.35% |
| #4 | $C_{22}H_{30}NO_3Cl$ | C 67.42, H 7.72, N 3.57% | C 67.31, H 7.75, N 3.59% |
| #5 | $C_{18}H_{27}NO_3BrCl$ | C 51.38, H 6.47, N 3.33% | C 51.38, H 6.21, N 3.28% |
| #6 | $C_{20}H_{32}NO_4Cl$ | C 62.24, H 8.36, N 3.63% | C 61.69, H 8.64, N 3.63% |
| #7 | $C_{22}H_{30}NOCl$ | C 73.41, H 8.40, N 3.89% | C 73.26, H 8.64, N 3.94% |
| #8 | $C_{20}H_{28}NO_2SCl$ | C 62.89, H 7.39, N 3.67% | C 61.94, H 7.42, N 3.70% |
| #9 | $C_{20}H_{28}NO_2SCl$ | C 62.89, H 7.39, N 3.67% | C 62.53, H 7.56, N 3.64% |
| #10 | $C_{18}H_{27}NO_2BrCl$ | C 53.41, H 6.72, N 3.46% | C 53.29, H 6.94, N 3.57% |
| #11 | $C_{18}H_{27}NO_2BrCl$ | C 53.41, H 6.72, N 3.46% | C 52.61, H 7.46, N 4.01% |
| #12 | $C_{21}H_{34}NO_4Cl$ | C 63.06, H 8.57, N 3.50% | C 62.45, H 8.41, N 3.45% |
| #14 | $C_{18}H_{26}NO_2Cl_3$ | C 54.77, H 6.64, N 3.55% | C 58.80, H 6.85, N 3.51% |
| #15 | $C_{22}H_{28}NO_2Cl$ | C 70.67, H 7.55, N 3.75% | C 70.12, H 7.55, N 3.73% |
| #16 | $C_{24}H_{33}N2O_2Cl \cdot H_2O$ | C 63.63, H 8.23, N 6.18% | C 62.93, H 8.56, N 6.05% |
| #17 | $C_{18}H_{24}NO_2Cl_3$ | C 55.05, H 6.16, N 3.57% | C 54.39, H 6.30, N 3.49% |
| #18 | $C_{24}H_{32}NO_3Cl$ | C 68.97, H 7.72, N 3.35% | C 68.49, H 7.64, N 3.31% |
| #19 | $C_{19}H_{27}NO_2ClF_3$ | C 57.94, H 6.91, N 3.56% | C 57.75, H 6.91, N 3.56% |
| #20 | $C_{19}H_{34}NO_2Cl$ | C 66.35, H 9.96, N 4.07% | C 66.22, H 9.72, N 4.12% |
| #21 | $C_{24}H_{32}NO_3Cl$ | C 68.97, H 7.72, N 3.35% | C 67.52, H 7.99, N 3.17% |
| #22 | $C_{17}H_{24}NO_2Cl_2 \cdot H_2O$ | C 51.21, H 6.57, N 3.51% | C 51.03, H 6.57, N 3.36% |
| #23 | $C_{17}H_{22}NO_2Cl_2$ | C 53.91, H 5.86, N 3.70% | C 53.88, H 5.79, N 3.59% |
| #24 | $C_{18}H_{26}NO_2Cl_3 \cdot H_2O$ | C 52.38, H 6.84, N 3.39% | C 53.98, H 7.24, N 3.33% |
| #25 | $C_{24}H_{30}NO_2Cl$ | C 72.07, H 7.56, N 3.50% | C 71.87, H 7.57, N 3.51% |
| #26 | $C_{17}H_{24}NOCl_3S$ | C 51.46, H 6.10, N 3.53% | C 51.48, H 5.86, N 3.44% |
| #27 | $C_{22}H_{28}NO_2Cl$ | C 70.67, H 7.55, N 3.75% | C 70.63, H 7.53, N 3.65% |

Example 28

Assessment of Antiarrhythmic Efficacy

Antiarrhythmic efficacy was assessed by investigating the effect of a compound on the incidence of cardiac arrhythmias in conscious rats subject to coronary artery occlusion. Rats weighing 200-300 gms were subjected to preparative surgery and assigned to groups in a random block design. In each case, the animal was anesthetized with halothane during surgical preparation. The left femoral artery was cannulated for measurement of mean arterial blood pressure and withdrawal of blood samples. The left femoral vein was also cannulated for injection of drugs. The thoracic cavity was opened and a polyethylene occluder loosely placed around the left anterior descending coronary artery. The thoracic cavity was then closed. ECG was recorded by insertion of electrodes placed along the anatomical axis of the heart. All cannulae and electrode leads were exteriorized in the mid scapular region.

In a random and double-blind manner, about 0.5 to 2 hours post-surgery, an infusion of vehicle, or the compound to be tested was given. After 15 minutes infusion, the occluder was pulled so as to produce coronary artery occlusion. ECG, arrhythmias, blood pressure, heart rate and mortality were monitored for 30 minutes after occlusion. Arrhythmias were recorded as ventricular tachycardia (VT) and ventricular fibrillation (VF) and scored according to Curtis, M. J. and Walker, M. J. A., Cardiovasc. Res. 22:656 (1988) (see Table 2).

TABLE 2

| Score | Description |
|---|---|
| 0 | 0-49 VPBs |
| 1 | 50-499 VPBs |
| 2 | >499 VPBs and/or 1 episode of spontaneously reverting VT or VF |
| 3 | >1 episode of VT or VF or both (>60 s total combined duration) |
| 4 | VT or VF or both (60-119 s total combined duration) |
| 5 | VT or VF or both (>119 s total combined duration) |
| 6 | fatal VF starting at >15 min after occlusion |
| 7 | fatal VF starting at between 4 min and 14 min 59 s after occlusion |
| 8 | fatal VF starting at between 1 min and 3 min 59 s after occlusion |
| 9 | fatal VF starting <1 min after occlusion |

Where:
VPB = ventricular premature beats
VT = ventricular tachycardia
VF = ventricular fibrillation Rats were excluded from the study if they did not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Table 3 describes the result of tests of the compounds described therein as values of a given infusion rate in micromol/kg/min. ($ED_{50}AA$) which will reduce the arrhythmia score in treated animals to 50% of that shown by animals treated only with the vehicle in which the test drug(s) is dissolved.

TABLE 3

| Compound | $ED_{50}AA$ |
|---|---|
| #1 | 0.8 |
| #2 | 1.0 |
| #3 | 2.1 |
| #4 | 2.0 |
| #5 | 3.0 |
| #6 | 4.0 |
| #7 | 4.0 |
| #8 | 1.0 |
| #9 | 1.0 |
| #10 | 2.0 |
| #11 | 1.0 |
| #14 | 1.5 |
| #15 | 0.43 |
| #17 | 1.1 |
| #19 | 1.4 |
| #21 | 1.4 |
| #22 | 1.8 |
| #23 | 2.1 |
| #24 | 0.6 |
| #25 | 2.5 |
| #26 | 6.5 |

Example 29

Measurement of ECG Parameters

Rats weighing 200-250 gms were used in this example. Animals were anesthetized with 60 mg/kg pentobarbitone i.p. The carotid artery and jugular vein were cannulated for measurement of blood pressure and drug injection, respectively. ECG was recorded by insertion of electrodes placed along the anatomical axis of the heart. All compounds were given as bolus injections.

Various ECG parameters were measured. Table 4 describes the results of the tests as $ED_{25}$ (micromol/kg) which are the doses required to produce a 25% increase in the parameter measured (ne=not estimated). The increases in P-R interval and QRS interval indicate cardiac sodium channel blockage while the increase in Q-T interval indicates ancillary cardiac potassium channel blockage which is the property of a type 1a antiarrhythmic.

TABLE 4

| Compound | PR | QRS | QT |
|---|---|---|---|
| #1 | NE | NE | 2.5 |
| #2 | 5.6 | 8 | 2.0 |
| #3 | 32 | 16 | 3.0 |
| #6 | NE | NE | NE |
| #7 | 1.1 | 1.5 | 0.9 |
| #14 | — | 21.5 | 1.4 |
| #15 | 15.8 | 7.8 | 3.4 |
| #17 | 30 | 26 | 4.2 |
| #21 | 1.7 | 2.3 | 1.6 |
| #23 | — | 17.2 | 2.7 |
| #24 | 1.4 | 1.6 | 1.0 |
| #26 | 2.3 | — | 10 |

Example 30

Assessment of Sodium Channel Blockage

Rats were prepared according to the preceding procedure. Two silver stimulating electrodes were inserted through the chest wall and implanted in the left ventricle. Square wave stimulation was used to determine threshold current for capture, ventricular fibrillation threshold current, and effective refractory period (Howard, P. G. and Walker, M. J. A., Proc. West. Pharmacol. Soc. 33:123-127 (1990)). Table 5 contains $ED_{25}$ values for these indices of cardiac sodium channel blockage, where the $ED_{25}$ is the infusion rate in micromol/kg/minute of compound required to elicit a 25% increase from control. The increases in refractoriness indicate ancillary blockage of potassium channels. The threshold current for capture is represented by "It". The fibrillation threshold current is represented by "VFT". The effective refracting period is represented by "ERP".

TABLE 5

| Compound | It | VFT | ERP |
|---|---|---|---|
| #1 | 2.8 | 1.4 | 1.5 |
| #2 | 0.9 | 0.7 | 1.3 |
| #3 | 5.8 | NE | 4.0 |
| #7 | 0.7 | 0.2 | 0.4 |
| #14 | 6.4 | — | 1.7 |
| #15 | 5 | 1.2 | 1.6 |
| #17 | 6 | 7.3 | 7.1 |
| #23 | 7.6 | 6.2 | 5 |
| #24 | 1.7 | 1.2 | 1.1 |

TABLE 5-continued

| Compound | It | VFT | ERP |
|---|---|---|---|
| #26 | 10.5 | 9 | 5.4 |

Example 31

Canine Vagal-AF Model

General Methods

Mongrel dogs of either sex weighing 15-49 kg were anesthetized with morphine (2 mg/kg im initially, followed by 0.5 mg/kg IV every 2 h) and α-chloralose (120 mg/kg IV followed by an infusion of 29.25 mg/kg/h; St.-Georges et al., 1997). Dogs were ventilated mechanically with room air supplemented with oxygen via an endrotracheal tube at 20 to 25 breaths/minute with a tidal volume obtained from a nomogram. Arterial blood gases were measured and kept in the physiological range ($SAO_2$>90%, pH 7.30-7.45). Catheters were inserted into the femoral artery for blood pressure recording and blood gas measurement, and into both femoral veins for drug administration and venous sampling. Catheters were kept patent with heparinized 0.9% saline solution. Body temperature was maintained at 37-40° C. with a heating blanket.

The heart was exposed via a medial thoracotomy and a pericardial cradle was created. Three bipolar stainless steel, Teflon™-coated electrodes were inserted into the right atria for recording and stimulation, and one was inserted into the left atrial appendage for recording. A programmable stimulator (Digital Cardiovascular Instruments, Berkeley, Calif.) was used to stimulate the right atrium with 2 ms, twice diastolic threshold pulses. Two stainless steel, Teflon™-coated electrodes were inserted into the left ventricle, one for recording and the other for stimulation. A ventricular demand pacemaker (GBM 5880, Medtronics, Minneapolis, Minn.) was used to stimulate the ventricles at 90 beats/minute when (particular during vagal-AF) the ventricular rate became excessively slow. A P23 ID transducer, electrophysiological amplifier (Bloom Associates, Flying Hills, Pa.) and paper recorder (Astromed MT-95000, Toronto, ON, Canada) were used to record ECG leads II and III, atrial and ventricular electrograms, blood pressure and stimulation artefacts. The vagi were isolated in the neck, doubly-ligated and divided, and electrodes inserted in each nerve (see below). To block changes in β-adrenergic effects on the heart, nadolol was administered as an initial dose of 0.5 mg/kg iv, followed by 0.25 mg/kg IV every two hours.

Atrial Fibrillation Model

Drug effects to terminate sustained AF maintained during continuous vagal nerve stimulation were assessed. Unipolar hook electrodes (stainless steel insulated with Teflon™, coated except for the distal 1-2 cm) were inserted via a 21 gauge needle within and parallel to the shaft of each nerve. In most experiments, unipolar stimuli were applied with a stimulator (model DS-9F, Grass Instruments, Quincy, Mass.) set to deliver 0.1 ms square-wave pulses at 10 Hz and a voltage 60% of that required to produce asystole. In some experiments, bipolar stimulation was used. The voltage required to produce asystole ranged between 3-20 volts. Under control conditions, a short burst of rapid atrial pacing (10 Hz, four times diastolic threshold) was delivered to induce AF which was ordinarily sustained for more than 20 minutes. The vagal stimulation voltage was adjusted under control conditions, and then readjusted after each treatment to maintain the same bradycardic effect. AF was defined as rapid (>500 minute under control conditions), irregular atrial rhythm with varying electrogram morphology.

Measurement of Electrophysiological Variables and Vagal Response

Diastolic threshold current was determined at a basic cycle length of 300 ms by increasing the current 0.1 mA incrementally until stable capture was obtained. For subsequent protocols current was set to twice diastolic threshold. Atrial and ventricular ERP was measured with the extrastimulus method, over a range of S1 S2 intervals at a basic cycle length of 300 ms. A premature extrastimulus S2 was introduced every 15 basic stimuli. The S1 S2 interval was increased in 5 ms increments until capture occurred, with the longest S1S2 interval consistently failing to produce a propagated response defining ERP. Diastolic threshold and ERP were determined in duplicate and averaged to give a single value. These values were generally within 5 ms. The interval between the stimulus artefact and the peak of the local electrogram was measured as an index of conduction velocity. AF cycle length (AFCL) was measured during vagal-AF by counting the number of cycles (number of beats–1) over a 2-second interval at each of the atrial recording sites. The three AFCLs measurements were averaged to obtain an overall mean AFCL for each experimental condition.

The stimulus voltage-heart rate relationship for vagal nerve stimulation was determined under control conditions in most experiments. The vagal nerves were stimulated as described above with various voltages to determine the voltage which caused asystole (defined as a sinus pause greater than 3 seconds). The response to vagal nerve stimulation was confirmed under each experimental condition and the voltage adjusted to maintain the heart rate response to vagal nerve stimulation constant. In cases in which is was not possible to produce asystole, vagal nerve stimulation was adjusted to a voltage which allowed two 20-minute episodes of vagal-AF to be maintained under control conditions (see below).

Experimental Protocols

The experimental groups studied are summarized in Table 5. Each dog received only one drug at doses indicated in Table 5. The first series of experiments were dose ranging studies, followed by blinded study in which 1-3 doses were given. All drugs were administered IV via an infusion pump, with drug solutions prepared freshly in plastic containers on the day of the experiment. Vagal stimulation parameters were defined under control conditions as described above, and maintenance of AF during 20 minutes of vagal nerve stimulation under control conditions was verified. After the termination of AF, the diastolic threshold and ERP of the atrium and ventricle were determined. Subsequently, these variables were reassessed in the atrium under vagal nerve stimulation. Electrophysiological testing usually took 15-20 minutes. The heart rate response to vagal nerve stimulation was confirmed and the vagal-AF/electrophysiological testing protocol was repeated. A pre-drug blood sample was obtained and vagal-AF reinstituted. Five minutes later, one of the treatments was administered at doses shown in Table 5. The total dose was infused over 5 minutes and a blood sample obtained immediately thereafter. No maintenance infusion was given. If AF terminated within 15 minutes, the electrophysiological measurements obtained under control conditions were repeated and a blood sample was obtained. If AF was not terminated by the first dose (within 15 minutes), a blood sample was obtained and vagal stimulation was discontinued to allow a return to sinus rhythm. The electrophysiological measurements were repeated and a third and final blood sample for this dose was obtained. AF was reinitiated and the vagal-AF/ drug infusion/electrophysiological testing protocol was repeated until AF was terminated by the drug.

Statistical Analysis

Group data are expressed as the mean ±SEM. Statistical analysis was carried out for effective doses for AFCL, and ERP using a t-test with a Bonferroini correction for multiple comparisons. Drug effects on blood pressure, heart rate, diastolic threshold and ECG intervals were assessed at the median dose for termination of AF. Two tailed tests were used and a $p<0.05$ was taken to indicate statistical significance.

TABLE 6

EXPERIMENTAL GROUPS AND DOSES OF DRUGS

| Drug | Dose range tested (μmol/kg) | Effective doses for terminating AF (μmol/kg) | Mean dose required for termination of AF (μmol/kg) | Median dose required for termination of AF (μmol/kg) |
|---|---|---|---|---|
| Flecainide | 1.25-10 | 4-2.5; 1-10 | 4 ± 2 | 2.5 |

A single drug was administered to each dog over the dose range specified until AF was terminated. The number of dogs in which AF was terminated at each dose is shown (number of dogs-dose, in μmol/kg). The mean ±SEM as well as the median dose required to terminate AF is shown. Each dog received only one drug.

A number of the compounds of the present invention have been evaluated by this method. The results showed that all of the compounds tested are effective in terminating AF in the canine vagal-AF model. The conversion rates are similar to those reported for a variety of other class I and III drugs in this model. The effectiveness of flecainide as a control in the present study was comparable to that previously reported. All of the drugs prolonged AFCL prior to termination of AF; effects which are globally consistent with the wave length of re-entry model for termination of AF. The tested compounds of the present invention did not reduce blood pressure or heart rate at the median dose for termination of vagal-AF. The heart rate response to vagal nerve stimulation was similar in all groups and was not influenced by any of the compounds tested. Vagal nerve stimulation at 60% of the voltage required to produce asystole (10±1 V) produced a 1.3±0.1 second pause.

Example 32

Canine Sterile Pericarditis Model

This model has been used to characterize the mechanisms of AF and atrial flutter (AFL). Waldo and colleagues have found that AF depends on reentry and that the site of termination is usually an area of slowed conduction. This canine model is prepared by dusting the exposed atria with talcum powder followed by "burst" pacing the atria over a period of days after recovery. AF is inducible two days after surgery, however, by the fourth day after surgical preparation; sustainable atrial flutter is the predominant inducible rhythm. The inducibility of AF at day 2 is somewhat variable, such that only 50% of dogs may have sustained AF (generally <60 minutes) for a requisite of 30 minutes. However, the sustainable atrial flutter that evolves by the fourth day is inducible in most preparations. Atrial flutter is more readily "mapped" for purposes of determining drug mechanisms. Inducibility of AF subsides after the fourth day post-surgery, similar to the AF that often develops following cardiac surgery that the sterile pericarditis model mimics. There may be an inflammatory component involved in the etiology of post-surgery AF that would provide a degree of selectivity to an ischaemia or acid selective drug. Similarly, while coronary artery bypass graft (CABG) surgery is performed to alleviate ventricular ischaemia, such patients may also be at risk for mild atrial ischaemia due to coronary artery disease (CAD). While atrial infarcts are rare, there has been an association between AV nodal artery stenosis and risk for AF following CABG surgery. Surgical disruption of the autonomic innervation of the atria may also play a role in AF following CABG.

Methods

Studies were carried out in a canine model of sterile pericarditis to determine the potency and efficacy of Compound 1 in terminating atrial fibrillation/flutter. Atrial flutter or fibrillation was induced 2 to 4 days after creation of sterile pericarditis in adult mongrel dogs weighing 19 kg to 25 kg. In all instances, the atrial fibrillation or flutter lasted longer than 10 minutes. All studies were performed in accordance with guidelines specified by our Institutional Animal Care and Use Committee, the American Heart Association Policy on Research Animal Use, and the Public Health Service Policy on Use of Laboratory Animals.

Creation of the Sterile Pericarditis Atrial Fib/Flutter Model

The canine sterile pericarditis model was created as previously described. At the time of surgery, a pair of stainless steel wire electrodes coated with FEP polymer except for the tip (O Flexon, Davis and Geck) were sutured on the right atrial appendage, Bachman's bundle and the posteroinferior left atrium close to the proximal portion of the coronary sinus. The distance between each electrode of each pair was approximately 5 mm. These wire electrodes were brought out through the chest wall and exteriorized posteriorly in the interscapular region for subsequent use. At the completion of surgery, the dogs were given antibiotics and analgesics and then were allowed to recover. Postoperative care included administration of antibiotics and analgesics.

In all dogs, beginning on postoperative day 2, induction of stable atrial fibrillation/flutter was attempted in the conscious, non-sedated state to confirm the inducibility and the stability of atrial fib/flutter and to test the efficacy of the drugs. Atrial pacing was performed through the electrodes sutured during the initial surgery. On postoperative day 4, when stable atrial flutter was induced, the open-chest study was performed.

For the open-chest study, each dog was anesthetized with pentobarbital (30 mg/kg IV) and mechanically ventilated with 100% oxygen by use of a Boyle model 50 anesthesia machine (Harris-Lake, Inc.). The body temperature of each dog was kept within the normal physiological range throughout the study with a heating pad. With the dog anesthetized, but before the chest was opened, radiofrequency ablation of the His bundle was performed to create complete atrioventricular (AV) block by standard electrode catheter techniques. This was done to minimize the superimposition of atrial and ventricular complexes during subsequent recordings of unipolar atrial electrograms after induction of atrial flutter. After complete AV block was created, an effective ventricular rate was maintained by pacing of the ventricles at a rate of 60 to 80 beats per minute with a Medtronic 5375 Pulse Generator (Medtronic Inc.) to deliver stimuli via the electrodes sutured to the right ventricle during the initial surgery.

Determination of Stimulus Thresholds and Refractory Periods During Pacing

For the induction of AF/AFL, one of two previously described methods was used: (1) introduction of one or two premature atrial beats after a train of 8 paced atrial beats at a cycle length of 400 ms, 300 ms, 200 ms, or 150 ms, or (2) rapid atrial Pacing for Periods of 1 to 10 seconds at rates incrementally faster by 10 to 50 beats per minute than the spontaneous sinus rate until atrial flutter was induced or there was a loss of 1:1 atrial capture. Atrial pacing was performed from either the right atrial appendage electrodes or the posteroinferior left atrial electrodes. All pacing was performed using stimuli of twice threshold for each basic drive train with a modified Medtronic 5325 programmable, battery-powered stimulator with a pulse width of 1.8 ms.

After the induction of stable atrial fib/flutter (lasting longer than 10 minutes), the atrial fib/flutter cycle length was measured and the initial mapping and analysis were performed to determine the location of the atrial fib/flutter reentrant circuit. Atrial flutter was defined as a rapid atrial rhythm (rate, >240 beats per minute) characterized by a constant beat-to-beat cycle length, polarity, morphology, and amplitude of the recorded bipolar electrograms.

Drug Efficacy Testing Protocol

1. Effective refractory periods (ERPs) were measured from three sites: right atrial appendage (RAA), posterior left atrium (PLA), and Bachman's Bundle (BB), at two basic cycle lengths 200 and 400 ms.
2. Pace induce A-Fib or AFL. This was attempted for one hour. If no arrhythmia was induced, no further study was done on that day.
3. If induced, AF must have been sustained for 10 minutes. Then a waiting period was allowed for spontaneous termination or 20 minutes, whichever came first.
4. AF was then reinduced and 5 minutes was allowed before starting drug infusion.
5. Drug was then infused in a bolus over 5 minutes.
6. If AF terminated with the first dose then a blood sample was taken and ERP measurements were repeated.
7. Five minutes was allowed for the drug to terminate. If there was no termination then the second dose was given over 5 minutes.
8. After termination and ERPs were measured, a second attempt to reinduce AF was tried for a period of ten minutes.
9. If reinduced and sustained for 10 minutes, a blood sample was taken and the study repeated from #3 above.
10. If no reinduction, then the study was over.

A number of the compounds of the present invention have been evaluated by this method. The results showed that all of the compounds tested are effective in terminating episodes of atrial fibrillation/flutter in this model. There was no proarrhythmia or cardiovascular adverse events observed during drug treatment.

Example 33

In Vitro Assessment of Inhibition Activity of Ion Channel Modulating Compounds on Different Cardiac Ion Currents Cell Culture:

The relevant cloned cardiac ion channels (e.g. Kv1.4, Kv1.5, Kv4.2, Kv2.1 etc.) were studied by transient transfection into HEK cells using the mammalian expression vector pcDNA3. Transfections for each channel type were carried out separately to allow individual study of the ion channel of interest. Cells expressing channel protein were detected by cotransfecting cells with the vector pHook-1 (Invitrogen, San Diego, Calif., USA). This plasmid encoded the production of an antibody to the hapten phOX, which when expressed is displayed on the cell surface. Equal concentrations of individual channel and pHook DNA were incubated with 10× concentration of lipofectAce in Modified Eagle's Medium (MEM, Canadian Life Technologies) and incubated with parent HEK cells plated on 25 mm culture dishes. After 3-4 hours the solution was replaced with a standard culture medium plus 20% fetal bovine serum and 1% antimycotic. Transfected cells were maintained in at 37° C. in an air/5% $CO_2$ incubator in 25 mm Petri dishes plated on glass coverslips for 24-48 hours to allow channel expression to occur. 20 min prior to experiments, cells were treated with beads coated with phOX. After 15 min, excess beads were washed off with cell culture medium and cells which had beads stuck to them were used for electrophysiological tests.

Solutions:

For whole-cell recording the control pipette filling solution contained (in mM): KCl, 130; EGTA, 5; MgCl2, 1; HEPES, 10; Na2ATP, 4; GTP, 0.1; and was adjusted to pH 7.2 with KOH. The control bath solution contained (in mM): NaCl, 135; KCl, 5; sodium acetate, 2.8; MgCl2, 1; HEPES, 10; CaCl2, 1; and was adjusted to pH 7.4 with NaOH. A low pH bath solution contained the same constituents as control bath, but pH was adjusted to 6.4 using NaOH. All chemicals were from Sigma Chemical Co. (St-Louis, Mo.). The test ion channel modulating compound was dissolved to 10 mM stock solutions in water and used at concentrations between 0.5 and 100 uM. All compounds were protected from the light during all experiments.

Electrophysiological Procedures:

Coverslips containing cells were removed from the incubator before experiments and placed in a superfusion chamber (volume 250 µl) containing the control bath solution at 22° C. to 23° C. All recordings were made via the variations of the patch-clamp technique, using an Axopatch 200A amplifier (Axon Instruments, CA). Patch electrodes were pulled from thin-walled borosilicate glass (World Precision Instruments; FL) on a horizontal micropipette puller, fire-polished, and filled with appropriate solutions. Electrodes had resistances of 1.0-2.5 µohm when filled with control filling solution. Analog capacity compensation was used in all whole cell measurements. In some experiments, leak subtraction was applied to data. Membrane potentials have not been corrected for any junctional potentials that arose between the pipette and bath solution. Data were filtered at 5 to 10 kHz before digitization and stored on a microcomputer for later analysis using the pClamp6 software (Axon Instruments, Foster City, Calif.). Due to the high level of expression of channel cDNA's in HEK cells, there was no need for signal averaging. The average cell capacitance was quite small, and the absence of ionic current at negative membrane potentials allowed faithful leak subtraction of data.

Data Analysis:

The concentration-response curves for changes in peak and steady-state current produced by the test compound were computer-fitted to the Hill equation:

$$f=1-1/[1+(IC50/[D])^n] \quad [1]$$

where f is the fractional current (f=Idrug/Icontrol) at drug concentration [D]; IC50 is the concentration producing half-maximal inhibition and n is the Hill coefficient. The rapid component of inactivation induced by the test compound was much faster than that observed in the absence of drug. Therefore, we used this drug induced time-constant ($\tau_{block}$) as an approximation of the drug channel interaction kinetics, according to the equation:

$$1/\tau_{block}=k_{+1}[D]+k_{-1} \quad [2a]$$

$$\text{and } Kd=k_{-1}/k_{+1} \quad [2b]$$

in which $\tau_{block}$ is the current decay time constant caused by the drug; [D] is the concentration of drug; $k_{+1}$ and $k_{-1}$ are the apparent rate constants of binding and unbinding for the drug, respectively. The voltage dependence of block for the uncharged drug was determined as follows: leak-corrected current in the presence of drug was normalized to matching control at each voltage above −20 mV. Using data points in the range of full channel opening ($\geq$+20 mV), we have calculated the fractional block (f=Idrug/Icontrol) at each potential and fitted data to the Woodhull equation:

$$f=[D]/([D]+Kd^*\cdot e^{-qzFE/RT}) \qquad [3]$$

where f, R, z and T have their usual meanings, q represents the fractional electrical distance, i.e., the fraction of the transmembrane electrical field sensed by a single charge at the receptor site. Kd* represents the binding affinity at the reference voltage (0 mV). Experimental values are given as means ±S.E. or S.D. as stated.

A number of the compounds of the present invention have been evaluated by this method. The results showed that the compounds of the present invention tested are effective in blocking the various cardiac ion channels. There are different dose responses in the activity to block the various cardiac currents for the different compounds tested.

Example 34

Assessment of Proarrhythmia (Torsade de Pointes) Risk of Ion Channel Modulating Compounds in Primates These experiments were carried out in Bogor, Indonesia. Experimental protocols and procedures were approved by the ethics review committee at Lembaga Penelitial Institut Pertainian Bogor, Indonesia.

Methods

General Surgical Preparation:

All studies were carried out in male *Macaca fascicularis* weighing between 4 and 5.5 kg. Animals were fasted over night and pre-medicated with ketamine (10 mg/kg im). Both saphenous veins were cannulated and a saline drip instituted to keep the lines patent. Halothane anaesthesia (1.5% in oxygen) was administered via a face mask. Lidocaine spray (10% spray) was used to facilitate intubation. After achieving a sufficient depth of anaesthesia, animals were intubated with a 4 or 5 French endotracheal tube. After intubation halothane was administered via the endotracheal tube and the concentration was reduced to 0.75-1%. Artificial respiration was not used and all animals continued to breathe spontaneously throughout the experiment. Blood gas concentrations and blood pH were measured using a blood gas analyser (AVO OPTI I). The femoral artery was cannulated to record blood pressure.

Blood pressure and a modified lead II ECG were recorded using a MACLAB 4S recording system paired with a Macintosh PowerBook (2400c/180). A sampling rate of 1 kHz was used for both signals and all data was archived to a Jazz disc for subsequent analysis.

Vagal Nerve Stimulation:

Either of the vagi was isolated by blunt dissection and a pair of electrodes inserted into the nerve trunk. The proximal end of the nerve was crushed using a vascular clamp and the nerve was stimulated using square wave pulses at a frequency of 20 Hz with a 1 ms pulse width delivered from the MACLAB stimulator. The voltage (range 2-10V) was adjusted to give the desired bradycardic response. The target bradycardic response was a reduction in heart rate by half. In cases where a sufficient bradycardic response could not be obtained, 10 µg/kg neostigmine iv was administered. This dose of neostigmine was also given after administration of the test drug in cases where the test drug had vagolytic actions.

Test Compounds:

The test compounds were transported to Bogor, Indonesia on dry ice. A near maximum tolerated bolus dose of the test compound, infused (iv) over 1 minute, was used to assess the risk of torsade de pointes caused by each ion channel modulating compound. The actual doses varied slightly depending on the animals weight. Clofilium, 30 µmol/kg, was used as a positive comparison (control) for these studies. The expectation was that a high dose of drug would result in a high incidence of arrhythmias. The test compounds were dissolved in saline immediately before administration.

The necessity of vagal nerve stimulation for the model was assessed by administering 2 mg/kg clofilium iv without stimulating the vagal nerve. Animals included in this experiment had previously received the same test compound 2-5 days prior to the experiment.

Experimental Protocol:

Each animal received a single dose of a given drug iv. Before starting the experiment two, 30 second episodes of vagal nerve stimulation were recorded. A five minute rest period was allowed between episodes and before starting the experiment. The test solution was administered as an iv bolus at a rate of 5 ml/minute for 1 minute using an infusion pump (total volume 5 ml). ECG and blood pressure responses were monitored continuously for 60 minutes and the occurrence of arrhythmias was noted. The vagal nerve was stimulated for 30 seconds at the following times after injection of the drug: 30 seconds, 2, 5, 10, 15, 20, 25, 30 and 60 minutes.

Blood samples (1 ml total volume) were taken from each treated animal at the following times after drug administration: 30 seconds, 5, 10, 20, 30 and 60 minutes as well as 3, 6, 24 and 48 hours. Blood samples taken up to 60 minutes after drug administration were arterial while those taken after this time were venous. Samples were centrifuged, the plasma decanted and frozen. Samples were kept frozen before analysis of plasma concentration of the drug and potassium.

Statistics:

The effect of drugs on blood pressure, heart rate and ECG intervals are described as the mean ±SEM for a group size of "n."

A number of the compounds of the present invention have been evaluated by this method. No proarrhythmia or cardiovascular adverse events were detected.

Example 35

Assessment of Pain Blockage

Guinea pigs were shaved (backs only) and 6 aliquots (50 µl) of compound solution (10 mg/ml) were injected just beneath the skin to form 6 blebs which were outlined with a permanent marker. Pain responses were assessed as above on each bleb at regular intervals up to 4 hours post injection and the duration of pain blockage was recorded for three animals for each test solution.

TABLE 7

| Compound | Duration of Blockage (hours) |
|---|---|
| 1 | 2.5 |
| 2 | 3 |

TABLE 7-continued

| Compound | Duration of Blockage (hours) |
|---|---|
| 3 | 2.5 |
| 11 | 3 |
| Saline | 0 |

Example 36

Ion Channel Modulating Compounds for the Treatment and Prevention of Postoperative Arrhythmias Postoperative arrhythmias such as atrial fibrillation (AF) and atrial flutter (AFL) are common after cardiac surgery. This example demonstrates the efficacy and safety of ion channel modulating compounds of the present invention in converting AF or AFL to sinus rhythm (SR) after coronary artery bypass surgery (CABG), valvular surgery, or both. One specific isomer of Compound 24A, namely (1R,2R)-2-[(3R)-Hydroxy-pyrrolidinyl]-1-(3,4-dimethoxyphenethoxy)cyclohexane monohydrochloride (Compound 24A-1) was used in these studies. This isomer may be synthesized as the racemic mixture of Compound 24A and then isolated by techniques described herein. Alternatively, this isomer may be synthesized directly as described in U.S. patent application Ser. Nos. 10/977,343, 11/201,776, and 11/690,361, each of which is hereby incorporated by reference in its entirety.

Methods:

A multicenter, double-blind, randomized (2:1 Compound 24A-1 vs. placebo), placebo-controlled trial was performed on patients aged≧18 years who had normal SR preceding surgery; had undergone CABG and/or valvular surgery within 7 days; and had documented AF or AFL between 24 hours and 7 days after CABG or valvular surgery. Patients were randomly assigned in a 1:2 ratio to receive a 10-min infusion of placebo or 3 mg/ml Compound 24A-1. After 15 min, a second 10-min infusion of placebo or 2 mg/ml Compound 24A-1 was given if AF or AFL persisted. Postdose evaluations included 24 hour holter monitoring, 12-lead ECG recordings and assessment of vital signs, adverse events and AF/AFL symptoms. The primary efficacy measure was conversion of AF/AFL to SR within 90 min of first exposure for at least 1 minute.

Results:

A total of 190 patients were randomized (63 placebo and 127 Compound 24A-1) and 161 (54 placebo and 107 Compound 24A-1) received treatment. The main reason for not receiving treatment was spontaneous conversion to SR (7 placebo and 17 Compound 24A-1). The mean age was 68, and most patients were men (75%) and white (74%). Among the patients given treatment, 67% had undergone CABG surgery, 24% had valvular surgery, and 9% had both. At entry, 93% of patients had AF and 7% had AFL.

Conversion to SR within 90 minutes was observed in 45% of patients receiving Compound 24A-1 compared to 15% of patients receiving placebo (p=0.0002). The proportion of patients with AF that converted to SR was 47% for patients receiving Compound 24A-1 and 14% for patients receiving placebo (p=0.0001). Of the patients converting to SR with Compound 24A-1, the median time to conversion was 12 minutes and 75% converted on the first dose.

Compound 24A-1 was safe and well tolerated in postoperative patients. In the 24-hr period following stuffy drug administration, adverse events were reported in 32% and 38% of patients given placebo and Compound 24A-1, respectively, of which two were serious (complete AV block and hypotension) in the Compound 24A-1 group. There were no deaths or cases of torsades de pointes.

These studies demonstrated that Compound 24A-1 was effective and well tolerated in the conversion of AF/AFL to SR following surgery and established that the ion channel modulating compounds of the present invention may be used for the treatment and prevention of postoperative arrhythmias.

All publications and patent applications mentioned in this specification or the accompanying Application Data Sheet are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating postoperative arrhythmia in a warm-blooded animal in need thereof, comprising administering to said animal a therapeutically effective amount of a composition comprising a compound having the following structure:

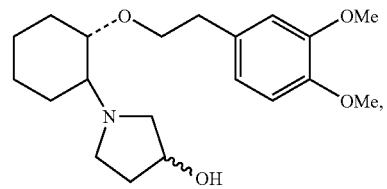

as an isolated enantiomeric or diastereomeric isomer or as a mixture thereof, or as a pharmaceutically acceptable salt thereof, in combination with a pharmaceutically acceptable carrier, excipient or diluent.

2. The method of claim 1 wherein administration is by a route selected from the group consisting of oral, topical, parenteral, sublingual, rectal, vaginal, and intranasal.

3. The method of claim 2 wherein the parenteral administration is selected from the group consisting of subcutaneous injection, intravenous injection, intramuscular injection, epidural injection, intrasternal injection, and infusion.

4. The method of claim 2 wherein the oral administration comprises administering an oral dosage form selected from the group consisting of a powder, a granule, a compressed tablet, a pill, a capsule, a cachet, a chewing gum, a wafer, and a lozenge.

5. The method of claim 1 wherein the arrhythmia is selected from atrial arrhythmia and ventricular arrhythmia.

6. The method of claim 5 wherein the atrial arrhythmia is atrial fibrillation.

7. The method of claim 5 wherein the ventricular arrhythmia is ventricular fibrillation.

8. The method of claim 1 wherein the postoperative arrhythmia occurs following cardiac surgery.

9. The method of claim 8 wherein the cardiac surgery is coronary artery bypass surgery.

10. The method of claim 1 wherein the compound is a mixture of enantiomeric or diastereomeric isomers.

11. The method of claim 10 wherein the compound has the following structure:

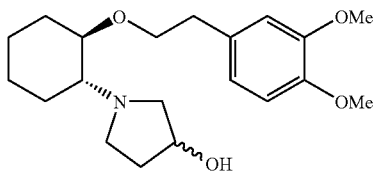

or pharmaceutically acceptable salt thereof.

12. The method of claim 10 wherein the compound has the following structure:

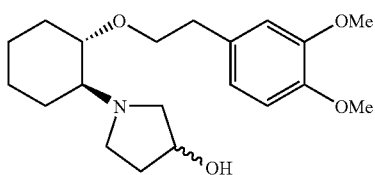

or pharmaceutically acceptable salt thereof.

13. The method of claim 1 wherein the compound is an isolated enantiomeric or diastereomeric isomer.

14. The method of claim 13 wherein the compound has the following structure:

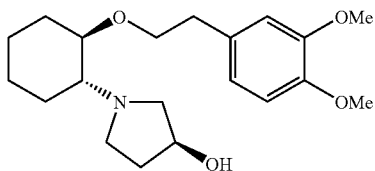

or pharmaceutically acceptable salt thereof.

15. The method of claim 13 wherein the compound has the following structure:

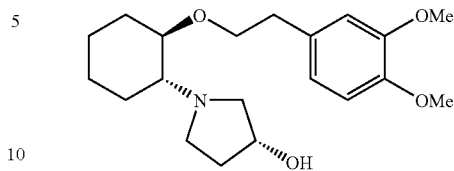

or pharmaceutically acceptable salt thereof.

16. The method of claim 13 wherein the compound has the following structure:

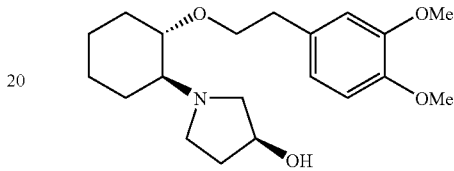

or pharmaceutically acceptable salt thereof.

17. The method of claim 13 wherein the compound has the following structure:

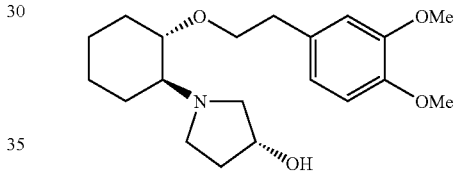

or pharmaceutically acceptable salt thereof.

18. The method of claim 15 wherein the pharmaceutically acceptable salt is a monohydrochloride salt.

* * * * *